(12) United States Patent
Chen et al.

(10) Patent No.: US 7,781,595 B2
(45) Date of Patent: Aug. 24, 2010

(54) BENZIMIDAZOLE DERIVATIVES: PREPARATION AND PHARMACEUTICAL APPLICATIONS

(75) Inventors: DiZhong Chen, Singapore (SG); Hong Yan Song, Singapore (SG); Eric T. Sun, Singapore (SG); Niefang Yu, Singapore (SG); Yong Zou, Beijing (CN)

(73) Assignee: **S*BIO Pte Ltd.**, Singapore Science Park II (SG)

( * ) Notice: Subject to any disclaimer, the term of this patent is extended or adjusted under 35 U.S.C. 154(b) by 654 days.

(21) Appl. No.: 10/572,958

(22) PCT Filed: Sep. 21, 2004

(86) PCT No.: PCT/SG2004/000307

§ 371 (c)(1),
(2), (4) Date: Jul. 13, 2006

(87) PCT Pub. No.: WO2005/028447

PCT Pub. Date: Mar. 31, 2005

(65) Prior Publication Data

US 2007/0043043 A1 Feb. 22, 2007

Related U.S. Application Data

(60) Provisional application No. 60/504,214, filed on Sep. 22, 2003, provisional application No. 60/530,890, filed on Dec. 22, 2003.

(51) Int. Cl.
*A61K 31/4184* (2006.01)
*A61K 31/4439* (2006.01)
*A61K 31/5377* (2006.01)
*C07D 235/06* (2006.01)
*C07D 401/06* (2006.01)
*C07D 401/04* (2006.01)
*C07D 413/06* (2006.01)

(52) U.S. Cl. .................. 548/304.4; 514/234.5; 514/338; 514/394; 544/139; 546/273.4

(58) Field of Classification Search ........................ None
See application file for complete search history.

(56) References Cited

U.S. PATENT DOCUMENTS

| 6,552,065 | B2 | 4/2003 | Remiszewski et al. |
| 2004/0254220 | A1 | 12/2004 | Bressi et al. |
| 2004/0266769 | A1 | 12/2004 | Bressi et al. |
| 2005/0137232 | A1 | 6/2005 | Bressi et al. |
| 2005/0137234 | A1 | 6/2005 | Bressi et al. |
| 2005/0159470 | A1 | 7/2005 | Bressi et al. |

FOREIGN PATENT DOCUMENTS

| WO | WO-93/23041 A1 | 11/1993 |
| WO | WO-00/34254 A1 | 6/2000 |
| WO | WO-00/42022 | 7/2000 |
| WO | WO-01/00207 | 1/2001 |
| WO | WO-01/00213 | 1/2001 |
| WO | WO-01/05390 | 1/2001 |
| WO | WO-01/05393 | 1/2001 |
| WO | WO-01/12604 | 2/2001 |
| WO | WO-01/38322 | 5/2001 |
| WO | WO-01/47883 | 7/2001 |
| WO | WO-02/10137 A2 | 2/2002 |
| WO | WO-02/42273 A2 | 5/2002 |
| WO | WO-02/50062 | 6/2002 |
| WO | WO-03/000254 | 1/2003 |
| WO | WO-03/000682 | 1/2003 |
| WO | WO-03/066579 | 8/2003 |
| WO | WO-03/077855 | 9/2003 |
| WO | WO-03/077914 | 9/2003 |
| WO | WO-03/087089 | 10/2003 |
| WO | WO-2006/101456 A1 | 9/2006 |

OTHER PUBLICATIONS

Dostert et al., CA 86:171447, 1977.*
Wade, P.A. "Transcriptional control at regulatory checkpoints by histone deacetylases: molecular connections between cancer and chromatin" Hum. Mol. Genet. vol. 10, No. 7, pp. 693-698 (2001).
De Ruijter, A.J.M. et al, "Histone deacetylases (HDACs): characterization of the classical HDAC family" Biochem. J., 370, pp. 737-749 (2003).
Richon, V.M. et al, "Second generation hybrid polar compounds are potent inducers of transformed cell differentiation" Proc. Natl. Acad. Sci. USA, vol. 93: pp. 5705-5708 (1996).
Richon, V.M. et al, "A class of hybrid polar inducers of transformed cell differentiation inhibits histone deacetylases" Proc. Natl. Acad. Sci. USA, vol. 95: pp. 3003-3007 (1998).
Butler, L.M. et al, "Suberoylanilide hydroxamic acid, an inhibitor of histone deacetylase, suppresses the growth of prostate cancer cells in vitro and in vivo", Cancer Res. 60, 5165-5170 (2000).
Yoshida, M. et al, "Potent and Specific Inhibition of Mammalian Histone Deacetylase Both in Vivo and in Vitro by Trichostatin A" J. Biol. Chem., vol. 265, No. 28, pp. 17174-17179 (1990).
Kijima, M. et al, "Trapoxin, an Antitumor Cyclic Tetrapeptide, Is an Irreversible Inhibitor of Mammalian Histone Deacetylase" J. Biol. Chem., vol. 268, No. 30, pp. 22429-22435 (1993).
Bouchain, G. et al, "Development of Potential Antitumor Agents. Synthesis and Biological Evaluation of a New Set of Sulfonamide Derivatives as Histone Deacetylase Inhibitors" J. Med. Chem., 46, 820-830 (2003).
Steffan, J.S. et al, "Histone deacetylase inhibitors arrest polyglutamine-dependent neurodegeneration in *Dropsophila*" Nature, vol. 413, pp. 739-743, Oct. 18, 2001.
Schindler et al., "Dissociation between Interleukin—1β mRNA and Protein Synthesis in Human Peripheral Blood Mononuclear Cells" J. Biol. Chem., vol. 265, No. 18, pp. 10232-10237 (1990).

(Continued)

Primary Examiner—Laura L. Stockton
(74) Attorney, Agent, or Firm—Connolly Bove Lodge & Hutz LLP

(57) ABSTRACT

The present invention relates to hydroxamate compounds which are inhibitors of histone deacetylase. More particularly, the present invention relates to benzimidazole containing compounds and methods for their preparation. These compounds may be useful as medicaments for the treatment of proliferative disorders as well as other diseases involving, relating to or associated with dysregulation of histone deacetylase (HDAC).

11 Claims, No Drawings

OTHER PUBLICATIONS

Carballo et al, "Feedback Inhibition of Macrophage Tumor Necrosis Factor-α Production by Tristetraprolin" Science, 1998; vol. 281, pp. 1001-1005.

Dinarello, C.A. and Moldawer L.L. "Proinflammatory and anti-inflammatory cytokines in rheumatoid arthritis. A primer for clinicians." 3rd Edition, Amgen Inc., 2002.

A. Inoue and D. Fujimoto, "Enzymatic Deacetylation of Histone" Biochemical Biophysical Research Communications, 1969, vol. 36, No. 1, pp. 146-150.

J. Taunton et al, "A Mammalian Histone Deacetylase Related to the Yeast Transcriptional Regulator Rpd3p" Science, Apr. 19, 1996, vol. 272: pp. 408-411.

P.A. Wade et al, "Purification of a Histone Deacetylase Complex from *Xenopus laevis*: Preparation of Substrates and Assay Procedures" Methods in Enzymology, 1999, vol. 304, pp. 715-725.

A. Ito et al, "p300/CBP-mediated p53 acetylation is commonly induced by p53-activating agents and inhibited by MDM2" EMBO Journal 2001, vol. 20, No. 6, pp. 1331-1340.

B.D. Strahl and C.D. Allis, "The Language of Covalent Histone Modifications" Nature, Jan. 6, 2000, vol. 403, pp. 41-45.

B. Heltweg and M. Jung, "A Microplate Reader-Based Nonisotopic Histone Deacetylase Activity Assay" Anal. Biochem. 2002, vol. 302, pp. 175-183.

Ito et al, "A Molecular Mechanism of Action of Theophylline: Induction of Histone Deacetylase Activity to Decrease Inflammatory Gene Expression" Proc. Natl. Acad. Sci. USA 2002, vol. 99, No. 13, pp. 8921-8926.

K.J. Bitterman et al, "Inhibition of Silencing and Accelerated Aging by Nicotinamide, a Putative Negative Regulator of Yeast Sir2 and Human SIRT1" J. Biol. Chem. 2002, vol. 277, No. 47, pp. 45099-45107.

S. Milutinovic et al, "Proliferating Cell Nuclear Antigen Associates with Histone Deacetylase Activity, Integrating DNA Replication and Chromatin Modification" J. Biol. Chem. 2002, vol. 277, No. 23, pp. 20974-20978.

Still et al, "Rapid Chromatographic Technique for Preparative Separations with Moderate Resolution" J. Org. Chem., vol. 43, No. 14, pp. 2923-2925 (1978).

Remiszewski et al, "Inhibitors of Human Histone Deacetylase: Synthesis and Enzyme and Cellular Activity of Straight Chain Hydroxamates" J. Med. Chem., 2002, vol. 45, No. 4, pp. 753-757.

Baudy et al, "Design, Synthesis, SAR, and Biological Evaluation of Highly Potent Benzimidazole-Spaced Phosphono-α-Amino Acid Colmpetitive NMDA Antagonists of the AP-6 Type" J. Med. Chem. 2001, 44, 1516-1529.

Yu-Hua Ji et al, "Tris-benzimidazole derivatives: design, synthesis and DNA sequence recognition" Bioorganic & Medical Chemistry 9, pp. 2905-2919 (2001) et al.

Witty et al., Tetrahedron Letters, vol. 37, 1996, 3067-3070.

Gupta et al., Letters in Drug Design & Discovery, vol. 2, 2005, 522-528.

Bare et al., Journal of Medicinal Chemistry, vol. 32, 1989, 2561-2573.

\* cited by examiner

BENZIMIDAZOLE DERIVATIVES: PREPARATION AND PHARMACEUTICAL APPLICATIONS

This application is the national phase under 35 U.S.C. §371 of PCT International Appl. No. PCT/SG2004/000307 that has an international filing date of Sep. 21, 2004, designating the United States of America, which claims the benefit of U.S. Provisional Appl. Nos. 60/504,214, filed Sep. 22, 2003 and 60/530,890, filed Dec. 22, 2003.

FIELD OF THE INVENTION

The present invention relates to hydroxamate compounds that are inhibitors of histone deacetylase. More particularly, the present invention relates to benzimidazole containing compounds and methods for their preparation. These compounds may be useful as medicaments for the treatment of proliferative disorders as well as other diseases involving, relating to or associated with dysregulation of histone deacetylase (HDAC).

BACKGROUND OF THE INVENTION

Local chromatin architecture is generally recognized as an important factor in the regulation of gene expression. The architecture of chromatin, a protein-DNA complex, is strongly influenced by post-translational modifications of the histones which are the protein components. Reversible acetylation of histones is a key component in the regulation of gene expression by altering the accessibility of transcription factors to DNA. In general, increased levels of histone acetylation are associated with increased transcriptional activity, whereas decreased levels of acetylation are associated with repression of gene expression [Wadem P. A. Hum. Mol. Genet. 10, 693-698 (2001), De Ruijter A. J. M. et al, Biochem. J., 370, 737-749 (2003)]. In normal cells, histone deacetylases (HDACs) and histone acetyltransferase together control the level of acetylation of histones to maintain a balance. Inhibition of HDACs results in the accumulation of acetylated histones, which results in a variety of cell type dependent cellular responses, such as apoptosis, necrosis, differentiation, cell survival, inhibition of proliferation and cytostasis.

Inhibitors of HDAC have been studied for their therapeutic effects on cancer cells. For example, suberoylanilide hydroxamic acid (SAHA) is a potent inducer of differentiation and/or apoptosis in murine erythroleukemia, bladder, and myeloma cell lines [Richon V. M. et al, Proc. Natl. Acad. Sci. USA, 93: 5705-5708 (1996), Richon V. M. et al, Proc. Natl. Acad. Sci. USA, 95: 3003-3007 (1998)]. SAHA has been shown to suppress the growth of prostate cancer cells in vitro and in vivo [Butler L. M. et al, Cancer Res. 60, 5165-5170 (2000)]. Other inhibitors of HDAC that have been widely studied for their anti-cancer activities are trichostatin A (TSA) and trapoxin B [Yoshida M. et al, J. Biol. Chem., 265, 17174 (1990), Kijima M. et al, J. Biol. Chem., 268, 22429 (1993)]. Trichostatin A is a reversible inhibitor of mammalian HDAC. Trapoxin B is a cyclic tetrapeptide, which is an irreversible inhibitor of mammalian HDAC. However, due to the in vivo instability of these compounds they are less desirable as anti-cancer drugs. Recently, other small molecule HDAC inhibitors have become available for clinical evaluation [U.S. Pat. No. 6,552,065]. Additional HDAC inhibiting compounds have been reported in the literature [Bouchain G. et al, J. Med. Chem., 46, 820-830 (2003)] and patents [WO 03/066579A2, WO 01/38322 A1]. The in vivo activity of such inhibitors can be directly monitored by their ability to increase the amount of acetylated histones in the biological sample. HDAC inhibitors have been reported to interfere with neurodegenerative processes, for instance, HDAC inhibitors arrest polyglutamine-dependent neurodegeneration [Nature, 413(6857): 739-43, 18 Oct., 2001]. In addition, HDAC inhibitors have also been known to inhibit production of cytokines such as TNF, IFN, IL-1 which are known to be implicated in inflammatory diseases and/or immune system disorders. [J. Biol. Chem. 1990; 265(18): 10230-10237; Science, 1998; 281: 1001-1005; Dinarello C. A. and Moldawer L. L. Proinflammatory and anti-inflammatory cytokines in rheumatoid arthritis. A primer for clinicians. $2^{nd}$ Edition, Amergen Inc., 2000].

Nevertheless, there is still a need to provide further HDAC inhibitors that would be expected to have useful, improved pharmaceutical properties such as anti-cancer agents.

SUMMARY OF THE INVENTION

In one aspect the present invention provides compounds of the formula (I):

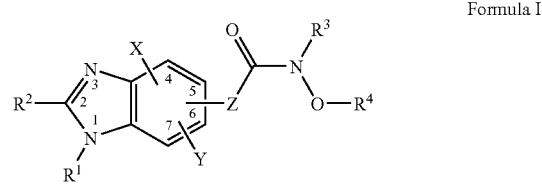

Formula I wherein:

$R^1$ is selected from the group consisting of: H, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, amino, alkylamino, aminoalkyl, acylamino, arylamino, phenoxy, benzyloxy, COOH, alkoxycarbonyl, alkylaminocarbonyl, sulfonyl, alkylsulfonyl, alkylsulfinyl, arylsulfonyl, arylsulfinyl, aminosulfonyl, $SR^6$ and acyl, each of which may be unsubstituted or substituted with one or more substituents independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, arylsulfinyl, aminosulfonyl, aminoalkyl, alkoxyalky, —COOH, —C(O)OR$^5$, —COR$^5$, —SH, —SR$^6$, —OR$^6$ and acyl;

or $R^1$=L;

$R^2$ is selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, amino, alkylamino, aminoalkyl, acylamino, arylamino, phenoxy, benzyloxy, COOH, alkoxycarbonyl, alkylaminocarbonyl, sulfonyl, alkylsulfonyl, alkylsulfinyl, arylsulfonyl, arylsulfinyl, aminosulfonyl, $SR^6$ and acyl, each of which may be unsubstituted or substituted with one or more substituents independently selected from the group consisting of: halogen, $=O$, $=S$, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH, —$COR^5$, —C(O)$OR^5$, —SH, —$SR^6$, —$OR^6$ and acyl;

or $R^2$=L;

$R^3$ is selected from the group consisting of H, $C_1$-$C_6$ alkyl, and acyl; or a metal ion selected from sodium, calcium, magnesium;

X and Y are the same or different and are independently selected from the group consisting of: H, halogen, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH —C(O)$OR^5$, —$COR^5$, —SH, —$SR^6$, —$OR^6$, acyl and —$NR^7R^8$;

$R^4$ is selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl;

Each $R^5$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl;

Each $R^6$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl;

Each $R^7$ and $R^8$ are each independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl;

L is selected from the group consisting of:
a) L=Cy-$L^1$-W—

Wherein
Cy is $C_1$-$C_{15}$ alkyl, aminoalkyl, heterocycloalkyl, cycloalkyl, aryl, aryloxy or heteroaryl, any of which may be optionally substituted one or more substituents independently selected from the group consisting of: halogen, $=O$, $=S$, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH, —C(O)$OR^5$, —$COR^5$, —SH, —$SR^6$, —$OR^6$ and acyl.

$L^1$ is selected from the group consisting of $C_1$-$C_5$ alkyl, which may be optionally substituted with one or more substituents independently selected from the group consisting of: halogen; $=O$; $=S$; —CN; —$NO_2$; alkyl, alkoxy, acylamino, and alkylamino;

W is selected from the group consisting of a single bond, —O—, —S—, —S(O)—, —S(O)$_2$—, —N($R^9$)—, —C(O)N($R^9$)—, —$SO_2$N($R^9$)—, N($R^9$)C(O)—, N($R^9$)$SO_2$—, and —N($R^9$)—C(O)—N($R^{10}$)—;

b) L=Cy-$L^1$-W-$L^2$

Wherein,
Cy is $C_1$-$C_{15}$ alkyl, aminoalkyl, heterocycloalkyl, cycloalkyl, aryl, aryloxy or heteroaryl, any of which may be optionally substituted one or more substituents independently selected from the group consisting of: halogen, $=O$, $=S$, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH, C(O)$OR^5$, —$COR^5$, —SH, —$SR^6$, —$OR^6$ and acyl;

$L^1$ and $L^2$ are the same or different and independently $C_1$-$C_5$ alkyl, which may be optionally substituted with one or more substituents independently selected from the group consisting of: halogen; $=O$; $=S$; —CN; —$NO_2$; —$CF_3$, —$OCF_3$, alkyl, alkoxy, acylamino and alkylamino;

W is selected from the group consisting of a single bond, —O—, —S—, —S(O)—, —S(O)$_2$—, —N($R^9$)—, —C(O)N($R^9$)—, —$SO_2$N($R^9$)—, N($R^9$)C(O)—, N($R^9$)$SO_2$—, and —N($R^9$)—C(O)—N($R^{10}$)—;

c) L=Cy-($CH_2$)m-W—

Wherein,
Cy is $C_1$-$C_{15}$ alkyl, aminoalkyl, heterocycloalkyl, cycloalkyl, aryl, aryloxy or heteroaryl, any of which may be optionally substituted one or more substituents independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH, C(O)OR$^5$, —COR$^5$, —SH, —SR$^6$, —OR$^6$ and acyl;

m is 0, 1, 2, 3, 4 or 5;

W is selected from the group consisting of a single bond, —O—, —S—, —S(O)—, —S(O)$_2$—, —N(R$^9$)—, —C(O)N(R$^9$)—, —SO$_2$N(R$^9$)—, N(R$^9$)C(O)—, N(R$^9$)SO$_2$—, and —N(R$^9$)—C(O)—N(R$^{10}$)—;

d) L=L$^1$-W-L$^2$

L$^1$ and L$^2$ are the same or different and independently selected from C$_1$-C$_5$ alkyl, which may be optionally substituted one or more substituents independently selected from the group consisting of: halogen; =O; =S; —CN; —NO$_2$; —CF$_3$, —OCF$_3$, alkyl, alkoxy, acylamino, alkylamino;

W is selected from the group consisting of a single bond, —O—, —S—, —S(O)—, —S(O)$_2$—, —N(R$^9$)—, —C(O)N(R$^9$)—, —SO$_2$N(R$^9$)—, N(R$^9$)C(O)—, N(R$^9$)SO$_2$—, and —N(R$^9$)—C(O)—N(R$^{10}$)—;

R$^9$ and R$^{10}$ are the same or different and are independently selected from H, C$_1$-C$_6$ alkyl, C$_4$-C$_9$ cycloalkyl, C$_4$-C$_9$ heterocycloalkyl, aryl, heteroaryl, arylalkyl and heteroarylalkyl; and acyl;

Z is a single bond or is selected from —CH$_2$—, —CH$_2$CH$_2$—, —CH=CH— and C$_3$-C$_6$ cycloalkyl, unsubstituted or substituted with one or more substituents independently selected from the group consisting of C$_1$-C$_4$ alkyl; or a pharmaceutically acceptable salt thereof.

One suitable genus of hydroxamic compounds are those of formula Ia:

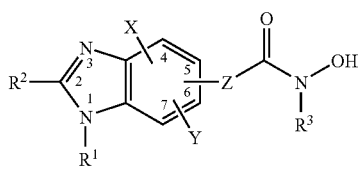

Formula Ia wherein

R$^1$ is selected from the group consisting of: H, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, amino, alkylamino, aminoalkyl, acylamino, arylamino, phenoxy, benzyloxy, COOH, alkoxycarbonyl, alkylaminocarbonyl, sulfonyl, alkylsulfonyl, alkylsulfinyl, arylsulfonyl, arylsulfinyl, aminosulfonyl, SR$^6$ and acyl, each of which may be unsubstituted or substituted with one or more substituents independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, arylsulfinyl, aminosulfonyl, aminoalkyl, alkoxyalky, —COOH, —C(O)OR$^5$, —COR$^5$, —SH, —SR$^6$, —OR$^6$ and acyl; or R$^1$=L;

R$^2$ is selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl hydroxy, hydroxyalkyl, alkoxy, alkoxyalkyl, alkoxyaryl, alkenyloxy, alkynyloxy, cycloalkylkoxy, heterocycloalkyloxy, aryloxy, heteroaryloxy, arylalkyloxy, amino, alkylamino, aminoalkyl, acylamino, arylamino, phenoxy, benzyloxy, COOH, alkoxycarbonyl, alkylaminocarbonyl, sulfonyl, alkylsulfonyl, alkylsulfinyl, arylsulfonyl, arylsulfinyl, aminosulfonyl, SR$^6$ and acyl, each of which may be unsubstituted or substituted with one or more substituents independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH, —COR$^5$, —C(O)OR$^5$, —SH, —SR$^6$, —OR$^6$ and acyl;

or R$^2$=L;

R$^3$ is selected from the group consisting of: H, C$_1$-C$_6$ alkyl, and acyl; or a metal ion selected from sodium, calcium, magnesium;

X and Y are the same or different and are independently selected from the group consisting of: H, halogen, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH —C(O)OR$^5$, —COR$^5$, —SH, —SR$^6$, —OR$^6$, acyl and —NR$^7$R$^8$;

Each $R^5$ is independently selected from the group consisting of: alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl;

Each $R^6$ is independently selected from the group consisting of: alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl;

Each $R^7$ and $R^8$ are each independently selected from the group consisting of: alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl;

L is selected from the group consisting of:

a) L=Cy-$L^1$-W—

Wherein

Cy is $C_1$-$C_{15}$ alkyl, aminoalkyl, heterocycloalkyl, cycloalkyl, aryl, aryloxy, or heteroaryl any of which may be optionally substituted one or more substituents independently selected from the group consisting of: halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH, —C(O)$OR^5$, —$COR^5$, —SH, —$SR^6$, —$OR^6$, and acyl;

$L^1$ is selected from the group consisting of $C_1$-$C_5$ alkyl, which may be optionally substituted with one or more substituents independently selected from the group consisting of: halogen; =O; =S; —CN; —$NO_2$; alkyl, alkoxy, acylamino, and alkylamino;

W is selected from the group consisting of a single bond, —O—, —S—, —S(O)—, —S(O)$_2$—, —N($R^9$)—, —C(O)N($R^9$)—, —$SO_2$N($R^9$)—, N($R^9$)C(O)—, N($R^9$)$SO_2$—, and —N($R^9$)—C(O)—N($R^{10}$)—;

b) L=Cy-$L^1$-W-$L^2$

Wherein,

Cy is $C_1$-$C_{15}$ alkyl, aminoalkyl, heterocycloalkyl, cycloalkyl, aryl, aryloxy or heteroaryl, any of which may be optionally substituted one or more substituents independently selected from the group consisting of: halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH, C(O)$OR^5$, —$COR^5$, —SH, —$SR^6$, —$OR^6$ and acyl;

$L^1$ and $L^2$ are the same or different and independently $C_1$-$C_5$ alkyl, which may be optionally substituted with one or more substituents independently selected from the group consisting of: halogen; =O; =S; —CN; —$NO_2$; —$CF_3$, —$OCF_3$, alkyl, alkoxy, acylamino and alkylamino;

W is selected from the group consisting of a single bond, —O—, —S—, —S(O)—, —S(O)$_2$—, —N($R^9$)—, —C(O)N($R^9$)—, —$SO_2$N($R^9$)—, N($R^9$)C(O)—, N($R^9$)$SO_2$—, and —N($R^9$)—C(O)—N($R^{10}$)—;

c) L=Cy-(CH$_2$)m-W—

Wherein,

Cy is $C_1$-$C_{15}$ alkyl, aminoalkyl, heterocycloalkyl, cycloalkyl, aryl, aryloxy or heteroaryl, any of which may be optionally substituted one or more substituents independently selected from the group consisting of halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH, C(O)$OR^5$, —$COR^5$, —SH, —$SR^6$, $OR^6$ and acyl;

m is 0, 1, 2, 3, 4 or 5;

W is selected from the group consisting of a single bond, —O—, —S—, —S(O)—, —S(O)$_2$—, —N($R^9$)—, —C(O)N($R^9$)—, —$SO_2$N($R^9$)—, N($R^9$)C(O)—, N($R^9$)$SO_2$—, and —N($R^9$)—C(O)—N($R^{10}$)—;

d) L=$L^1$-W-$L^2$ $L^1$ and $L^2$ are the same or different and independently selected from $C_1$-$C_5$ alkyl, which may be optionally substituted one or more substituents independently selected from the group consisting of: halogen; =O; =S; —CN; —$NO_2$; —$CF_3$, —$OCF_3$. alkyl, alkoxy, acylamino, alkylamino;

W is selected from the group consisting of a single bond, —O—, —S—, —S(O)—, —S(O)$_2$—, —N($R^9$)—, —C(O)N($R^9$)—, —$SO_2$N($R^9$)—, N($R^9$)C(O)—, N($R^9$)$SO_2$—, and —N($R^9$)—C(O)—N($R^{10}$)—;

$R^9$ and $R^{10}$ are the same or different and are independently selected from H, $C_1$-$C_6$ alkyl, $C_4$-$C_9$ cycloalkyl, $C_4$-$C_9$ heterocycloalkyl, aryl, heteroaryl, arylalkyl, heteroarylalkyl; and acyl;

Z is a single bond or is selected from —$CH_2$—, —$CH_2CH_2$—, —CH=CH—, $C_3$-$C_6$ cycloalkyl, unsubstituted or substituted with one or more substituents independently selected from the group consisting of $C_1$-$C_4$ alkyl;

or a pharmaceutically acceptable salt thereof.

Another group of useful compounds are those of the formula Ib:

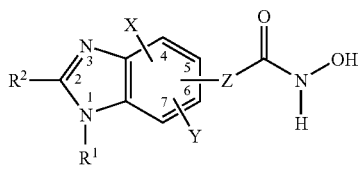

Formula Ib wherein
R¹ is selected from the group consisting of: H, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, amino, alkylamino, aminoalkyl, acylamino, arylamino, phenoxy, benzyloxy, COOH, alkoxycarbonyl, alkylaminocarbonyl, sulfonyl, alkylsulfonyl, alkylsulfinyl, arylsulfonyl, arylsulfinyl, aminosulfonyl, SR⁸ and acyl, each of which may be unsubstituted or substituted with one or more substituents independently selected from the group consisting of: halogen, =O, =S, —CN, —NO₂, —CF₃, —OCF₃, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, arylsulfinyl, aminosulfonyl, aminoalkyl, alkoxyalky, —COOH, —C(O)OR⁵, —COR⁵, —SH, —SR⁶, —OR⁶ and acyl; or R¹=L;

R² is selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, amino, alkylamino, aminoalkyl, acylamino, arylamino, phenoxy, benzyloxy, COOH, alkoxycarbonyl, alkylaminocarbonyl, sulfonyl, alkylsulfonyl, alkylsulfinyl, arylsulfonyl, arylsulfinyl, aminosulfonyl, SR⁶ and acyl, each of which may be unsubstituted or substituted with one or more substituents independently selected from the group consisting of: halogen, =O, =S, —CN, —NO₂, —CF₃, —OCF₃, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH, —COR⁵, —C(O)OR⁵, —SH, —SR⁶, —OR⁶ and acyl;

or R²=L;

X and Y are the same or different and are independently selected from the group consisting of: H, halogen, —CN, —NO₂, —CF₃, —OCF₃, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH —C(O)OR⁵, —COR⁵, —SH, —SR⁶, acyl and —NR⁷R⁸;

Each R⁵ is independently selected from the group consisting of: alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl;

Each R⁶ is independently selected from the group consisting of: alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl;

Each R⁷ and R⁸ are each independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl;

L is selected from the group consisting of:
a) L=Cy-L¹-W—
Wherein
Cy is $C_1$-$C_{15}$ alkyl, aminoalkyl, heterocycloalkyl, cycloalkyl, aryl, aryloxy or heteroaryl, any of which may be optionally substituted one or more substituents independently selected from the group consisting of: halogen, =O, =S, —CN, —NO₂, —CF₃, —OCF₃, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH, —C(O)OR⁵, —COR⁵, —SH, —SR⁶, —OR⁶ and acyl.

L¹ is selected from the group consisting of $C_1$-$C_5$ alkyl, which may be optionally substituted with one or more substituents independently selected from the group consisting of: halogen; =O; =S; —CN; —NO₂; alkyl, alkoxy, acylamino, and alkylamino;

W is selected from the group consisting of a single bond, —O—, —S—, —S(O)—, —S(O)₂—, —N(R$^9$)—, —C(O)N(R$^9$)—, —SO$_2$N(R$^9$)—, N(R$^9$)C(O)—, N(R$^9$)SO$_2$—, and —N(R$^9$)—C(O)—N(R$^{10}$)—;

b) L=Cy-L$^1$-W-L$^2$

Wherein,

Cy is C$_1$-C$_{15}$ alkyl, aminoalkyl, heterocycloalkyl, cycloalkyl, aryl, aryloxy or heteroaryl, any of which may be optionally substituted one or more substituents independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH, C(O)OR$^5$, —COR$^5$, —SH, —SR$^6$, —OR$^6$ and acyl;

L$^1$ and L$^2$ are the same or different and independently C$_1$-C$_5$ alkyl, which may be optionally substituted with one or more substituents independently selected from the group consisting of: halogen; =O; =S; —CN; —NO$_2$; —CF$_3$, —OCF$_3$, alkyl, alkoxy, acylamino and alkylamino;

W is selected from the group consisting of a single bond, —O—, —S—, —S(O)—, —S(O)$_2$—, —N(R$^9$)—, —C(O)N(R$^9$)—, —SO$_2$N(R$^9$)—, N(R$^9$)C(O)—, N(R$^9$)SO$_2$—, and —N(R$^9$)—C(O)—N(R$^{10}$)—;

c) L=Cy-(CH$_2$)m-W—

Wherein,

Cy is C$_1$-C$_{15}$ alkyl, aminoalkyl, heterocycloalkyl, cycloalkyl, aryl, aryloxy or heteroaryl, any of which may be optionally substituted one or more substituents independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH, C(O)OR$^5$, —COR$^5$, —SH, —SR$^6$, —OR$^6$ and acyl m is 0, 1, 2, 3, 4 or 5;

W is selected from the group consisting of a single bond, —O—, —S—, —S(O)—, —S(O)$_2$—, —N(R$^9$)—, —C(O)N(R$^9$)—, —SO$_2$N(R$^9$)—, N(R$^9$)C(O)—, N(R$^9$)SO$_2$—, and —N(R$^9$)—C(O)—N(R$^{10}$)—;

d) L=L$^1$-W-L$^2$

L$^1$ and L$^2$ are the same or different and independently selected from C$_1$-C$_5$ alkyl, which may be optionally substituted one or more substituents independently selected from the group consisting of: halogen; =O; =S; —CN; —NO$_2$; —CF$_3$, —OCF$_3$ alkyl, alkoxy, acylamino, alkylamino;

W is selected from the group consisting of a single bond, —O—, —S—, —S(O)—, —S(O)$_2$—, —N(R$^9$)—, —C(O)N(R$^9$)—, —SO$_2$N(R$^9$)—, N(R$^9$)C(O)—, N(R$^9$)SO$_2$—, and —N(R$^9$)—C(O)—N(R$^{10}$)—;

R$^9$ and R$^{10}$ are the same or different and are independently selected from H, C$_1$-C$_6$ alkyl, C$_4$-C$_9$ cycloalkyl, C$_4$-C$_9$ heterocycloalkyl, aryl, heteroaryl, arylalkyl, heteroarylalkyl; and acyl;

Z is a single bond or is selected from —CH$_2$—, —CH$_2$CH$_2$—, —CH=CH—, C$_3$-C$_6$ cycloalkyl, unsubstituted or substituted with one or more substituents independently selected from the group consisting of C$_1$-C$_4$ alkyl;

or a pharmaceutically acceptable salt thereof.

As with any group of structurally related compounds which possess a particular utility, certain groups are preferred for the compounds of the Formula (I), (Ia) and (Ib) in their end use application.

In certain preferred embodiments R$^1$ is selected from the group consisting of C$_1$-C$_{10}$ alkyl, alkenyl, heteroalkyl, haloalkyl, alkynyl, aryl, cycloalkyl, heterocycloalkyl, heteroaryl, C$_4$-C$_9$ heterocycloalkylalkyl, cycloalkylalkyl, arylalkyl, and heteroarylalkyl each of which may be substituted as previously stated.

In another embodiment it is preferred that R$^1$ is selected from the group consisting of H, hydroxyalkyl, alkyl, arylalkyl, heteroarylalkyl, alkoxyalkyl, aminoalkyl, and heterocycloalkyl each of which may be substituted as previously stated.

In another embodiment it is preferred that R$^1$ is selected from the group consisting of H, hydroxyalkyl, alkyl, alkoxyalkyl, and aminoalkyl each of which may be substituted as previously stated.

In another embodiment it is preferred that if R$^1$ is alkyl or heteroalkyl then it is not substituted by a cycloalkyl, aryl, heteroaryl, or heterocycloalkyl.

Particularly preferred values of R$^1$ are:

H; methyl; (pyridin-2-yl)methyl; (pyridin-3-yl)methyl; ethyl; 2-hydroxy-ethyl; 2-(pyridin-2-yl)ethyl; 2-(pyridin-3-yl) ethyl; 2-phenyl-ethyl; 2-carboxy-ethyl; 2-(morpholin-4-yl)-ethyl; 2-(piperidin-1-yl)-ethyl; 2-(pyrollidin-1-yl)-ethyl; 2-diethylamino-ethyl; propyl; 2,3-di-hydroxy-propyl; 3-hydroxy-propyl; 3-methoxy-propyl; 3-isopropoxy-propyl; 2,2-dimethyl-propyl; 3-dimethylamino-propyl; 3-dimethylamino-2,2-dimethyl-propyl; 3-(2-oxo-pyrollidin-1-yl)-propyl; 3-(morpholin-4-yl)-propyl; 3-(imadazol-1-yl)-propyl; 3-(4-methyl-piperidin-1-yl)-propyl; 3-(pyrollidin-1-yl)-propyl; 4-dimethylamino-butyl; 5-hydroxy-pentyl; allyl; benzyl; and 3,4,5-trimethoxybenzyl.

In certain preferred embodiments R$^2$ is selected from the group consisting of H, Halogen, C$_1$-C$_{10}$ alkyl, alkenyl, heteroalkyl, haloalkyl, alkynyl, aryl, cycloalkyl, heterocycloalkyl, heteroaryl, C$_4$-C$_9$ heterocycloalkylalkyl, cycloalkylalkyl, arylalkyl, and heteroarylalkyl each of which may be substituted as previously stated.

In another embodiment it is preferred that R$^2$ is selected from the group consisting of H, alkyl, arylalkyl, aryl, heteroaryl, heteroalkyl, cycloalkyl, and L, each of which may be substituted as previously stated.

In another embodiment it is preferred that R$^2$ is selected from the group consisting of H, hydroxyalkyl, alkyl, alkoxyalkyl, and aminoalkyl each of which may be substituted as previously stated.

In another embodiment it is preferred that if $R^2$ is alkyl or heteroalkyl then it is not substituted by a cycloalkyl, aryl, heteroaryl, or heterocycloalkyl.

Particularly preferred values of $R^2$ are: H; methyl; benzylamino-methyl; dibenzylamino-methyl; [2-(4-fluoro-phenyl)-acetylamino]-methyl; [2-(4-methoxy-phenyl)-acetylamino]-methyl; 4-methoxy-benzylamino-methyl; benzyloxy-methyl; phenylacetylamino-methyl; 1-amino-2-phenyl-ethyl; 2-benzylamino-ethyl; 2-(3-methoxy-phenyl)-ethyl; 2-(pyridin-3-yl)ethyl; 2-(2-phenoxyacetylamino)-ethyl; 2-benzenesulphonylamino-ethyl; 2-phenyl-ethyl; isopropyl; 2-phenyl-propyl; 3-phenyl-propyl; 3-phenoxypropyl; 3-(1H-indol-3-yl)-propyl; 4-methoxy-phenyl; 4-fluoro-phenyl; 4-benzyloxy-3-methoxy-phenyl; isobutyl; cyclohexyl; octyl; benzyl; pyridin-2-yl; pyridin-4-yl; thiophen-3-yl; benzylsulfanyl, and 2-phenylmethansulfanyl.

If $R^1$ or $R^2$ are substituted particularly preferred substituents are selected from the group consisting of: halogen, =O, =S, —CN, —NO$_2$, alkyl, alkenyl, heteroalkyl, haloalkyl, alkynyl, aryl, cycloalkyl, heterocycloalkyl, heteroaryl, hydroxy, hydroxyalkyl, alkoxy, alkylamino, aminoalkyl, acylamino, phenoxy, alkoxyalkyl, benzyloxy, alkylsulfonyl, arylsulfonyl, aminosulfonyl, —C(O)OR$^5$, COOH, SH, and acyl.

X and Y may be the same or different and are preferably H, halogen, $C_1$-$C_4$ alkyl, —CF$_3$, —NO$_2$, —C(O)R$^5$, —OR$^6$, —SR$^6$, —CN and NR$^7$R$^8$.

X is most preferably H;
Y is most preferably H;
X and Y are most preferably at the 4 and 7 positions of the aromatic ring.

$R_3$ is preferably H, $C_1$-$C_6$ alkyl, or acyl, more preferably H or $C_1$-$C_4$ alkyl, most preferably H;

$R_4$ is preferably H or $C_1$-$C_4$ alkyl, most preferably H;

$R_5$ is preferably $C_1$-$C_4$ alkyl, heteroalkyl, or acyl, most preferably methyl;

$R_6$ is preferably $C_1$-$C_4$ alkyl, heteroalkyl or acyl, most preferably $C_1$-$C_4$ alkyl;

$R_7$ and $R_8$ are preferably selected from the group consisting of H, $C_1$-$C_6$ alkyl, $C_4$-$C_9$cycloalkyl, $C_4$-$C_9$heterocycloalkyl, aryl, heteroaryl, arylalkyl, and heteroarylalkyl The Z moiety is preferably a group of formula —CH=CH—. The moiety is preferably in the "E" configuration and is preferably at the 5 or 6 position, most preferably the 5 position.

In addition to compounds of Formula I, the embodiments disclosed are also directed to pharmaceutically acceptable salts, pharmaceutically acceptable prodrugs, and pharmaceutically active metabolites of such compounds, and pharmaceutically acceptable salts of such metabolites. Such compounds, salts, prodrugs and metabolites are at times collectively referred to herein as "HDAC inhibiting agents" or "HDAC inhibitors".

The invention also relates to pharmaceutical compositions including a compound of the invention with a pharmaceutically acceptable carrier, diluent or excipient.

In yet a further aspect the present invention provides a method of treatment of a disorder caused by, associated with or accompanied by disruptions of cell proliferation and/or angiogenesis including administration of a therapeutically effective amount of a compound of formula (I).

The method preferably includes administration of a compound of formula (Ia), more preferably a compound of formula (Ib) as described herein.

The disorder is preferably selected from the group consisting of but not limited to cancer, inflammatory diseases/immune system disorders, angiofibroma, cardiovascular diseases (e.g. restenosis, arteriosclerosis), fibrotic diseases (e.g. liver fibrosis), diabetes, autoimmune diseases, chronic and acute neurodegenerative disease like disruptions of nerval tissue, Huntington's disease and infectious diseases like fungal, bacterial and viral infections. In another embodiment the disorder is a proliferative disorder. The proliferative disorder is preferably cancer.

The invention also provides agents for the treatment of a disorder caused by, associated with or accompanied by disruptions of cell proliferation and/or angiogenesis including a compound of formula (I) as disclosed herein. The agent is preferably an anti-cancer agent.

The agent preferably contains a compound of formula (Ia), more preferably a compound of formula (Ib).

The invention also relates to the use of compounds of formula (I) in the preparation of a medicament for the treatment of a disorder caused by, associated with or accompanied by disruptions of cell proliferation and/or angiogenesis. The disorder is preferably a proliferative disorder, most preferably a cancer.

The compounds of the present invention surprisingly show low toxicity, together with a potent anti-proliferative activity.

In yet a further embodiment the invention provides a method of treatment of a disorder, disease or condition that can be treated by the inhibition of histone deacetylase including administration of a therapeutically effective amount of a compound of formula (1).

The method preferably includes administration of a compound of formula (Ia), more preferably a compound of formula (Ib) as described herein.

The disorder is preferably selected the group consisting of but not limited to proliferative disorders (e.g. cancers); Neurodegenerative diseases including Huntington's Disease, Polyglutamine disease, Parkinson's Disease, Alzheimer's Disease, Seizures, Striatonigral degeneration, Progressive supranuclear palsy, Torsion dystonia, Spasmodic torticollis and dyskinesis, Familial tremor, Gilles de la Tourette syndrome, Diffuse Lewy body disease, Progressive supranuclear palsy, Pick's disease, Intracerebral haemorrhage Primary lateral sclerosis, Spinal muscular atrophy, Amyotrophic lateral sclerosis, Hypertrophic interstitial polyneuropathy, Retinitis pigmentosa, Hereditary optic atrophy, Hereditary spastic paraplegia, Progressive ataxia and Shy-Drager syndrome; Metabolic diseases including Type 2 diabetes; Degenerative Diseases of the Eye including Glaucoma, Age-related macular degeneration, Rubeotic glaucoma; Inflammatory diseases and/or Immune system disorders including Rheumatoid Arthritis (RA), Osteoarthritis, Juvenile chronic arthritis, Graft versus Host disease, Psoriasis, Asthma, Spondyloarthropathy, psoriasis, Crohn's Disease, inflammatory bowel disease, Colitis Ulcerosa, Alcoholic hepatitis, Diabetes, Sjoegrens's syndrome, Multiple Sclerosis, Ankylosing spondylitis, Membranous glomerulopathy, Discogenic pain, Systemic Lupus Erythematosus; Disease involving angiogenesis including cancer, psoriasis, rheumatoid arthritis; Psychological disorders including bipolar disease, schizophrenia, depression and dementia; Cardiovascular Diseases including Heart failure, restenosis and arteriosclerosis; Fibrotic diseases including liver fibrosis, cystic fibrosis and angiofibroma; Infectious diseases including Fungal infections, such as *Candida Albicans*, Bacterial infections, Viral infections, such as Herpes Simplex, Protozoal infections, such as Malaria, *Leishmania* infection, *Trypanosoma brucei* infection, Toxoplasmosis and coccidiosis and Haematopoietic disorders including thalassemia, anemia and sickle cell anemia.

The invention also provides agents for the treatment of a disorder, disease or condition that can be treated by the inhibition of histone deacetylase including a compound of formula (I) as disclosed herein. The agent is preferably an anti-cancer agent.

The invention also relates to the use of compounds of formula (I) in the preparation of a medicament for the treatment of a disorder, disease or condition that can be treated by the inhibition of histone deacetylase.

The invention also provides a method for inhibiting cell proliferation including administration of an effective amount of a compound according to formula (I).

In yet an even further aspect the invention provides a method of treatment of a neurodegenerative disorder in a patient including administration of a therapeutically effective amount of a compound of formula (I). The method preferably includes administration of a compound of formula (Ia), more preferably a compound of formula (Ib) as described herein. The neurodegenerative disorder is preferably Huntington's Disease.

The invention also provides agents for the treatment of neurodegenerative disorder including a compound of formula (I) as disclosed herein. The agent is preferably anti-Huntington's disease agent.

The invention also relates to the use of compounds of formula (I) in the preparation of a medicament for the treatment of a neurodegenerative disorder. The neurodegenerative disorder is preferably Huntington's Disease.

In yet an even further aspect the invention provides a method of treatment of an inflammatory disease and/or immune system disorder in a patient including administration of a therapeutically effective amount of a compound of formula (1). The method preferably includes administration of a compound of formula (Ia), more preferably a compound of formula (Ib) as described herein. In one embodiment the inflammatory disease and/or immune system disorder is rheumatoid arthritis. In another embodiment the inflammatory disease and/or immune system disorder is Systemic Lupus Erythematosus.

The invention also provides agents for the treatment of inflammatory disease and/or immune system disorder including a compound of formula (I) as disclosed herein.

The invention also relates to the use of compounds of formula (I) in the preparation of a medicament for the treatment of inflammatory disease and/or immune system disorder. In one embodiment the inflammatory disease and/or immune system disorder is rheumatoid arthritis. In another embodiment the inflammatory disease and/or immune system disorder is Systemic Lupus Erythematosus.

To monitor the efficacy of such compounds the invention describes a method suitable to detect and quantify levels of acetylated histone in samples from human or animal species such as tumor tissue, brain, and blood. The method is based on an enzyme-linked immunosorbant assay (ELISA) and may be used for the quantification of acetylated histones in cellular extracts or samples from human or animal species such as tumor tissue, brain, and blood. Preferable over conventional systems, the ELISA allows high throughput, quantitative determinations of the concentration of acetylated histones as measurement for the efficacy of the drug treatment or the potency of the drug in a respective biological test system. For a general review of conventional ELISA techniques, please refer to Crowther J R (1995) ELISA theory and practice in Method in molecular biology vol. 42, Humana.

In yet an even further aspect the invention provides a method for measuring an acetylated histone concentration in a biological sample using an enzyme-linked immunosorbant assay, the enzyme-linked immunosorbant assay including a combination of a primary capture antibody, or a portion thereof, and secondary detection antibody, or a portion thereof.

The primary capture antibody is preferably selected from the group consisting of: an anti-H3 monoclonal antibody, an anti-acetylated H3 polyclonal antibody, a goat anti-H3 polyclonal antibody, a goat antiacetylated H3 polyclonal antibody and a combination thereof. The secondary detection antibody is preferably selected from the group consisting of: an anti-H3 monoclonal antibody, an anti-acetylated H3 polyclonal antibody, a goat anti-H3 polyclonal antibody, a goat anti-acetylated H3 polyclonal antibody and a combination thereof.

In a particularly preferred embodiment the primary capture antibody is a mouse anti-H3 monoclonal antibody and the secondary detection antibody is a rat anti-acetylated H3 polyclonal antibody.

The invention also provides a method for identifying the pharmacological effect of a histone deacetylase inhibitor in a cell, the method including the steps of:
a) providing a cell that has been treated with a histone deacetylase inhibitor;
b) measuring the acetylated histone concentration in the cell by one of the methods as stated above; and
c) comparing the acetylated histone concentration with the acetylated histone concentration of a control sample.

In a preferred embodiment the control sample is derived from a cell that has not been treated with a histone deacetylase inhibitor. In another preferred embodiment the cell is a tumour cell.

The histone deacetylase inhibitor preferably includes a compound of formula (1).

The invention also provides a method for identifying the pharmacological effect of a histone deacetylase inhibitor in a subject, the method including the steps of:
a) obtaining a biological sample from a subject that has been treated with a histone deacetylase inhibitor;
b) measuring the acetylated histone concentration in the biological sample by a method according to the invention as described above; and
c) comparing the acetylated histone concentration with the acetylated histone concentration of a control sample.

The control sample is preferably a biological sample derived from a subject that has not been treated with a histone deacetylase inhibitor.

In the methods of the invention the biological sample is preferably selected from the group consisting of tissue, blood, serum, plasma, urine, saliva and a combination thereof.

DETAILED DESCRIPTION OF THE EMBODIMENTS

There are disclosed hydroxamate compounds, for example benzimidazoles containing hydroxamic acid in one of the substituents, that may be inhibitors of deacetylases, including but not limited to inhibitors of histone deacetylases. The hydroxamate compounds may be suitable for prevention or treatment of a disorder caused by, associated with or accompanied by disruptions of cell proliferation and/or angiogenesis when used either alone or together with a pharmaceutically acceptable carrier, diluent or excipient. An example of such a disorder is cancer.

As used herein the term 'cancer' is a general term intended to encompass the vast number of conditions that are characterised by uncontrolled abnormal growth of cells.

It is anticipated that the compounds of the invention will be useful in treating various cancers including but not limited to bone cancers including Ewing's sarcoma, osteosarcoma, chondrosarcoma and the like, brain and CNS tumours including acoustic neuroma, neuroblastomas, glioma and other brain tumours, spinal cord tumours, breast cancers, colorectal cancers, advanced colorectal adenocarcinomas, endocrine cancers including adenocortical carcinoma, pancreatic cancer, pituitary cancer, thyroid cancer, parathyroid cancer, thymus cancer, multiple endocrine neoplasma, gastrointestinal cancers including stomach cancer, esophageal cancer, small intestine cancer, Liver cancer, extra hepatic bile duct cancer, gastrointestinal carcinoid tumour, gall bladder cancer, genitourinary cancers including testicular cancer, penile cancer, prostrate cancer, gynecological cancers including cervical cancer, ovarian cancer, vaginal cancer, uterus/endometrium cancer, vulva cancer, gestational trophoblastic cancer, fallopian tube cancer, uterine sarcoma, head and neck cancers including oral cavity cancer, lip cancer, salivary gland cancer, larynx cancer, hypopharynx cancer, orthopharynx cancer, nasal cancer, paranasal cancer, nasopharynx cancer, leukemias including childhood leukemia, acute lymphocytic leukemia, acute myeloid leukemia, chronic lymphocytic leukemia, chronic myeloid leukemia, hairy cell leukemia, acute promyelocytic leukemia, plasma cell leukemia, myelomas, haematological disorders including myelodysplastic syndromes, myeloproliferative disorders, aplastic anemia, Fanconi anemia, Waldenstroms Macroglobulinemia, lung cancers including small cell lung cancer, non-small cell lung cancer, lymphomas including Hodgkin's disease, non-Hodgkin's lymphoma, cutaneous T-cell lymphoma, peripheral T-cell lymphoma, AIDS related Lymphoma, eye cancers including retinoblastoma, intraocular melanoma, skin cancers including melanoma, non-melanoma skin cancer, merkel cell cancer, soft tissue sarcomas such as childhood soft tissue sarcoma, adult soft tissue sarcoma, Kaposi's sarcoma, urinary system cancers including kidney cancer, Wilms tumour, bladder cancer, urethral cancer, and transitional cell cancer.

Preferred cancers that may be treated by the compounds of the present invention are breast cancer, lung cancer, ovarian cancer, prostate cancer, head and neck cancer, renal, gastric and brain cancer.

Preferred cancers that may be treated by compounds of the present inventions are cutaneous T-cell lymphoma (CTCL) and peripheral T-cell lymphoma.

Preferred cancers that may be treated by compounds of the present invention include solid tumors and hematologic malignancies.

The compounds may also be used in the treatment of a disorder involving, relating to or, associated with dysregulation of histone deacetylase (HDAC).

There are a number of disorders that have been implicated by or known to be mediated at least in part by HDAC activity, where HDAC activity is known to play a role in triggering disease onset, or whose symptoms are known or have been shown to be alleviated by HDAC inhibitors. Disorders of this type that would be expected to be amenable to treatment with the compounds of the invention include the following but not limited to:

Proliferative disorders (e.g. cancers); Neurodegenerative diseases including Huntington's Disease, Polyglutamine disease, Parkinson's Disease, Alzheimer's Disease, Seizures, Striatonigral degeneration, Progressive supranuclear palsy, Torsion dystonia, Spasmodic torticollis and dyskinesis, Familial tremor, Gilles de la Tourette syndrome, Diffuse Lewy body disease, Progressive supranuclear palsy, Pick's disease, intracerebreal haemorrphage, Primary lateral sclerosis, Spinal muscular atrophy, Amyotrophic lateral sclerosis, Hypertrophic interstitial polyneuropathy, Retinitis pigmentosa, Hereditary optic atrophy, Hereditary spastic paraplegia, Progressive ataxia and Shy-Drager syndrome; Metabolic diseases including Type 2 diabetes; Degenerative Diseases of the Eye including Glaucoma, Age-related macular degeneration, Rubeotic glaucoma; Inflammatory diseases and/or Immune system disorders including Rheumatoid Arthritis (RA), Osteoarthritis, Juvenile chronic arthritis, Graft versus Host disease, Psoriasis, Asthma, Spondyloarthropathy, psoriasis, Crohn's Disease, inflammatory bowel disease Colitis Ulcerosa, Alcoholic hepatitis, Diabetes, Sjoegrens's syndrome, Multiple Sclerosis, Ankylosing spondylitis, Membranous glomerulopathy, Discogenic pain, Systemic Lupus Erythematosus; Disease involving angiogenesis including cancer, psoriasis, rheumatoid arthritis; Psychological disorders including bipolar disease, schizophrenia, mainia, depression and dementia; Cardiovascular Diseases including heart failure, restenosis and arteriosclerosis; Fibrotic diseases including liver fibrosis, cystic fibrosis and angiofibroma; Infectious diseases including Fungal infections, such as *Candida Albicans*, Bacterial infections, Viral infections, such as Herpes Simplex, Protozoal infections, such as Malaria, *Leishmania* infection, *Trypanosoma brucei* infection, Toxoplasmosis and coccidiosis and Haematopoietic disorders including thalassemia, anemia and sickle cell anemia.

The hydroxamate compounds of the present invention have the following structure (I):

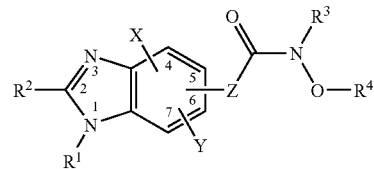

Formula I wherein $R^1$ is selected from the group consisting of: H, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, arylheteroalkyl, heterocycloalkylheteroalkyl, heteroarylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, amino, alkylamino, aminoalkyl, acylamino, arylamino, phenoxy, benzyloxy, COOH, alkoxycarbonyl, alkylaminocarbonyl, sulfonyl, alkylsulfonyl, alkylsulfinyl, arylsulfonyl, arylsulfinyl, aminosulfonyl, $SR^6$ and acyl, each of which may be unsubstituted or substituted with one or more substituents independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, arylsulfinyl, aminosulfonyl, aminoalkyl, alkoxyalky, —COOH, —C(O)OR$^5$, —COR$^5$, —SH, —SR$^6$, —OR$^6$ and acyl; or $R^1$=L;

$R^2$ is selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl hydroxy, hydroxyalkyl, alkoxy, alkoxyalkyl, alkoxyaryl, alkenyloxy, alkynyloxy, cycloalkyloxy, heterocycloalkyloxy, aryloxy, heteroaryloxy, arylalkyloxy, amino, alkylamino, aminoalkyl, acylamino, arylamino, phenoxy, benzyloxy, COOH, alkoxycarbonyl, alkylaminocarbonyl, sulfonyl, alkylsulfonyl, alkylsulfinyl, arylsulfonyl, arylsulfinyl, aminosulfonyl, $SR^6$ and acyl, each of which may be unsubstituted or substituted with one or more substituents independently selected from the group consisting of: halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH, —$COR^5$, —C(O)$OR^5$, —SH, —$SR^6$—$OR^6$ and acyl;

or $R^2$=L;

$R^3$ is selected from the group consisting of H, $C_1$-$C_6$ alkyl, and acyl; or a metal ion selected from sodium, calcium, magnesium;

X and Y are the same or different and are independently selected from the group consisting of: H, halogen, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH —C(O)$OR^5$, —$COR^5$, —SH, —$SR^6$, acyl and —$NR^7R^8$;

$R^4$ is selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl;

Each $R_5$ is independently selected from the group consisting of: alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl;

Each $R^6$ is independently selected from the group consisting of: alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl;

Each $R^7$ and $R^8$ are each independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl;

L is selected from the group consisting of:
a) L=Cy-$L^1$-W—

Wherein

Cy is $C_1$-$C_{15}$ alkyl, aminoalkyl, heterocycloalkyl, cycloalkyl, aryl, aryloxy or heteroaryl any of which may be optionally substituted one or more substituents independently selected from the group consisting of: halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH, —C(O)$OR^5$, —$COR^5$, —SH, —$SR^6$, —$OR^6$ and acyl.

$L^1$ is selected from the group consisting of $C_1$-$C_5$ alkyl, which may be optionally substituted with one or more substituents independently selected from the group consisting of: halogen; =O; =S; —CN; —$NO_2$; alkyl, alkoxy, acylamino, and alkylamino;

W is selected from the group consisting of a single bond, —O—, —S—, —S(O)—, —S(O)$_2$—, —N(R)— —C(O)N($R^9$)—, —SO$_2$N($R^9$)—, N($R^9$)C(O)—, N($R^9$)SO$_2$—, and —N($R^9$)—C(O)—N($R^{10}$)—;

b) L=Cy-$L^1$-W-$L^2$

Wherein,

Cy is $C_1$-$C_{15}$ alkyl, aminoalkyl, heterocycloalkyl, cycloalkyl, aryl, aryloxy or heteroaryl any of which may be optionally substituted one or more substituents independently selected from the group consisting of: halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH, C(O)$OR^6$, —$COR^5$, —SH, —$SR^6$, —$OR^6$ and acyl;

$L^1$ and $L^2$ are the same or different and independently $C_1$-$C_5$ alkyl, which may be optionally substituted with one or more substituents independently selected from the group consisting of: halogen; =O; =S; —CN; —$NO_2$; —$CF_3$, —$OCF_3$, alkyl, alkoxy, acylamino and alkylamino;

W is selected from the group consisting of a single bond, —O—, —S—, —S(O)—, —S(O)$_2$—, —N($R^9$)—, —C(O)N($R^9$)—, —SO$_2$N($R^9$)—, N($R^9$)C(O)—, N($R^9$)SO$_2$—, and —N($R^9$)—C(O)—N($R^{10}$)—;

c) L=Cy-(CH$_2$)m-W—

Wherein,

Cy is $C_1$-$C_{15}$ alkyl, aminoalkyl, heterocycloalkyl, cycloalkyl, aryl, aryloxy or heteroaryl, any of which may be optionally substituted one or more substituents independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, alkoxyalky, —COOH, C(O)OR$^6$, —COR$^5$, —SH, —SR$^6$, —OR$^6$ and acyl;

m is 0, 1, 2, 3, 4 or 5;

W is selected from the group consisting of a single bond, —O—, —S—, —S(O)—, —S(O)$_2$—, —N(R$^9$)—, —C(O)N(R$^9$)—, —SO$_2$N(R$^9$)—, N(R$^9$)C(O)—, N(R$^9$)SO$_2$—, and —N(R$^9$)—C(O)—N(R$^{10}$)—;

d) L=L$^1$-W-L$^2$

L$^1$ and L$^2$ are the same or different and independently selected from C$_1$-C$_5$ alkyl, which may be optionally substituted one or more substituents independently selected from the group consisting of: halogen; =O; =S; —CN; —NO$_2$; —CF$_3$, —OCF$_3$, alkyl, alkoxy, acylamino, alkylamino;

W is selected from the group consisting of a single bond, —O—, —S—, —S(O)—, —S(O)$_2$—, —N(R$^9$)—, —C(O)N(R$^9$)—, —SO$_2$N(R$^9$)—, N(R$^9$)C(O)—, N(R$^9$)SO$_2$—, and —N(R$^9$)—C(O)—N(R$^{10}$)—;

R$^9$ and R$^{10}$ are the same or different and are independently selected from H, C$_1$-C$_6$ alkyl, C$_4$-C$_9$ cycloalkyl, C$_4$-C$_9$ heterocycloalkyl, aryl, heteroaryl, arylalkyl, heteroarylalkyl; and acyl;

Z is a single bond or is selected from —CH$_2$—, —CH$_2$CH$_2$—, —CH=CH—, C$_3$-C$_6$ cycloalkyl, unsubstituted or substituted with one or more substituents independently selected from the group consisting of C$_1$-C$_4$ alkyl;

or a pharmaceutically acceptable salt thereof.

As used herein, the term unsubstituted means that there is no substituent or that the only substituents are hydrogen.

"Halogen" represents chlorine, fluorine, bromine or iodine.

"Alkyl" as a group or part of a group refers to a straight or branched aliphatic hydrocarbon group, preferably a C$_1$-C$_{14}$ alkyl, more preferably C$_1$-C$_{10}$ alkyl, most preferably C$_1$-C$_6$ unless otherwise noted. Examples of suitable straight and branched C$_1$-C$_6$ alkyl substituents include methyl, ethyl, n-propyl, 2-propyl, n-butyl, sec-butyl, t-butyl, hexyl, and the like.

"Alkylamino" includes both monoalkylamino and dialkylamino, unless specified. "Monoalkylamino" means a —NH-Alkyl group, "Dialkylamino" means a —N(alkyl)$_2$ group, in which the alkyl is as defined as above. The alkyl group is preferably a C$_1$-C$_6$ alkyl group.

"Arylamino" includes both mono-arylamino and di-arylamino unless specified. Mono-arylamino means a group of formula aryl NH—, di-arylamino means a group of formula (aryl$_2$)N— where aryl is as defined herein.

"Acyl" means an alkyl-CO— group in which the alkyl group is as described herein. Examples of acyl include acetyl and benzoyl. The alkyl group is preferably a C$_1$-C$_6$ alkyl group.

"Alkenyl" as group or part of a group denotes an aliphatic hydrocarbon group containing at least one carbon-carbon double bond and which may be straight or branched preferably having 2-14 carbon atoms, more preferably 2-12 carbon atoms, most preferably 2-6 carbon atoms, in the chain. The group may contain a plurality of double bonds in the normal chain and the orientation about each is independently E or Z. Exemplary alkenyl group include, but are not limited to, ethenyl and propenyl.

"Alkoxy" refers to an —O-alkyl group in which alkyl is defined herein. Preferably the alkoxy is a C$_1$-C$_6$alkoxy. Examples include, but are not limited to, methoxy and ethoxy.

"Alkenyloxy" refers to an —O— alkenyl group in which alkenyl is as defined herein. Preferred alkenyloxy groups are C$_1$-C$_6$ alkenyloxy groups.

"Alkynyloxy" refers to an —O-alkynyl group in which alkynyl is as defined herein. Preferred alkynyloxy groups are C$_1$-C$_6$ alkynyloxy groups.

"Alkoxycarbonyl" refers to an —C(O)—O-alkyl group in which alkyl is as defined herein. The alkyl group is preferably a C$_1$-C$_6$ alkyl group. Examples include, but not limited to, methoxycarbonyl and ethoxycarbonyl.

"Akylsulfinyl" means a —S(O)-alkyl group in which alkyl is as defined above. The alkyl group is preferably a C$_1$-C$_6$ alkyl group. Exemplary alkylsulfinyl groups include, but not limited to, methylsulfinyl and ethylsulfinyl.

"Alkylsulfonyl" refers to a —S(O)$_2$-alkyl group in which alkyl is as defined above. The alkyl group is preferably a C$_1$-C$_6$ alkyl group. Examples include, but not limited to methylsulfonyl and ethylsulfonyl.

"Alkynyl as a group or part of a group means an aliphatic hydrocarbon group containing a carbon-carbon trip bond and which may be straight or branched preferably having from 2-14 carbon atoms, more preferably 2-12 carbon atoms in the chain, preferably 2-6 carbon atoms in the chain. Exemplary structures include, but not limited to, ethynyl and propynyl.

"Alkylaminocarbonyl" refers to an alkylamino-carbonyl group in which alkylamino is as defined above.

"Cycloalkyl" refers to a saturated or partially saturated, monocyclic or fused or spiro polycyclic, carbocycle preferably containing from 3 to 9 carbons per ring, such as cyclopropyl, cyclobutyl, cyclopentyl, cyclohexyl and the like, unless otherwise specified.

The above discussion of alkyl and cycloalkyl substituents also applies to the alkyl portions of other substituents, such as without limitation, alkoxy, alkyl amines, alkyl ketones, arylalkyl, heteroarylalkyl, alkylsulfonyl and alkyl ester substituents and the like.

"Cycloalkylalkyl" means a cycloalkyl-alkyl- group in which the cycloalkyl and alkyl moieties are as previously described. Exemplary monocycloalkylalkyl groups include cyclopropylmethyl, cyclopentylmethyl, cyclohexylmethyl and cylcoheptylmethyl.

"Heterocycloalkyl" refers to an ring containing from at least one heteroatom selected from nitrogen, sulfur, oxygen, preferably from 1 to 3 heteroatoms. Each ring is preferably from 3 to 4 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane.

"Heterocycloalkenyl" refers to a heterocycloalkyl as described above but containing at least one double bond.

"Heterocycloalkylalkyl" refers to a heterocycloalkyl-alkyl group in which the heterocycloalkyl and alkyl moieties are as previously described. Exemplary heterocycloalkylalkyl groups include (2-tetrahydrofuryl)methyl, (2-tetrahydrothiofuranyl)methyl.

"Heteroalkyl" refers to a straight- or branched-chain alkyl group preferably having from 2 to 14 carbons, more preferably 2 to 10 atoms in the chain, one or more of which is a heteroatom selected from S, O, and N. Exemplary heteroalkyls include alkyl ethers, secondary and tertiary alkyl amines, alkyl sulfides, and the like.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The aryl group may be substituted by one or more substituent groups.

"Arylalkenyl" means an aryl-alkenyl- group in which the aryl and alkenyl are as previously described. Exemplary arylalkenyl groups include phenylallyl.

"Arylalkyl" means an aryl-alkyl group in which the aryl and alkyl moieties are as previously described. Preferred arylalkyl groups contains a $C_{1-5}$ alkyl moiety. Exemplary arylalkyl groups include benzyl, phenethyl and naphthelenemethyl.

"Cycloalkenyl" means an optionally substituted non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups.

"Heteroaryl" refers to a monocyclic, or fused polycyclic, aromatic heterocycle (ring structure preferably having a 5 to 7 member aromatic ring containing one or more heteroatoms selected from N, O and S). Typical heteroaryl substituents include furyl, thienyl, pyrrole, pyrazole, triazole, thiazole, oxazole, pyridine, pyrimidine, isoxazolyl, pyrazine, indole, benzimidazole, and the like.

"Heteroarylalkyl" means a heteroaryl-alkyl group in which the heteroaryl and alkyl moieties are as previously described. Preferred heteroarylalkyl groups contain a lower alkyl moiety. Exemplary heteroarylalkyl groups include pyridylmethyl.

"Lower alkyl" as a group means unless otherwise specified, an aliphatic hydrocarbon group which may be straight or branched having 1 to 6 carbon atoms in the chain, more preferably 1 to 4 carbons such as methyl, ethyl, propyl (n-propyl or isopropyl) or butyl (n-butyl, isobutyl or tertiary-butyl).

In Formula I, as well as in Formulae Ia-Ib defining sub-sets of compounds within Formula I, there is shown a benzimidazole ring system. Within this ring system, there are substitutable positions at the 4-, 5-, 6-, and 7-ring positions. In each of Formulae I, Ia, and Ib, there is a requirement for attachment of an acidic moiety at one of the ring positions. This acidic moiety may be provided by but is not limited to groups containing, a hydroxamic acid or salt derivatives of such acid which when hydrolyzed would provide the acidic moiety. In some embodiments the acidic moiety may be attached to the ring position through an alkylene group such as —$CH_2$— or —$CH_2CH_2$—, or an alkenyl group such as —CH=CH—. Preferred positions for attachment of the acidic moiety are the 5- and 6-ring positions.

It is understood that included in the family of compounds of Formula I are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art.

Some of the compounds of the disclosed embodiments may exist as single stereoisomers, racemates, and/or mixtures of enantiomers and/or diastereomers. All such single stereoisomers, racemates and mixtures thereof are intended to be within the scope of the subject matter described and claimed.

Additionally, Formula I is intended to cover, where applicable, solvated as well as unsolvated forms of the compounds. Thus, each formula includes compounds having the indicated structure, including the hydrated as well as the non-hydrated forms.

In addition to compounds of the Formula I, the HDAC inhibiting agents of the various embodiments include pharmaceutically acceptable salts, prodrugs, and active metabolites of such compounds, and pharmaceutically acceptable salts of such metabolites.

The term "Pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula I may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Suitable pharmaceutically acceptable base addition salts of compounds of Formula I include metallic salts made from lithium, sodium, potassium, magnesium, calcium, aluminium, and zinc, and organic salts made from organic bases such as choline, diethanolamine, morpholine. Other examples of organic salts are: ammonium salts, quaternary salts such as tetramethylammonium salt; amino acid addition salts such as salts with glycine and arginine. Additional information on pharmaceutically acceptable salts can be found in Remington's Pharmaceutical Sciences, 18th Edition, Mack Publishing Co., Easton, Pa. 1990. In the case of agents that are solids, it is understood by those skilled in the art that the inventive compounds, agents and salts may exist in different crystalline or polymorphic forms, all of which are intended to be within the scope of the present invention and specified formulae.

"Prodrug" means a compound which is convertible in vivo by metabolic means (e.g. by hydrolysis, reduction or oxidation) to a compound of formula I. For example an ester prodrug of a compound of formula I containing a hydroxyl group may be convertible by hydrolysis in vivo to the parent molecule. Suitable esters of compounds of formula (I) containing a hydroxyl group, are for example acetates, citrates, lactates, tartrates, malonates, oxalates, salicylates, propionates, succinates, fumarates, maleates, methylene-bis-β-hydroxynaphthoates, gestates, isethionates, di-p-toluoyltartrates, methanesulphonates, ethanesulphonates, benzenesulphonates, p-toluenesulphonates, cyclohexylsulphamates and quinates. As another example an ester prodrug of a compound of formula I containing a carboxy group may be convertible by hydrolysis in vivo to the parent molecule. (Examples of ester prodrugs are those described by F. J. Leinweber, Drug Metab. Res., 18:379, 1987).

Possible HDAC inhibiting agents include those having an IC50 value of 1 μM or less.

Administration of compounds within Formula I to humans can be by any of the accepted modes for enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the patient a therapeutically effective dose. In various embodiments the inhibitor compound may be selectively toxic or more toxic to rapidly proliferating cells, e.g. cancerous tumors, than to normal cells.

The term "therapeutically effective amount" or "therapeutic amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

In using the compounds of the invention they can be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances. We refer the reader to Remingtons Pharmaceutical Sciences, 18$^{th}$ edition, Mach Publishing Co. (1990) for further information.

The compounds of the present invention can be administered alone or in the form of a pharmaceutical composition in combination with a pharmaceutically acceptable carrier, diluent or excipient. The compounds of the invention, while effective themselves, are typically formulated and administered in the form of their pharmaceutically acceptable salts as these forms are typically more stable, more easily crystallised and have increased solubility.

The compounds are, however, typically used in the form of pharmaceutical compositions which are formulated depending on the desired mode of administration. As such in a further embodiment the present invention provides a pharmaceutical composition including a compound of Formula (I) and a pharmaceutically acceptable carrier, diluent or excipient. The compositions are prepared in manners well known in the art.

The compounds of the invention may be used or administered in combination with one or more additional drug (s) that are chemotherapeutic drugs or HDAC inhibitor drugs and/or procedures (e.g. surgery, radiotherapy) for the treatment of the disorder/diseases mentioned. The components can be administered in the same formulation or in separate formulations. If administered in separate formulations the compounds of the invention may be administered sequentially or simultaneously with the other drug(s).

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

If desired, and for more effective distribution, the compounds can be incorporated into slow release or targeted delivery systems such as polymer matrices, liposomes, and microspheres.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, patches, sprays, ointments and inhalants. The active compound is mixed under sterile conditions with a pharmaceutically acceptable carrier and any needed preservatives, buffers, or propellants which may be required.

A preferred dosage will be a range from about 0.01 to 300 mg per kilogram of body weight per day. A more preferred dosage will be in the range from 0.1 to 100 mg per kilogram of body weight per day, more preferably from 0.2 to 80 mg per kilogram of body weight per day, even more preferably 0.2 to 50 mg per kilogram of body weight per day. A suitable dose can be administered in multiple sub-doses per day.

As discussed above, the compounds of the embodiments disclosed inhibit histone deacetylases. The enzymatic activity of a histone deacetylase can be measured using known methodologies [Yoshida M. et al, J. Biol. Chem., 265, 17174 (1990), J. Taunton et al, Science 1996 272: 408]. In certain embodiments, the histone deacetylase inhibitor interacts with and reduces the activity of more than one known histone deacetylase in the cell. In some other embodiments, the histone deacetylase inhibitor interacts and reduces the activity of predominantly one histone deacetylase, for example HDAC-1, HDAC-3 or HDAC-8 which belongs to Class I HDAC enzymes [De Ruijter A. J. M. et al, Biochem. J., 370, 737-749 (2003)]. Certain preferred histone deacetylase inhibitors are those that interact with, and reduce the activity of a histone deacetylase which is involved in tumorigenesis, and these compounds may be useful for treating proliferative diseases. Examples of such cell proliferative diseases or conditions include cancer and/or any metastases, psoriasis, and restenosis. The inventive compounds may be particularly useful for treating tumors such as breast cancer, lung cancer, ovarian cancer, prostate is cancer, head and/or neck cancer, or renal, gastric, and brain cancer. In addition, the inventive compounds may be useful for treating a proliferative disease that is refractory to the treatment with other chemotherapeutics; and for treating hyperproliferative condition such as leukemias, psoriasis, restenosis.

Additionally compounds of the various embodiments disclosed herein may be useful for treating neurodegenerative diseases, and inflammatory diseases and/or immune system disorders.

The disorder is preferably selected from the group consisting of cancer, inflammatory diseases and/or immune system disorders (e.g. rheumatoid arthritis, systemic lupus erythematosus), angiofibroma, cardiovascular diseases, fibrotic diseases, diabetes, autoimmune diseases, chronic and acute neurodegenerative disease like Huntington's disease, Parkinson's disease, disruptions of nerval tissue and infectious diseases like fungal, bacterial and viral infections. In another embodiment the disorder is a proliferative disorder.

The histone deacetylase inhibitors of the invention have significant antiproliferative effects and promote differentiation, cell cycle arrest in the G1 or G2 phase, and apoptosis.

Synthesis of Deacetylase Inhibitors

The agents of the various embodiments may be prepared using the reaction routes and synthesis schemes as described below, employing the techniques available in the art using starting materials that are readily available. The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, John Wiley & Sons, 1981. Alternatively, other reactions disclosed herein or known in the art will be recognized as having applicability for preparing other compounds of the various embodiments.

Reagents useful for synthesizing compounds may be obtained or prepared according to techniques known in the art.

In the examples described below, unless otherwise indicated, all temperatures in the following description are in degrees Celsius and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. Tetrahydrofuran (THF) and N,N-dimethylformamide (DMF) were purchased from Aldrich in SureSeal bottles and used as received. All solvents were purified by using standard methods in the art, unless otherwise indicated.

The reactions set forth below were performed under a positive pressure of nitrogen, argon or with a drying tube, at ambient temperature (unless otherwise stated), in anhydrous solvents, and the reaction flasks are fitted with rubber septa for the introduction of substrates and reagents via syringe. Glassware was oven-dried and/or heat-dried. Analytical thin-layer chromatography was performed on glass-backed silica gel 60 F 254 plates (E Merck (0.25 mm)) and eluted with the appropriate solvent ratios (v/v). The reactions were assayed by TLC and terminated as judged by the consumption of starting material.

The TLC plates were visualized by UV absorption or with a p-anisaldehyde spray reagent or a phosphomolybdic acid reagent (Aldrich Chemical, 20 wt % in ethanol) which was activated with heat, or by staining in iodine chamber. Workups were typically done by doubling the reaction volume with the reaction solvent or extraction solvent and then washing with the indicated aqueous solutions using 25% by volume of the extraction volume (unless otherwise indicated). Product solutions were dried over anhydrous sodium sulfate prior to filtration, and evaporation of the solvents was under reduced pressure on a rotary evaporator and noted as solvents removed in vacuo. Flash column chromatography [Still et al, J. Org. Chem., 43, 2923 (1978)] was conducted using E Merck-grade flash silica gel (47-61 mm) and a silica gel:crude material ratio of about 20:1 to 50:1, unless otherwise stated. Hydrogenolysis was done at the pressure indicated or at ambient pressure.

1H NMR spectra was recorded on a Bruker instrument operating at 400 MHz, and $^{13}$C—NMR spectra was recorded operating at 100 MHz. NMR spectra are obtained as $CDCl_3$ solutions (reported in ppm), using chloroform as the reference standard (7.25 ppm and 77.00 ppm) or $CD_3OD$ (3.4 and 4.8 ppm and 49.3 ppm), or an internal tetramethylsilane standard (0.00 ppm) when appropriate. Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Mass spectra were obtained using LC/MS either in ESI or APCI. All melting points are uncorrected.

All final products had greater than 90% purity (by HPLC at wavelengths of 220 nm and 254 nm).

The following examples are intended to illustrate the embodiments disclosed and are not to be construed as being limitations thereto. Additional compounds, other than those described below, may be prepared using the following described reaction scheme or appropriate variations or modifications thereof.

Synthesis

Scheme I illustrates the procedure used for preparing compounds of formula Ib, wherein X and Y are hydrogens, compounds (VI) of formula Ia can be prepared by analogous procedure, for example, by the choice of appropriate starting material. For example, in the case of Z is —CH=CH— and attached to $C_5$-position in Formula Ib, such compound(s) can be synthesized by analogous method illustrated in Scheme I starting with a substituted cinnamic acid (e.g. trans-3-nitro-4-chloro-cinnamic acid), appropriate amine component ($R^1NH_2$), aldehyde or carboxylic acid component ($R^2CHO$ or $R^2COOH$), and appropriate hydroxylamine or N-alkyl hydroxylamine ($NHR^3OH$ where $R^3$ is defined as above in Formula Ia).

Specifically, the hydroxamate compounds Formula Ib can be synthesized by the synthetic route shown in Scheme I. The reaction of trans-4-chloro-3-nitrocinnamic acid (I) with an amine in the present of a base (e.g. triethylamine) in an appropriate solvent (e.g. dioxane) gave (II). Treatment of (II) in methanol under acid catalysis (e.g. sulfuric acid) resulted in esterification providing (III). The nitro group of (III) can be reduced by appropriate reducing agent (e.g. tin chloride) and the resulting phenylenediamine was cyclized with an aldehyde to give (V). The hydroxamate compounds (VI) were obtained by a known synthesis method (J. Med. Chem., 2002, 45, 753-757). An alternative method for preparation of (VI) is by coupling (IV) with an appropriate acid and then cyclized by heating with acetic acid (J. Med. Chem. 2001, 44, 1516-1529).

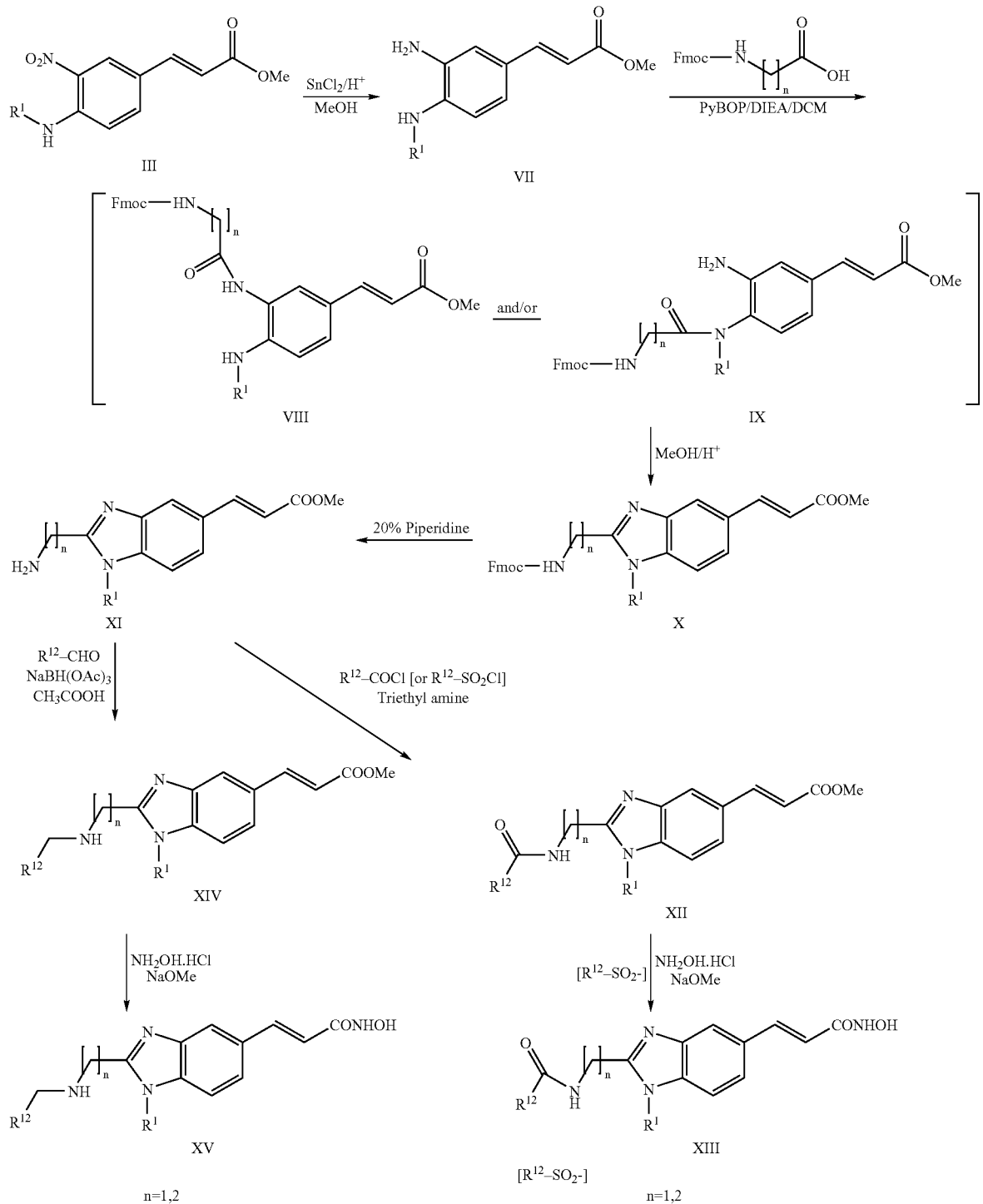

Scheme II illustrates another alternative procedure used for preparing compounds of formula Ib, where X and Y are hydrogens, $R^2$=Cy-$L^1$-W-$L^2$. For example, in the case of Z is —CH=CH— and attached to $C_5$-position in Formula Ib, such compound(s) (XV) can be synthesized by analogous method illustrated in Scheme II starting with appropriate (III), appropriate Fmoc protected amino acids, appropriate acid chlorides or aldehydes, and hydroxylamine.

More specifically, for example, the hydroxamate compounds Formula Ib, where X and Y are hydrogens, $R^2$=Cy-$L^1$-W-$L^2$ and Z is attached to $C_5$-position, can be synthesized by the synthetic route shown in Scheme II. Appropriate intermediates (III) were reduced with Tin chloride to the corresponding diamines (VII). The coupling reaction with appropriate Fmoc protected amino acids in the presence of PyBOP gave two coupling products (VII) and (IX). Without further separation, (VIII) and (IX) were subjected to cyclization under acid conditions and yielded (X). The key intermediate (XI) can be obtained by treating (X) with 20% piperidine. Treatment of (XI) with an appropriate acid chloride or an appropriate sulfonyl chloride gave (XII) and the target compounds (XIII) were obtained by using similar method described above.

When (XI) was reacted with an appropriate aldehyde under reduction conditions (NaBH(OAc)$_3$/CH$_3$COOH), (XIV) was obtained and can be transformed to corresponding hydroxamate derivatives (XV) by the same methods described above.

C$_5$-position, in Formula Ib, such compound(s) (VI) can be synthesized by analogous method illustrated in Scheme III starting with SASRIN resin, an appropriate hydroxylamine (e.g., O-(2,4-dimethoxy-phenyl)-hydroxylamine), an appropriate cinnamic acid (e.g., trans-4-chloro-3-nitro-cinnamic acid), an appropriate amine and an aldehyde.

Specifically, for example, the hydroxamate compounds (VI) Formula Ib can be synthesized by the synthetic route shown in Scheme IV. The SASRIN resin was treated with O-(2,4-dimethoxy-phenyl)-hydroxylamine under reductive conditions (NaBH$_3$CN/CH$_3$COOH) in an appropriate solvent gave corresponding compound (XVI). (XVI) was reacted with trans-4-chloro-3-nitro-cinnamic acid in the presence of 4-dimethylaminopyridine to yield (XVII). Further treatment of (XVII) with appropriate amines yielded (XVIII). (XIX)

Scheme III

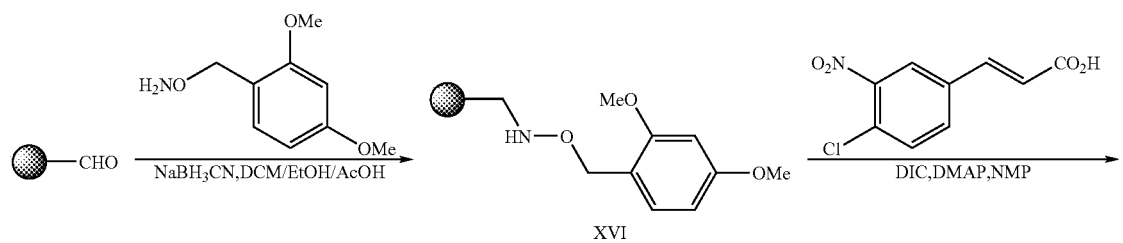

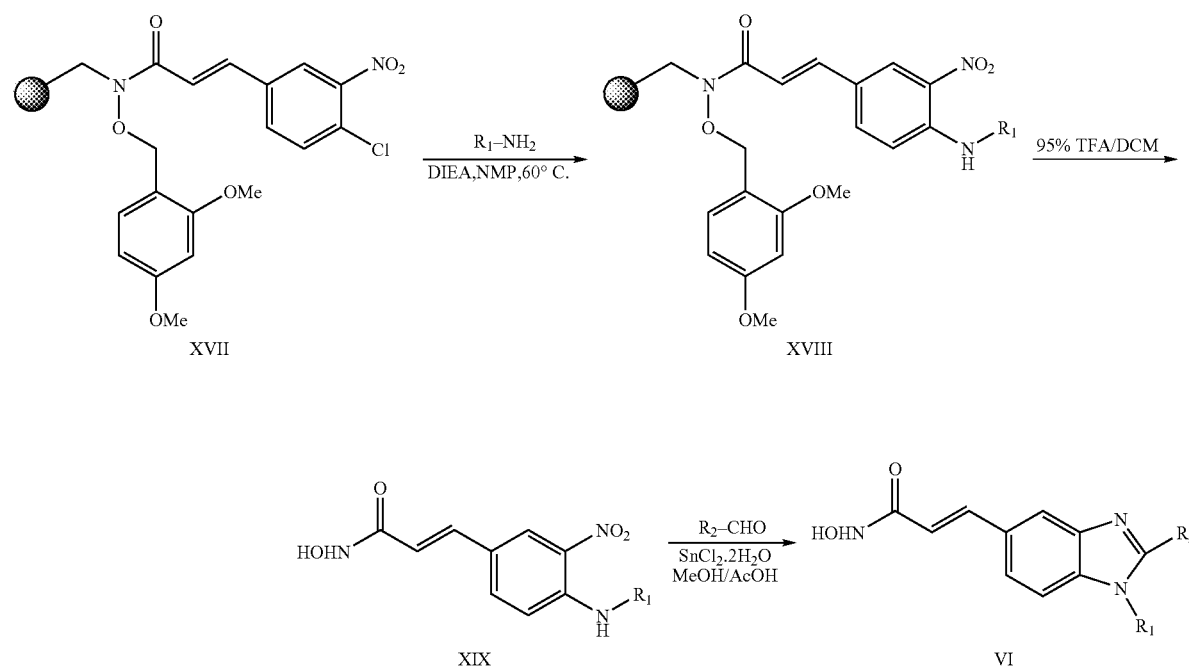

Hydroxamate compounds of Formula I can also be prepared through solid phase synthesis. Scheme III illustrates the synthesis of hydroxamate compounds of Formula Ib. For example, in the case of Z is —CH═CH— and attached to was obtained by cleavage of the corresponding resin (XVIII). Without further purification, (XIX) was transformed to the corresponding hydroxamate compounds (VI) using the method described above.

Scheme IV

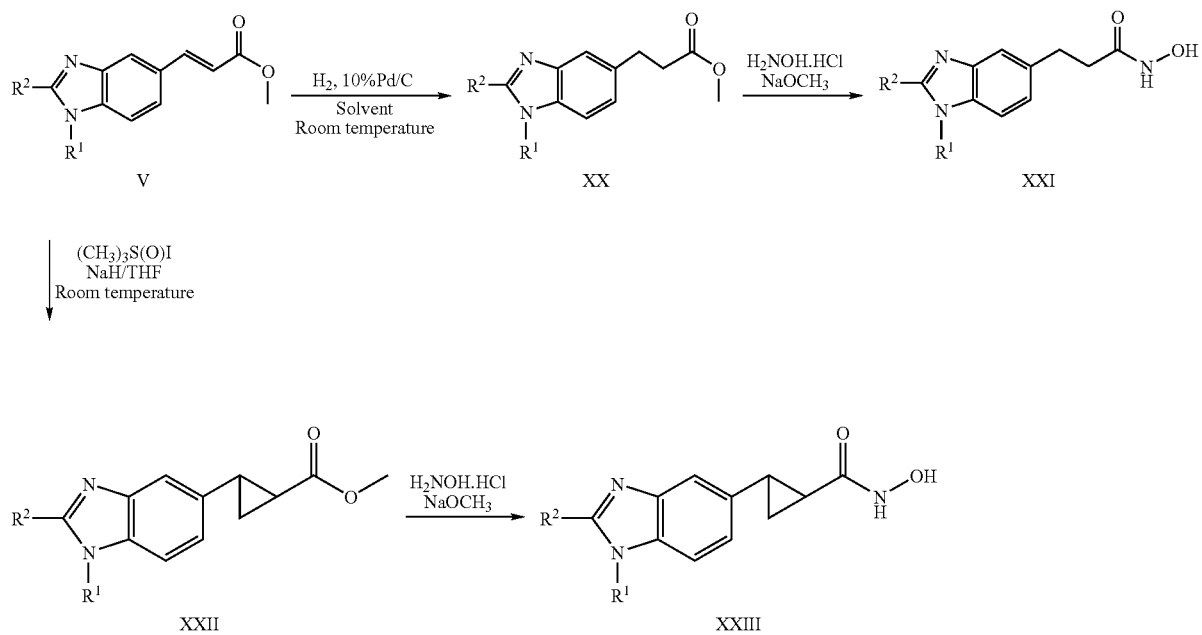

Scheme IV illustrates another procedure for the preparation of hydroxamate compounds of Formula I. For example, in the case of Z is —CH₂CH₂— and attached to C₅-position in Formula Ib, such compound(s) can be synthesized by analogous method illustrated in Scheme IV starting with appropriate intermediates (V) through reduction and then the resulting product (XX) can be transformed into corresponding hydroxamate compounds (XXI) of Formula Ib. Compounds (XXIII) in which Z is a cyclopropylene group

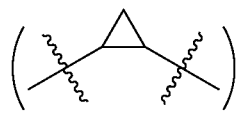

and attached to C₅-position in Formula Ib, can be prepared from V by treating with (CH₃)₃S(O)I, and the resulting cyclopropyl derivatives (XXII) was converted to corresponding hydroxamate derivatives (XXIII) according to methods described above for the preparation of hydroxamic acid.

Scheme V

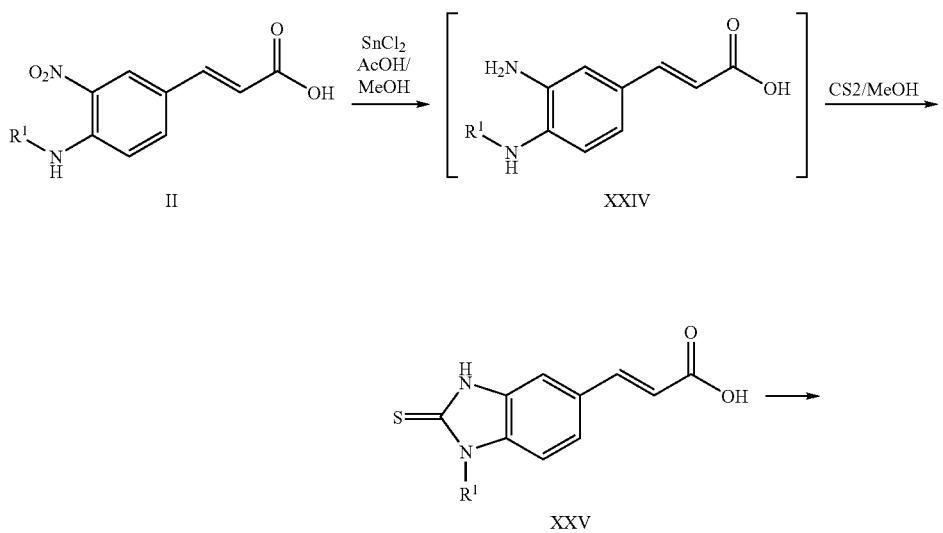

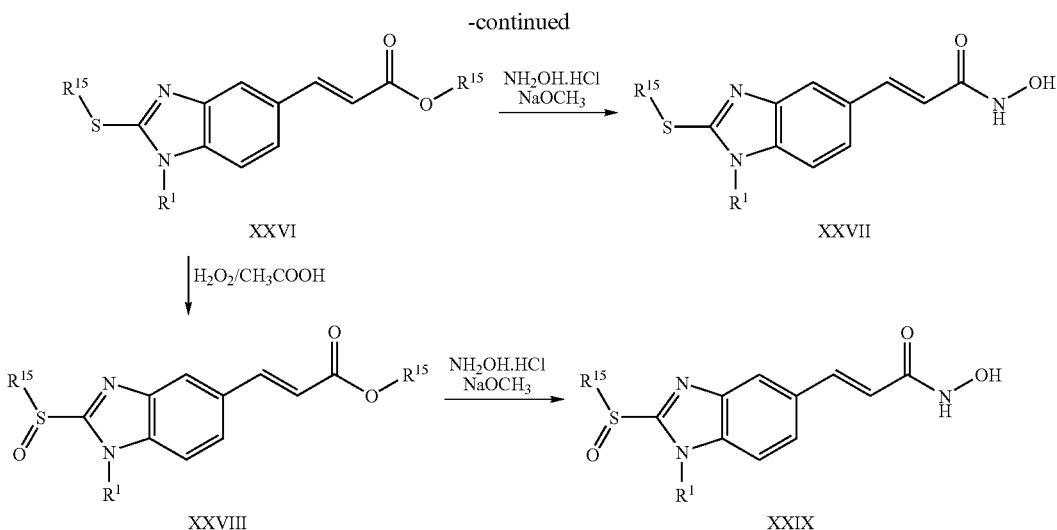

Scheme V illustrates another synthetic procedure of hydroxamate compounds of Formula I. For example, in the case of Z is —CH=CH— and attached to $C_5$-position in Formula Ib, such compound(s) can be synthesized by analogous method illustrated in Scheme V starting with appropriate intermediates (II) through reduction and then the resulting product (XXIV) was, without further purification, cyclized to give (XXV). (XXV) was treated with an appropriate alkyl halide (e.g., benzyl bromide) in the presence of an inorganic base (e.g., sodium carbonate) in an appropriate solvent to give (XXVI). Treatment of (XXVI) with hydrogen peroxide in acetic acid led to (XXVIII). Using the same method described previously, both (XXVI) and (XXVIII) were transformed into corresponding hydroxamate compounds (XXVII), and (XXIX), respectively.

The following preparation and examples are given to enable those skilled in the art to more clearly understand and to practice the subject matter hereof. They should not be considered as limiting the scope of the disclosure, but merely as being illustrative and representative thereof.

EXAMPLE 1

Preparation of N-Hydroxy-3-[1-(3-hydroxy-propyl)-2-(2-phenyl-propyl)-1H-benzimidazol-5-yl]-acrylamide (1)

Step 1

To a pre-stirred solution of trans-4-chloro-3-nitrocinnamic acid (1.0 g, 4.4 mmol) in dioxane (10 mL) was added triethylamine (2 mL), 3-amino-1-propanol (1.5 mL). The resulting solution was heated to 85° C. for 19 hours and then cooled to room temperature. The solvent was removed under vacuum. Water (100 mL) was added to the residue and the pH was adjusted to 1-1.5. The precipitate was collected and washed with cold water for 2 times and dried. The product 3-[3-nitro-4-(hydroxypropylamine)-phenyl]-acrylic acid was obtained as yellow solid (1.10 g, 95%). MS(m/z): 267 $(MH)^+$.

Step 2

Concentrated sulfuric acid (0.5 mL) was added to the solution of trans-4-(3-hydroxypropylamine)-3-nitrocinnamic acid, (1.10 g, 3.9 mmol) and MeOH (15 mL). The resulting solution was heated to reflux for 18 hours. The reaction mixture was cooled at −10° to −15° C. for 3 hours. 3-[3-nitro-4-(hydroxypropylamine)-phenyl]-acrylic acid methyl ester was collected as crystalline yellow solid (1.06 g, 91%). MS(m/z): 281 $(MH)^+$.

Step 3

To a pre-stirred solution of methyl trans-4-(3-hydroxypropylamine)-3-nitrocinnamate (280 mg, 1.0 mmol) and 3-phenylbutyraldehyde (500 mg, 3.4 mmol) in glacial acetic acid (5 mL), Tin chloride was added (1.18 g, 10.0 mmol). The resulting solution was heated to 45° C. for 17 hours and then cooled to room temperature. The solvent was removed under vacuum. Water (20 mL) and dichloromethane (20 mL) was added to the residue and stirred for 30 minutes. The organic layer was dried ($MgSO_4$), filtered and concentrated to an oily residue. 100 mL diethyl ether was added and stirred for 4 hours. The product 3-[1-(3-Hydroxy-propyl)-2-(2-phenyl-propyl)-1H-benzimidazol-5-yl]-acrylic acid methyl ester was obtained in 34.9% yield (132.0 mg). MS(m/z): 379 $(MH)^+$.

Step 4

Sodium methoxide (30% in methanol) (782 mg, 4.1 mmol) was added to a prestirred solution of 3-[1-(3-Hydroxy-propyl)-2-(2-phenyl-propyl)-1H-benzimidazol-5-yl]-acrylic acid methyl ester (130 mg, 0.34 mmol and hydroxylamine hydrochloride (242 mg, 3.4 mmol in MeOH (1.5 mL). The reaction mixture was continuously stirred for 40 minutes at room temperature and then poured into a solution of ice-water containing 1.0 mL concentrated hydrochloric acid. The mixture was extracted with dichloromethane. The organic layer was dried ($MgSO_4$), filtered and concentrated. The desired product was separated by reverse phase preparative HPLC. After lyopholyzation, 7.8 mg (6%) of N-Hydroxy-3-[1-(3-hydroxy-propyl)-2-(2-phenyl-propyl)-1H-benzimidazol-5-yl]-acrylamide was obtained as powder. HPLC: 96%; $t_R$= (LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 7.22 min; 92%. $^1H$ NMR (400 MHz, DMSO-$d_6$) δ 1.35 (3H, d, J=6.5 Hz), 1.83 (2H, m), 3.00-4.00 (6H, m), 4.33 (2H, t, J=7.1 Hz), 6.55 (1H, d, J=15.8 Hz), 7.19-7.33 (5H, m), 7.62 (1H, d, J=15.8 Hz), 7.70 (1H, d, J=8.60 Hz), 7.82 (1H, d, J=8.60 Hz), 7.92 (1H, s), 10.15 (1H, bs), 10.33 (1H, bs). MS(m/z): 380 [MH]+.

EXAMPLE 2

Preparation of N-Hydroxy-3-[1-(3,4,5-trimethoxy-benzyl)-2-(2-phenyl-ethyl)-1H-benzimidazol-5-yl]-acrylamide (2)

The titled compound (2) was prepared according to the procedures described in Example 1, by using appropriate starting materials. HPLC: 91%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 7.22 min. $^1$H NMR (400 MHz, DMSO-d$_6$) δ3.08 (2H, t, J=7.72 Hz), 3.48 (2H, t, 7.72 Hz), 3.63 (3H, s), 3.67 (6H, s), 5.58 (2H, s), 6.59 (2H, s), 7.22-7.31 (7H, m), 7.63 (1H, d, J=15.78 Hz), 7.71 (1H, d, J=8.76 Hz), 7.83 (1H, d, J=8.76 Hz), 7.98 (1H, s), 11.00 (2H, bs). MS(m/z): 488 [MH]+.

EXAMPLE 3

Preparation of N-Hydroxy-3-[2-(4-benzyloxy-3-methoxy-phenyl)-1-methyl-1H-benzimidazole-5-yl]-acrylamide (3)

The titled compound (3) was prepared according to the procedures described in Example 1, by using appropriate starting materials. HPLC: 92%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 7.32 min. $^1$H NMR (400 MHz, DMSO-d$_6$) δ 3.87 (3H, s), 4.01 (3H, s), 5.24 (2H, s), 6.56 (1H, d=15.80 Hz), 7.32-7.50 (8H, m), 7.74(1H, d, J=8.72 Hz), 7.88(1H, d, J=8.72 Hz), 7.94(1H, s), 10.85(1H, bs). MS (m/z): 431 [MH]+.

EXAMPLE 4

Preparation of N-Hydroxy-3-[2-(4-benzyloxy-3-methoxy-phenyl)-1-(3-hydroxy-propyl)-1H-benzimidazole-5-yl]-acrylamide (4)

The titled compound (4) was prepared according to the procedures described in Example 1, by using appropriate starting materials. HPLC: 95%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 6.82 min. $^1$H NMR (400 MHz, DMSO-d$_6$) δ 1.96 (2H, m), 3.88 (3H, s), 4.48 (2H, t, J=7.12 Hz), 5.24 (2H, s), 6.56 (1H, d, J=15.76 Hz), 7.32-7.50 (8H, m), 7.65 (1H, d, J=15.76 Hz), 7.74 (1H, d, J=8.60 Hz), 7.91 (1H, d, J=8.60 Hz), 7.95 (1H, s), 10.85 (1H, bs). MS (m/z): 474 [MH]+.

EXAMPLE 5

Preparation of N-Hydroxy-3-[1-(2-hydroxy-ethyl)-2-(4-methoxy-phenyl)-1H-benzimidazole-5-yl]-acrylamide (5)

The titled compound (5) was prepared according to the procedures described in Example 1, by using appropriate starting materials. HPLC: 98%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 4.12 min. $^1$H NMR (400 MHz, DMSO-d$_6$) δ 3.80 (2H, t, J=5.36 Hz), 3.87 (3H, s), 4.39 (2H, t, J=5.36 Hz), 6.56 (1H, d, 15.72 Hz), 7.17 (2H, d, J=8.88 Hz), 7.61 (1H, d, J=8.52 Hz), 7.62 (1H, d, J=15.72 Hz), 7.78 (1H, d, J=8.52 Hz), 7.88 (1H, d, J=8.88 Hz), 7.90 (1H, s), 10.77 (1H, bs). MS (m/z): 354 [MH]+.

EXAMPLE 6

Preparation of N-Hydroxy-3-[1-(2,3-hydroxy-propyl)-2-(4-methoxy-phenyl)-1H-benzimidazole-5-yl]-acrylamide (6)

The titled compound (6) was prepared according to the procedures described in Example 1, by using appropriate starting materials. HPLC: 98%, $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 3.39 min. NMR (400 MHz, DMSO-d$_6$) δ 3.90 (3H, s), 4.01 (1H, m), 4.35 (2H, m), 4.58 (2H, dd, J=2.48 and 14.48 Hz), 6.62 (1H, d, J=15.84 Hz), 7.27 (2H, d, J=8.92 Hz), 7.68 (1H, d, J=15.84 Hz), 8.01(4H, m), 10.13 (1H, bs). MS (m/z): 383 [M]+.

EXAMPLE 7

Preparation of N-Hydroxy-3-[2-(4-benzyloxy-3-methoxy-phenyl)-1-(2,3-hydroxy-propyl)-1H-benzimidazole-5-yl]-acrylamide (7)

The titled compound (7) was prepared according to the procedures described in Example 1, by using appropriate starting materials. HPLC: 100%, $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 2.06 min. NMR (400 MHz, DMSO-d$_6$) δ 4.04-4.38 (3H, m), 4.05 (3H, s), 4.49 (2H, m), 5.22 (2H, s), 6.55 (1H, d, J=15.72 Hz), 7.29-7.94 (11H, m), 8.01 (1H, s). MS (m/z): 490 [MH]+.

EXAMPLE 8

Preparation of N-Hydroxy-3-[1-(2,3-hydroxy-propyl)-2-(2-pyridyl)-1H-benzimidazol-5-yl]-acrylamide (9)

The titled compound (9) was prepared according to the procedures described in Example 1, by using appropriate starting materials. HPLC: 93.7%, $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 2.61 min. NMR (400 MHz, DMSO-d$_6$) δ 3.20-3.37 (4H, m), 3.90 (1H, m), 4.90-4.95 (2H, m), 6.54 (1H, d, J=15.52 Hz), 7.98 (1H, s), 8.04 (1H, m), 8.27 (1H, m), 9.73 (1H, d, J=8.0 Hz). MS (m/z): 355 [MH]+.

EXAMPLE 9

Preparation of N-Hydroxy-3-[1-(2-hydroxy-ethyl)-2-(4-pyridyl)-1H-benzimidazol-5-yl]-acrylamide (10)

The titled compound (10) was prepared according to the procedures described in Example 1, by using appropriate starting materials. HPLC: 97.0%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 1.14 min. NMR (400 MHz, DMSO-de) δ 3.78 (2H, t, J=5.80 Hz), 4.43 (2H, t, J=5.80 Hz), 6.50 (1H, d, J=15.80 Hz), 7.82 (2H, d, J=8.56 Hz), 7.94 (1H, s), 8.00 (2H, d, J=5.97 Hz), 8.81 (2H, d, J=5.97 Hz). MS (m/z): 325 [MH]$^+$.

EXAMPLE 10

Preparation of N-Hydroxy-3-[1-(3-hydroxy-propyl)-2-(4-pyridyl)-1H-benzimidazol-5-yl]-acrylamide (11)

The titled compound (11) was prepared according to the procedures described in Example 1, by using appropriate starting materials. HPLC: 98.2%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 2.61 min. NMR (400 MHz, DMSO-$d_6$) δ 1.91 (2H, m), 3.37 (2H, t, J=5.84 Hz), 4.49 (2H, t, J=7.84 Hz), 6.54 (1H, d, J=15.52 Hz), 7.98 (1H, s), 8.06 (2H, d, J=6.26 Hz), 8.90 (2H, d, J=626 Hz). MS (m/z): 339 [MH]$^+$.

EXAMPLE 11

Preparation of N-Hydroxy-3-[1-(3-pyridylmethyl)-2-(2-phenyl-ethyl)-1H-benzimidazol-5-yl]-acrylamide (12)

The titled compound (12) was prepared according to the procedures described in Example 1, by using appropriate starting materials. HPLC: 97.9%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 3.32 min. NMR (400 MHz, DMSO-$d_6$) δ 3.11 (2H, t, J=8.40 Hz), 5.71 (2H, s), 6.51 (1H, d, J=15.80 Hz), 7.20-7.31 (6H, m), 7.43 (1H, m), 7.40-7.57 (4H, m), 7.94 (1H, s), 8.57 (1H, s). MS (m/z): 399 [MH]$^+$.

EXAMPLE 12

Preparation of N-Hydroxy-3-[1-(3-hydroxy-propyl)-2-(2-pyridyl)-1H-benzimidazol-5-yl]-acrylamide (13)

The titled compound (13) was prepared according to the procedures described in Example 1, by using appropriate starting materials. HPLC: 98.3%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 3.37 min. NMR (400 MHz, DMSO-$d_6$) δ 1.98 (2H, m), 3.30 (2H, m), 4.86 (2H, t, J=7.00 Hz), 6.51 (1H, d, J=15.76 Hz), 7.77 (2H, d, J=8.56 Hz), 7.94 (1H, s), 8.05 (1H, m), 8.30 (1H, d, J=7.92 Hz), 8.78 (1H, d, J=4.28 Hz). MS (m/z): 339 [MH]$^+$.

EXAMPLE 13

Preparation of N-Hydroxy-3-[1-(3-hydroxy-propyl)-2-phenethyl-1H-benzimidazol-5-yl]-acrylamide (14)

The titled compound (14) was prepared according to the procedures described in Example 1, by using appropriate starting materials. HPLC: 97.3%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 2.63 min. NMR (400 MHz, DMSO-$d_6$) δ 1.87 (2H, m), 3.18 (2, t, J=7.40 Hz), 4.41 (2H, t, J=7.0 Hz), 6.57 (1H, d, J=17.60 Hz), 7.15 (5H, m), 7.64 (1, d, J=17.60 Hz), 7.89 (1H, d, J=8.64 Hz), 7.95 (1H, s). MS (m/z): 366 [MH]$^+$.

EXAMPLE 14

Preparation of N-Hydroxy-3-(2-phenethyl-1-(pyridin-2-yl)methyl-1H-benzimidazol-5-yl)-acrylamide (16)

The titled compound (16) was prepared according to the procedures described in Example 1, by using appropriate starting materials. HPLC: 99.7%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 3.11 min. NMR (400 MHz, DMSO-$d_6$) δ 3.31 (2H, t, J=7.56 Hz), 5.81 (2H, s), 6.57 (1H, d, J=17.60 Hz), 7.20-7.36 (6H, m), 7.52 (1H, m), 7.64 (1H, d, J=17.60 Hz), 7.68 (1H, d, J=8.48 Hz), 7.77 (1H, d, J=8.48 Hz), 7.87 (1H, m), 8.44 (1H, d, J=3.92 Hz). MS (m/z): 399 [MH]$^+$.

EXAMPLE 15

Preparation of N-Hydroxy-3-[1-(3-Dimethylamino-2,2-dimethyl-propyl)-2-phenethyl-1H-benzimidazol-5-yl]-acrylamide (17)

The titled compound (17) was prepared according to the procedures described in Example 1, by using appropriate starting materials. HPLC: 100%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 2.13 min. NMR (400 MHz, DMSO-$d_6$) δ 1.08 (6H, s), 2.89 (6H, s), 4.30 (2H, s), 6.54 (1H, d, J=15.80 Hz), 7.03 (1H, s), 7.16 (1H, s), 7.22-7.32 (6H, m), 7.65 (1H, d, J=15.80 Hz), 7.91 (1H, s). MS (m/z): 421 [MH]$^+$.

EXAMPLE 16

Preparation of N-Hydroxy-3-[2-Benzyloxymethyl-1-(3-hydroxy-propyl-1H-benzimidazl-5yl]-acrylamide (19)

The titled compound (19) was prepared according to the procedures described in Example 1, by using appropriate starting materials. HPLC: 98.6%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 4.50 min. $^1$H NMR (400 MHz, DMSO-$d_6$) δ 1.94 (2H, m), 3.43 (2H, t, J=5.8 Hz), 4.42 (2H, t, J=7.2 Hz), 4.67 (2H, s), 4.97 (2H, s), 6.53 (1H, d, J=15.8 Hz), 7.38 (5H, m), 7.63 (1H, d, J=15.8 Hz), 7.67 (1H, d, J=9.1 Hz), 7.80 (1H, d, J=8.6 Hz), 7.90 (1H, s), 10.77 (1H, bs). MS (m/z): 382 [MH]$^+$.

EXAMPLE 17

Preparation of N-Hydroxy-3-[1-(3-hydroxy-propyl)-2-thiophen-3-yl-1H-benzimidazol-5-yl]-acrylamide (20)

The titled compound (20) was prepared according to the procedures described in Example 1, by using appropriate starting materials. HPLC: 97.9%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 3.06 min. $^1$H NMR (400 MHz, DMSO-d$_6$), δ 1.98 (2H, m), 3.49 (2H, t, J=5.8 Hz), 4.56 (2H, t, J=7.2 Hz), 6.56 (1H, d, J=15.8 Hz), 7.65 (1H, d, J=15.8 Hz), 7.69 (1H, d, J=8.7 Hz), 7.75 (1H, dd, J=5.1 Hz, 1.2 Hz), 7.89 (2H, m), 7.93 (1H, s), 8.42 (1H, dd, J=2.6 Hz), 10.90 (1H, bs); MS (m/z): 344 [MH]$^+$.

EXAMPLE 18

Preparation of N-Hydroxy-3-[1-(3-hydroxy-propyl)-2-isobutyl-1H-benzimidazol-5-yl]-acrylamide (21)

The titled compound (21) was prepared according to the procedures described in Example 1, by using appropriate starting materials. HPLC: 100%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 3.14 min. $^1$H NMR (400 MHz, DMSO-d$_6$), δ 1.01 (6H, d, J=6.6 Hz), 1.94 (2H, m), 2.28 (1H, m), 3.04 (2H, d, J=7.4 Hz), 3.47 (2H, t, J=5.8 Hz), 4.46 (2H, t, J=7.1 Hz), 6.56 (1H, d, J=15.8 Hz), 7.65 (1H, d, J=15.8 Hz), 7.73 (1H, d, J=8.6 Hz), 7.89 (1H, d, J=8.6 Hz), 7.94 (1H, s). MS (m/z): 318 [MH]$^+$.

EXAMPLE 19

Preparation of N-Hydroxy-3-[1-(3-hydroxy-propyl)-2-octyl-1H-benzimidazol-5-yl]-acrylamide (23)

The titled compound (23) was prepared according to the procedures described in Example 1, by using appropriate starting materials. HPLC: 99.0%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 7.38 min. $^1$H NMR (400 MHz, DMSO-d$_6$) δ 0.86 (3H, t, J=6.8 Hz), 1.32 (10H, m), 1.83 (2H, m), 1.94 (2H, m), 3.12 (2H, t, J=7.7 Hz), 3.46 (2H, t, J=5.8 Hz), 4.44 (2H, t, J=7.0 Hz), 6.56 (1H, d, J=15.8 Hz), 7.64 (1H, d, J=15.8 Hz), 7.71 (1H, d, J=8.6 Hz), 7.87 (1H, d, J=8.6 Hz), 7.92 (1H, s). MS (m/z): 374 [MH]$^+$.

EXAMPLE 20

Preparation of N-Hydroxy-[2-cyclohexyl-1-(3-hydroxy-propyl)-1H-benzimidazol-5-yl]-acrylamide (24)

The titled compound (24) was prepared according to the procedures described in Example 1, by using appropriate starting materials. HPLC: 98.0%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 7.38 min. $^1$H NMR (400 MHz, DMSO-d$_6$) δ 1.28-2.03 (12H, m), 3.33 (1H, m), 3.47 (2H, t, J=5.7 Hz), 4.51 (2H, t, J=6.9 Hz), 6.58 (1H, d, J=15.8 Hz), 7.65 (1H, d, J=15.8 Hz), 7.76 (1H, d, J=8.6 Hz), 7.92 (1H, d, J=8.7 Hz), 7.93 (1H, s), 10.85 (1H, bs). MS (m/z): 344 [MH]$^+$.

EXAMPLE 21

Preparation of N-Hydroxy-3-(2-isobutyl-1-phenethyl-1H-benzimidazol-5-yl]-acrylamide (25)

The titled compound (25) was prepared according to the procedures described in Example 1, by using appropriate starting materials. HPLC: 99.1%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 6.51 min. $^1$H NMR (400 MHz, DMSO-d$_6$) δ 0.90 (6H, d, J=6.6 Hz), 2.10 (1H, m), 2.70 (2H, d, J=7.3 Hz), 3.11 (2H, t, J=7.0 Hz), 4.66 (2H, t, J=7.0 Hz), 6.57 (1H, d, J=15.8 Hz), 7.14 (2H, m), 7.26 (3H, m), 7.64 (1H, d, J=15.8 Hz), 7.70 (1H, d, J=8.8 Hz), 7.86 (1H, d. J=8.6 Hz), 7.92 (1H, s); $^{13}$C NMR (100 MHz, DMSO-d$_6$) δ 22.0, 26.9, 33.3, 34.5, 45.8, 113.0, 114.3, 119.7, 123.7, 126.9, 128.5, 129.0, 132.2, 132.7, 137.2, 137.8, 154.4, 162.5. MS (m/z): 364 [MH]$^+$.

EXAMPLE 22

Preparation of N-Hydroxy-3-(1,2-Diphenethyl-1H-benzimidazol-5-yl]-acrylamide (26)

The titled compound (26) was prepared according to the procedures described in Example 1, by using appropriate starting materials. HPLC: 98.3%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 7.68 min. $^1$H NMR (400 MHz, DMSO-d$_6$) δ 2.99 (4H, m), 3.09 (2H, m), 4.59 (2H, t, J=6.9 Hz), 6.56 (1H, d, J=15.8 Hz), 7.07 (2H, m), 7.23 (6H, m), 7.31 (2H, m), 7.64 (1H, d, J=15.5 Hz), 7.66 (1H, d, J=7.2 Hz), 7.78 (1H, d, J=8.6 Hz), 7.92 (1H, s); $^{13}$C NMR (100 MHz, DMSO-d$_6$) δ 27.0, 31.9, 34.5, 45.6, 112.7, 114.7, 119.4, 123.5, 126.5, 126.9, 128.3, 128.5, 129.0, 131.8, 133.0, 137.3, 138.0, 139.5, 154.6, 162.6. MS (m/z): 412 [MH]$^+$.

EXAMPLE 23

Preparation of N-Hydroxy-3-(2-phenethyl-1-(2-pyridin-3-yl-ethyl)-1H-benzimidazol-5-yl]-acrylamide (27)

The titled compound (27) was prepared according to the procedures described in Example 1, by using appropriate starting materials. HPLC: 99.9%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 3.42 min. $^1$H NMR (400 MHz, DMSO-d$_6$) δ 3.10 (4H, m), 3.28 (2H, t), 4.63 (2H, t) 6.53 (1H, d), 7.22-7.33 (7H, m), 7.54-7.74 (4H, m), 8.55 (2H, d), 10.88 (1H, bs). MS (m/z): 413 [MH]$^+$.

EXAMPLE 24

Preparation of N-Hydroxy-3-[1-(3-Hydroxy-propyl)-2-isobutyl-1H-benzimidazol-5-yl]-propionamide (29)

The titled compound (29) was prepared according to the procedures described in Example 1, by using appropriate starting materials. HPLC: 99.6%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 2.88 min. $^1$H NMR (400 MHz, DMSO-d$_6$) δ 1.00 (6H, d, J=6.4 Hz), 2.06 (2H, m), 2.27 (1H, m), 2.42 (2H, t, J=7.6 Hz), 3.05-3.11 (4H, m), 3.57 (2H, t, J=6.0 Hz), 4.52 (2H, t, J=7.2 Hz), 7.45 (1H, d, J=8.0 Hz), 7.56 (1H, s), 7.78 (1H, d, J=8.0 Hz); $^{13}$C NMR (100 MHz, MeOD) δ 20.6 (2C), 27.2, 30.4, 30.6, 32.7, 33.5, 41.5, 57.0, 112.0, 112.3, 112.4, 126.3, 129.9, 139.6, 152.3, 169.4. MS (m/z): 320 [MH]$^+$.

EXAMPLE 25

Preparation of N-Hydroxy-3-{1-[3-(2-oxo-pyrrolidin-1-yl)-propyl]-2-phenethyl-1H-benzimidazol-5-yl}acrylamide (30)

The titled compound (30) was prepared according to the procedures described in Example 1, by using appropriate starting materials. HPLC: 99.7%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 2.88 min. $^1$H NMR (400 MHz, DMSO-d$_6$) δ 1.84 (4H, m), 3.14-3.41 (8H, m), 4.29 (2H, t, J=7.04 Hz), 6.54 (1H, d, J=15.76 Hz), 7.21-7.33 (5H, m), 7.62 (1H, d, J=15.76 Hz), 7.71 (1H, d, J=8.36 Hz), 7.84 (1H, d, J=8.36 Hz), 7.93 (1H, s). MS (m/z): 433 [MH]$^+$.

EXAMPLE 26

Preparation of N-Hydroxy-3-[1-(3-morpholin-4-propyl]-2-phenethyl-1H-benzimidazol-5-yl}-acrylamide (31)

The titled compound (31) was prepared according to the procedures described in Example 1, by using appropriate starting materials. HPLC: 99.7%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 2.16 min. $^1$H NMR (400 MHz, DMSO-d$_6$) δ 2.12 (2H, m), 3.11 (6H, m), 3.39 (2H, t, J=7.44 Hz), 4.39 (2H, t, J=7.01 Hz), 6.56 (1H, d, J=15.8 Hz), 7.23-7.33 (5H, m), 7.62 (1H, d, J=15.8 Hz), 7.71 (1H, d, J=8.60 Hz), 7.85 (1H, d, J=8.60 Hz), 7.95 (1H, s). MS (m/z): 435 [MH]$^+$.

EXAMPLE 27

Preparation of 3-[5-(2-Hydrocarbamoyl-vinyl)-2-phenethyl-benzimidazol-1-yl]-propionic acid (32)

The titled compound (32) was prepared according to the procedures described in Example 1, by using appropriate starting materials. HPLC: 95.6%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 2.55 min. $^1$H NMR (400 MHz, DMSO-d$_6$) δ 2.74 (2H, t, J=6.68 Hz), 4.49 (2H, t, J=6.68 Hz), 3.16 (2H, t, J=7.44 Hz), 6.52 (1H, d, J=15.76 Hz), 7.22-7.33 (5H, m), 7.62 (1H, d, J=15.76 Hz), 7.66 (1H, d, J=8.56 Hz), 7.82 (1H, d, J=8.56 Hz), 7.89 (1H, s), 11.00 (1H, s)

MS (m/z): 380 [MH]$^+$.

EXAMPLE 28

Preparation of N-Hydroxy-3-(1-Benzyl-2-phenethyl-1H-benzimidazol-5-yl}-acrylamide (33)

The titled compound (33) was prepared according to the procedures described in Example 1, by using appropriate starting materials. HPLC: 99.0%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 7.82 min. $^1$H NMR (400 MHz, DMSO-d$_6$) δ 3.08 (2H, t, J=7.4 Hz), 3.34 (2H, t, J=7.5 Hz), 5.62 (2H, s), 6.50 (1H, d, J=15.8 Hz), 7.14 (2H, m), 7.30 (8H, m), 7.63 (3H, m), 7.92 (1H, s), 10.78 (1H, br); $^{13}$C NMR (100 MHz, DMSO-d$_6$) δ 27.8, 32.2, 46.8, 112.1, 115.9, 118.6, 123.0, 126.4, 126.8, 127.9, 128.3, 128.4, 128.9, 131.0, 134.4, 135.7, 138.4, 139.9, 155.3, 162.7. MS (m/z): 398 [MH]$^+$.

EXAMPLE 29

Preparation of N-Hydroxy-3-(1-Benzyl-2-isobutyl-1H-benzimidazol-5-yl}-acrylamide (34)

The titled compound (34) was prepared according to the procedures described in Example 1, by using appropriate starting materials. HPLC: 89.2%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 6.07 min. $^1$H NMR (400 MHz, CDCl$_3$) δ 0.92 (6H, d, J=6.6 Hz), 2.13 (1H, m), 3.02 (2H, d, J=7.4 Hz), 5.72 (2H, s), 6.54 (1H, d, J=15.8 Hz), 7.21 (2H, m), 7.35 (3H, m), 7.66 (3H, m), 7.96 (1H, s); $^{13}$C NMR (100 MHz, CDCl$_3$) δ 22.0, 27.2, 34.0, 47.2, 112.8, 114.9, 119.4, 123.7, 126.8, 128.0, 128.9, 131.9, 133.6, 135.3, 138.0, 155.0, 162.6. MS (m/z): 350 [MH]$^+$.

EXAMPLE 30

Preparation of N-Hydroxy-3-(1-Benzyl-1H-benzimidazol-5-yl}-acrylamide (35)

The titled compound (35) was prepared according to the procedures described in Example 1, by using appropriate starting materials. HPLC: 97.0%; $t_R$=(LC/PDA: Phenomenex Luna C18 2.0×150 mm 5μ column; 0.8 mL/min, gradient 5-65% B over 15.5 min, Solvent A: H$_2$O with 0.1% trifluoroacetic acid; Solvent B: Acetonitrile with 0.1% trifluoroacetic acid; UV 254): 3.69 min. $^1$H NMR (400 MHz, CD$_3$OD) δ 5.68 (2H, s), 6.54 (1H, d, J=15.7 Hz), 7.37 (5H, m), 7.66 (1H, d, J=15.8 Hz), 7.75 (2H, s), 7.94 (1H, s), 9.36 (1H, br); $^{13}$C NMR (100 MHz, CD$_3$OD) δ 51.7, 114.8, 116.1, 120.6, 126.5, 129.2, 130.2, 130.4, 135.0, 135.3, 140.1, 165.6. MS (m/z): 294 [MH]$^+$.

EXAMPLE 31

Preparation of N-Hydroxy-3-(2-phenethyl-1-propyl-1H-benzimidazol-5-yl}-acrylamide (36)

The titled compound (36) was prepared according to the procedures described in Example 1, by using appropriate starting materials. HPLC: 93.9%; $t_R$=(LC/PDA: Phenomenex Luna C18 2.0×150 mm 5, column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 6.05 min. $^1$H NMR 400 MHz, $CD_3OD$) δ 0.90 (3H, t, J=7.4 Hz), 1.70 (2H, m), 3.20 (2H, m), 3.48 (2H, t, J=7.1 Hz), 4.21 (2H, t, J=7.4 Hz), 6.54 (1H, d, J=15.7 Hz), 7.20 (5H, m), 7.65 (1H, d, J=15.7 Hz), 7.75 (1H, d, J=8.8 Hz), 7.79 (1H, d, J=8.6 Hz), 7.84 (1H, s); $^{13}$C NMR (100 MHz, $CD_3OD$) δ 11.2, 23.6, 28.7, 34.0, 47.7, 114.4, 114.6, 120.5, 126.3, 128.3, 129.5, 130.0, 132.7, 134.0, 135.2, 139.9, 140.1, 155.5, 165.6. MS (m/z): 350 [MH]$^+$.

EXAMPLE 32

Preparation of N-Hydroxy-3-(1-propyl-1H-benzimidazol-5-yl}-acrylamide (37)

The titled compound (37) was prepared according to the procedures described in Example 1, by using appropriate starting materials. HPLC: 95.2%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 2.92 min. $^1$H NMR (400 MHz, $CD_3OD$) δ 0.97 (3H, t, J=7.4 Hz), 1.98 (2H, m), 4.42 (2H, t, J=7.3 Hz), 6.55 (1H, d, J=15.8 Hz), 7.68 (1H, d, J=15.8 Hz), 7.79 (1H, d, J=8.7 Hz), 7.88 (1H, d, J=8.7 Hz), 7.92 (1H, s), 9.24 (1H, s); $^{13}$C NMR (100 MHz, $CD_3CD$) δ 11.1, 23.8, 48.4, 114.3, 116.1, 120.3, 126.4, 133.8, 134.9, 135.0, 140.3, 143.5, 165.7. MS (m/z): 246 [MH]$^+$.

EXAMPLE 33

Preparation of N-Hydroxy-3-(1-Ethyl-2-phenethyl-1H-benzimidazol-5-yl}-acrylamide (38)

The titled compound (38) was prepared according to the procedures described in Example 1, by using appropriate starting materials. HPLC: 99.0%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 5.06 min. $^1$H NMR: (400 MHz, $CD_3OD$) δ 1.37 (3H, t, J=7.3 Hz), 3.26 (2H, t, J=7.6 Hz), 3.53 (2H, t, J=7.5 Hz), 4.78 (2H, dd, J=7.3 Hz), 6.60 (1H, d, J=15.8 Hz), 7.21-7.31 (5H, m), 7.72 (1H, d, J=15.8 Hz), 7.83-7.89 (3H, m). MS (m/z): 336 [MH]$^+$.

EXAMPLE 34

Preparation of N-Hydroxy-3-(1-Ethyl-1H-benzimidazol-5-yl}-acrylamide (39)

The titled compound (39) was prepared according to the procedures described in Example 1, by using appropriate starting materials. HPLC: 99.0%; $t_R$=(LC/PDA: Phenomenex Luna C18 2.0×150 mm 5, column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 1.86 min. $^1$H NMR: (400 MHz, $CD_3OD$) δ 1.64 (3H, t, J=7.3 Hz), 4.55 (2H, dd, J=7.3 Hz), 6.61 (1H, d, J=15.8 Hz), 7.72 (1H, d, J=15.8 Hz), 7.86-7.97 (3H, m), 9.38 (1H, s). MS (m/z): 232 [MH]$^+$.

EXAMPLE 35

Preparation of 1-(3-Hydroxy-propyl)-2-phenethyl-1H-benzimidazol-5-carboxylic acid hydroxyamide (40)

The title compound (40) was prepared according to the procedures described in Example 1, by using appropriate starting materials. HPLC: 96.0%. $^1$H NMR (400 MHz, CD3OD, 5): 1.88 (2H, m), 3.16 (2H, t, J=7.2 Hz), 3.46 (4H, m), 4.34 (2H, t, J=7.2 Hz), 7.12-7.21 (5H, m), 7.82 (2H, m), 8.05 (1H, s). MS (m/z): 340 [MH]$^+$.

EXAMPLE 36

Preparation of N-Hydroxy-3-[1-(2-pyridin-2-yl-ethyl)-1H-benzimidazol-5-yl]-acrylamide (42)

The titled compound (42) was prepared according to the procedures described in Example 1, by using appropriate starting materials. HPLC: 98.4%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 1.05 min. $^1$H NMR (400 MHz, DMSO-$d_6$) δ 3.43 (2H, t), 4.84 (2H, t), 6.53 (1H, d), 7.41 (2H, m), 7.64 (2H, m), 7.77-7.95 (4H, m), 8.56 (1H, s), 9.16 (1H, s). MS (m/z): 309 [MH]$^+$.

EXAMPLE 37

Preparation of N-Hydroxy-3-(1-Ethyl-2-methyl-1H-benzimidazol-5-yl]-acrylamide (43)

The titled compound (43) was prepared according to the procedures described in Example 1, by using appropriate starting materials. HPLC: 96.5%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 2.52 min. $^1$H NMR (400 MHz, DMSO-$d_6$) δ 1.38 (3H, t), 2.85 (3H, s), 4.42 (2H, t), 6.58 (1H,d), 7.31 (1H, m), 7.50 (1H.d), 7.88 (2H, m), 10.31 (1H, bs), 11.18 (1H, bs). MS (m/z): 246 [MH]$^+$.

EXAMPLE 38

Preparation of N-Hydroxy-3[1-(3-hydroxy-propyl)-1H-benzimidazol-5-yl]-acrylamide (47)

The titled compound (47) was prepared according to the procedures described in Example 1, by using appropriate starting materials. HPLC: >99%; $t_R$=(LC/PDA: Phenomenex Luna C18 2.0×150 mm 5, column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 1.02 min. $^1$H NMR (400 MHz, $CD_3OD$) δ 2.12 (2H, m), 3.58 (2H, t, J=5.7 Hz), 4.57 (2H, t, J=6.9 Hz), 6.55 (1H, d, J=15.8 Hz), 7.67 (1H, d, J=15.8 Hz), 7.79 (1H, d, J=8.7 Hz), 7.89 (1H, d, J=8.9 Hz), 7.92 (1H, s), 9.22 (1H, s); $^{13}$C NMR (100 MHz, MeOD) δ 32.7, 45.3, 59.2, 114.3, 116.1, 120.3, 126.4, 135.0, 140.3, 143.8, 165.7. MS (m/z): 262 [MH]$^+$.

EXAMPLE 39

Preparation of N-Hydroxy-3-(1-methyl-2-phenethyl-1H-benzimidazol-5-yl)-acrylamide (48)

The titled compound (48) was prepared according to the procedures described in Example 1, by using appropriate starting materials. HPLC: 99%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 4.53 min. $^1$H NMR: (400 MHz, $CD_3OD$) δ 3.18 (2H, t, J=7.5 Hz), 3.47 (2H, t, J=7.4 Hz), 3.76 (3H, s), 6.54 (1H, d, J=15.8 Hz), 7.10-7.26 (5H, m), 7.65 (1H, d, J=15.8 Hz), 7.75-7.82 (3H, m). MS (m/z): 322 $[MH]^+$.

EXAMPLE 40

Preparation of N-Hydroxy-3-(2-phenethyl-1H-benzimidazol-5-yl)-acrylamide (50)

The titled compound (50) was prepared according to the procedures described in Example 1, by using appropriate starting materials. HPLC: 99%; $t_R$=(LC/PDA: Phenomenex Luna C18 2.0×150 mm 5, column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 4.36 min. $^1$H NMR (400 MHz, DMSO-$d_6$) δ 3.16 (2H, t, J=7.5 Hz), 3.36 (2H, t, J=7.9 Hz), 6.53 (1H, d, J=15.8 Hz), 7.17-7.29 (5H, m), 7.58 (1H, d, J=15.8 Hz), 7.66-7.87 (3H, m). MS (m/z): 308 $[MH]^+$.

EXAMPLE 41

Preparation of N-Hydroxy-3-(1H-benzimidazol-5-yl)-acrylamide (51)

The titled compound (51) was prepared according to the procedures described in Example 1, by using appropriate starting materials. HPLC: 99%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 0.99 min. $^1$H NMR (400 MHz, DMSO-$d_6$) δ 6.62 (1H, d, J=15.8 Hz), 7.74 (1H, d, J=15.8 Hz), 7.85-7.99 (3H, m), 9.32 (1H, s). MS (m/z): 204 $[MH]^+$

EXAMPLE 42

Preparation of N-Hydroxy-3-[1-methyl-2-(3-phenyl-propyl)-1H-benzimidazol-5-yl]-acrylamide (52)

Step 1

To a pre-stirred solution of methyl trans-4-(methylamine)-3-nitrocinnamate (1.0 g, 4.0 mmol; prepared as described in Example 1) in 40 mL methanol and 10 mL glacial acetic acid, was added Tin chloride (3.0 g, 16.0 mmol). The resulting solution was heated to 55° C. for 24 hours and then cooled to room temperature. The solvent was removed and the mixture was neutralized with sodium bicarbonate to pH=8. The crude product was extracted with dichloromethane (20 mL) for three times. The organic extracts were combined and washed with water (10 mL) twice and brine (10 mL) once and further dried over $Na_2SO_4$ for 1 hour, filtered and concentrated. The product methyl trans-4-(methylamine)-3-aminocinnamate was obtained in 82.5% yield (726 mg). MS(m/z): 207 $[MH]^+$.

Step 2

4-phenylbutyric acid (68 mg, 0.41 mmol), methyl trans-4-(methylamine)-3-aminocinnamate (85 mg, 0.40 mmol) and PyBOP (236 mg, 0.46 mmol) were mixed in a 25 mL round bottom flask with 10 mL of dried dichloromethane. The resulting mixture was stirred under nitrogen atmosphere for 5 minutes. DIEA (288 uL, 1.62 mmol) was injected and the resulting mixture was stirred at room temperature for another 4 hours. The progress of the reaction was monitored by TLC. The coupling products, 3-{3-amino-4-[methyl-(4-phenyl-butyryl)amino]-phenyl}-acrylic acid methyl ester and 3-[4-methylamino-3-(4-phenyl-butyrylamino)-phenyl]-acrylic acid methyl ester, were obtained (110 mg 78%) after purification using column chromatography. (Solvent system: Ethyl acetate:hexane=1:1) MS(m/z): 353 $[MH]^+$.

Step 3

The above coupling products (59 mg, 0.17 mmol) was heated with 5 mL of glacial acetic acid at 70° C. for 4 hours. After cooling down to room temperature, the pure product, 3-[1-methyl-2-(3-phenyl-propyl)-1H-benzimidazol-5-yl]-acrylic acid methyl ester, was obtained quantitatively by removing glacial acetic acid under vacuum. $^1$H NMR (400 MHz, DMSO-$d_6$) δ 2.14 (2H, m), 2.75 (2H, t), 3.14 (2H, t), 3.95 (3H, s), 6.58 (1H,d), 7.16-7.30 (5H, m), 7.65 (1H.d), 7.72 (1H, d), 7.90 (2H, m). MS(m/z): 335 $[MH]^+$.

Step 4

The titled compound (52) was prepared according to the procedures for preparation of hydroxamic acid as described in Example 1, by using appropriate starting materials. HPLC: 99.8%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 5.01 min. $^1$H NMR (400 MHz, DMSO-$d_6$) δ 2.14 (2H, m), 2.75 (2H, t), 3.14 (2H, t), 3.95 (3H, s), 6.58 (1H,d), 7.16-7.30 (5H, m), 7.65 (1H.d), 7.72 (1H, d), 7.90 (2H, m), 10.89 (1H, bs). MS (m/z): 336 $[MH]^+$.

EXAMPLE 43

Preparation of N-Hydroxy-3-[1-(3-imidazol-1-yl-propyl)-2-phenethyl-1H-benzimidazol-5-yl]-acrylamide (56)

The titled compound (56) was prepared according to the procedures described in Example 1, by using appropriate starting materials. HPLC: 98.0%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 3.50 min. $^1$H NMR (400 MHz, $CD_3OD$) δ 2.20 (2H, m), 3.19 (2H, m), 3.39 (2H, t, J=7.6 Hz), 4.28 (4H, t, J=7.6 Hz), 6.52 (1H, d, J=16.0 Hz), 7.17 (5H, m), 7.52 (1H, t, J=1.5 Hz), 7.58 (1H, t, J=1.6 Hz), 7.65 (1H, d, J=16.0 Hz), 7.68 (2H, s), 7.85 (1H, s), 8.84(1H, s); $^{13}$C NMR (100 MHz, $CD_3OD$) δ 29.3, 30.7, 34.4, 42.4, 47.6, 113.0, 116.2, 119.2, 121.6, 123.1, 125.7, 128.0, 129.6, 129.9, 133.7, 135.1, 136.6, 137.2, 140.7, 140.9, 156.5, 166.0. MS (m/z): 416 $[MH]^+$.

EXAMPLE 44

Preparation of N-Hydroxy-3-[1-(4-dimethylamino-butyl)-2-phenethyl-1H-benzimidazol-5-yl]-acrylamide (57)

The titled compound (57) was prepared according to the procedures described in Example 1, by using appropriate starting materials. HPLC: 97.0%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 3.70 min. $^1$H NMR (400 MHz, $CD_3OD$) δ 1.71 (4H, m), 2.82 (6H, s), 3.05 (2H, t, J=7.1 Hz), 3.21 (2H, t, J=7.6 Hz), 3.44 (2H, t, J=7.5 Hz), 4.27 (2H, t, J=7.5 Hz), 6.53 (1H, d, J=16.0 Hz), 7.20 (5H, m), 7.65 (1H, d, J=16.0 Hz), 7.73 (2H, m), 7.85 (1H, 5); $^{13}$C NMR (100 MHz, $CD_3OD$) δ 22.8, 27.3, 29.1, 34.2, 43.5, 45.1, 58.3, 113.5, 115.6, 119.6, 125.9, 128.1, 129.5, 130.0, 134.2, 134.7, 140.4, 140.6, 156.2, 162.7, 165.9. MS (m/z): 407 [MH]$^+$.

EXAMPLE 45

Preparation of N-Hydroxy-3-[1-(3-Hydroxy-propyl)-2-isobutyl-1H-benzimidazol-5-yl]-acrylamide (29)

Step 1

3-[1-(3-hydroxy-propyl)-2-isobutyl-1H-benzimidazol-5-yl]-acrylic acid methyl ester (prepared according to the Example 1, step 1-3) (126.6 mg, 0.4 mmol) and 10% Pd/C (40 mg) in 10 mL of MeOH was hydrogenated using a hydrogen balloon overnight. After filtration through short-column silica gel, the filtrate was evaporated under reduced pressure to give 3-[1-(3-hydroxy-propyl)-2-isobutyl-1H-benzimidazol-5-yl]-propionic acid methyl ester (127 mg) in quantitative yield: MS m/z (M+H)$^+$: 319; $^1$H NMR (400 MHz, MeOD) δ 0.95 (6H, d, J=6.4 Hz), 1.92 (2H, m), 2.19 (1H, m), 2.60 (2H, t, J=8.0 Hz), 2.74 (2H, d, J=7.2 Hz), 2.96 (2H, t, J=7.6 Hz), 3.50 (2H, t, J=4.1 Hz), 3.54 (3H, s), 4.25 (2H, t, J=7.2 Hz), 7.05 (1H, d, J=8.0 Hz), 7.30-7.40 (2H, m); $^{13}$C NMR (100 MHz, MeOD) δ 20.9 (2C), 27.3, 30.1, 31.5, 34.6, 35.3, 39.5, 50.1, 57.4, 109.1, 116.4, 122.1, 132.6, 134.2, 141.3, 154.2, 173.2.

Step 2

The titled compound (29) was prepared according the method described previously for the preparation of hydroxamic acid: MS m/z (M+H)$^+$: 320; $^1$H NMR (400 MHz, MeOD) δ 1.00 (6H, d, J=6.4 Hz), 2.06 (2H, m), 2.27 (1H, m), 2.42 (2H, t, J=7.6 Hz), 3.05-3.11 (4H, m), 3.57 (2H, t, J=6.0 Hz), 4.52 (2H, t, J=7.2 Hz), 7.45 (1H, d, J=8.0 Hz), 7.56 (1H, s), 7.78 (1H, d, J=8.0 Hz); $^{13}$C NMR (100 MHz, MeOD) δ 20.6 (2C), 27.2, 30.4, 30.6, 32.7, 33.5, 41.5, 57.0, 112.0, 112.3, 112.4, 126.3, 129.9, 139.6, 152.3, 169.4.

EXAMPLE 46

Preparation of N-Hydroxy-3-[2-(benzylamino-methyl)-1-methyl-1H-benzimidazol-5-yl]-acrylamide (60)

Step 1

3-[2-(N-Fmoc-aminomethyl)-1-methyl-1H-benzimidazol-5-yl]-acrylic acid methyl ester (43 mg, 0.176 mmol, prepared according to Example 42, step 1-3 by using appropriate starting materials) was dissolved in 10 mL of dichloromethane. The resulting solution was treated with 2.0 mL of piperidine. Removed all the solvent and piperidine under vacuum gave 3-(2-aminomethyl-1-methyl-1H-benzimidazol-5-yl)-acrylic acid methyl ester. MS(m/z): 246 [MH]$^+$.

Step 2

Benzaldehyde (47 mg, 0.445 mmol), 3-(2-aminomethyl-1-methyl-1H-benzimidazol-5-yl)-acrylic acid methyl ester (109 mg, 80%, 0.445 mmol) and acetic acid (27 mg, 0.445 mmol) were dissolved in 15 mL of dichloromethane. The mixture was stirred at room temperature for 1 hour. Sodium triacetoxyborohydride (142 mg, 95%, 0.668 mmol) was added to the above solution. The reaction was completed after 12 hours and the organic layer was washed with saturated $NaHCO_3$ (10 mL) twice, followed by washing with water (10 mL) twice, with brine (10 mL) once and then dried over $Na_2SO_4$. After filtration, the crude product (100 mg, 67.6% yield), 3-[2-(benzylamino-methyl)-1-methyl-1H-bezimidazol-5-yl]-acrylic acid methyl ester, was obtained by removing the solvent. MS(m/z): 336 [MH]$^+$.

Step 3

The titled compound (60) was prepared according to the procedures described in Step 4 of Example 1, by using 3-[2-(benzylamino-methyl)-1-methyl-1H-bezimidazol-5-yl]-acrylic acid methyl ester as the starting material HPLC: 89.6%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 3.68 min. $^1$H NMR (400 MHz, DMSO-$d_6$) δ 3.78(3H, s), 4.37 (2H, s), 4.58 (2H, s), 6.48 (1H,d), 7.46 (3H, m), 7.55 (3H, m) 7.64 (2H, t) 7.88 (1H, s), 9.88 (1H, bs), 10.74 (1H, bs). MS (m/z): 337 [MH]$^+$.

EXAMPLE 47

Preparation of N-Hydroxy-3-[1-(3-dimethylamino-propyl)-2-phenethyl-1H-benzimidazol-5-yl]-acrylamide (63)

The titled compound (63) was prepared according to the procedures described in Example 1, by using appropriate starting materials. HPLC: 100%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 3.52 min. $^1$H NMR (400 MHz, DMSO-$d_6$) δ 2.09 (2H, m), 2.75 (3H, s), 2.76 (3H, s), 3.12-3.22 (4H, m), 3.37 (2H, b), 4.50 (2H, b), 6.55 (1H, d, J=15.76 Hz), 7.22-7.34 (5H, m), 7.63 (1H, d, J=15.76 Hz), 7.66 (1H, d, J=7.80 Hz), 7.82 (1H, d, 7.80 Hz), 7.92 (1H, s). MS (m/z): 393 [MH]$^+$.

EXAMPLE 48

Preparation of N-Hydroxy-3-[2-(benzylamino-methyl)-ethyl-1H-benzimidazol-5-yl]-acrylamide (64)

The titled compound (64) was prepared according to the procedures described in Example 46, by using appropriate starting materials. HPLC: 98.5%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 3.52 min. $^1$H NMR (400 MHz, DMSO-$d_6$) δ 1.31 (3H, t) 3.37(2H, m), 3.50 (2H, t), 4.28 (4H, m), 6.48

(1H,d), 7.43-50 (3H, m), 7.55 (3H, m) 7.73-7.83 (2H, t) 7.95 (1H, s), 9.25 (1H, bs), 10.76 (1H, bs). MS (m/z): 351 [MH]+.

EXAMPLE 49

Preparation of N-Hydroxy-3-(2-(benzyl-1-methyl-3-oxo-1H-benzimidazol-5-yl)-acrylamide (65)

The titled compound (65) was prepared according to the procedures described in Example 42, by using appropriate starting materials. HPLC: 99%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 4.48 min. $^1$H NMR (400 MHz, DMSO-$d_6$) δ 3.87 (3H, s), 4.59 (2H, s), 6.57 (1H, d, J=15.9 Hz), 7.09-7.36 (5H, m), 7.62 (1H, d, J=15.8 Hz), 7.73-7.95 (3H, m). MS (m/z): 309 [MH]+.

EXAMPLE 50

Preparation of N-Hydroxy-3-[1-(2-diethylamino-ethyl)-2-phenethyl-1H-benzimidazol-5-yl]-acrylamide (66)

The titled compound (66) was prepared according to the procedures described in Example 1, by using appropriate starting materials. HPLC: 100%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 3.72 min. $^1$H NMR (400 MHz, $CD_3OD$) δ1.29 (6H, t, J=7.3 Hz), 3.26 (8H, m), 3.40 (2H, t, J=7.5 Hz), 4.60 (2H, t, J=8.0 Hz), 6.50 (1H, d, J=16.0 Hz), 7.21 (5H, m), 7.62 (1H, d, J=16.0 Hz), 7.70 (2H, m), 7.85 (1H, s); $^{13}$C NMR (100 MHz, $CD_3OD$) δ9.0, 29.4, 34.3, 39.9, 48.4, 50.3, 112.7, 116.6, 119.3, 125.8, 128.1, 129.6, 130.0, 133.9, 134.9, 137.6, 140.8, 157.0, 166.0. MS (m/z): 407 [MH]+.

EXAMPLE 51

Preparation of N-Hydroxy-3-[2-phenethyl-1-(piperidin-1-yl-ethyl)-1H-benzimidazol-5-yl]-acrylamide (67)

The titled compound (67) was prepared according to the procedures described in Example 1, by using appropriate starting materials. HPLC: 100%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 3.90 min. $^1$H NMR (400 MHz, $CD_3OD$) δ1.86 (6H, br s), 3.26 (8H, m), 3.40 (2H, t, J=7.5 Hz), 4.62 (2H, t, J=7.9 Hz), 6.50 (1H, d, J=16.0 Hz), 7.23 (5H, m), 7.62 (1H, d, J=16.0 Hz), 7.70 (2H), 7.84 (1H, s); $^{13}$C NMR (100 MHz, $CD_3OD$) δ22.5, 24.2, 29.4, 34.3, 39.6, 54.4, 54.9, 112.7, 116.6, 119.2, 125.7, 128.1, 129.6, 130.0, 133.8, 134.9, 137.8, 140.8, 157.0, 166.0. MS (m/z): 419 [MH]+.

EXAMPLE 52

Preparation of N-Hydroxy-3-[2-phenyethyl-1-(2-pyrrolidin-1-yl-ethyl)-1H-benzimidazol-5-yl]-acrylamide (72)

The titled compound (72) was prepared according to the procedures described in Example 1, by using appropriate starting materials. HPLC: 100%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 3.71 min. $^1$H NMR (400 MHz, $CD_3OD$) δ2.06 (4H, br), 3.21 (2H, t, J=7.4 Hz), 3.26 (4H, m), 3.37 (2H, t, J=7.7 Hz), 3.42 (2H, t, J=7.5 Hz), 4.57 (2H, t, J=7.4 Hz), 6.47 (1H, d, J=16.0 Hz), 7.21 (5H, m), 7.58 (1H, d, J=16.0 Hz), 7.67 (1H, d, J=8.6 Hz), 7.74 (1H, d, J=8.6 Hz), 7.83 (1H, s); $^{13}$C NMR (100 MHz, $CD_3OD$) δ24.1, 29.4, 34.3, 41.1, 52.8, 55.7, 112.9, 116.5, 119.2, 125.8, 128.1, 129.6, 130.0, 133.9, 134.9, 137.2, 140.7, 140.8, 157.0, 165.9. MS (m/z): 405 [MH]+.

EXAMPLE 53

Preparation of N-Hydroxy-3-[2-(2-benzylamino-ethyl)-1-ethyl-1H-benzimidazol-5-yl]-acrylamide (74)

The titled compound (74) was prepared according to the procedures described in Example 46, by using appropriate starting materials. HPLC: 98.5%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 3.52 min. $^1$H NMR (400 MHz, DMSO-$d_6$) δ 1.31 (3H, t) 3.37(2H, m), 3.50 (2H, t), 4.28 (4H, m), 6.48 (1H,d), 7.43-50 (3H, m), 7.55 (3H, m) 7.73-7.83 (2H, t) 7.95 (1H, s), 9.25 (1H, bs), 10.76 (1H, bs). MS (m/z): 365 [MH]+.

EXAMPLE 54

Preparation of N-Hydroxy-3-[2-phenethyl-1-(3-pyrrolidin-1-yl-propyl)-1H-benzimidazol-5-yl]-acrylamide (82)

The titled compound (82) was prepared according to the procedures described in Example 1, by using appropriate starting materials. HPLC: 100%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 1.18 min. $^1$H NMR (400 MHz, $CD_3OD$) δ 2.01 (2H), 2.17 (4H), 3.03 (2H), 3.26 (4H), 3.48 (2H), 3.62 (2H), 4.37 (2H), 6.60 (1H), 7.27 (5H), 7.71 (1H), 7.78 (2H), 7.91 (1H). MS (m/z): 419 [MH]+.

EXAMPLE 55

Preparation of N-Hydroxy-3-[1-(3-Dimethylamino-2,2-dimethyl-propyl)-2-(2-pyridin-3-yl-ethyl)-1H-benzimidazol-5-yl]-acrylamide (86)

The titled compound (86) was prepared according to the procedures described in Example 42, by using appropriate starting materials. HPLC: 90.4%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 1.24 min. $^1$H NMR (400 MHz, DMSO-$d_6$) δ 1.00 (6H, s), 2.94 (6H, s), 3.32 (2H, m), 3.38 (4H, m) 4.35 (2H, m), 6.52 (1H,d), 7.58-7.86 (5H, m) 8.20 (1H, d), 8.65 (1H, m) 8.77 (1H, s), 9.50 (1H, s). MS (m/z): 422 [MH]+.

EXAMPLE 56

Preparation of 2-[2-Phenethyl-1-(3,4,5-trimethoxy-benzyl)-1H-benzimidazol-5-yl]-cyclopropanecarboxylic acid hydroxyamide (88)

Step 1

To a solution of $(CH_3)_3S(O)I$ (132 mg, 0.6 mmol) in anhydrous DMSO (1 mL) was added sodium hydride (28 mg, 60% in mineral oil) at room temperature under nitrogen gas, then a solution of the compound (244 mg, 0.5 mmol), 3-[2-phenethyl-1-(3,4,5-trimethoxy-benzyl)-1H-benzimidazol-5-yl]-acrylic acid methyl ester (prepared according to Example 1, step 1-3), in 4 mL of anhydrous THF was added after 10 mins. The resulting mixture was then stirred at room temperature overnight. After an aqueous work-up, the residue was obtained as oil (135 mg), which was then subjected to next step without further purification.

Step 2

To a solution of above crude product in 0.5 mL MeOH was added a pre-prepared 2.0 M $NH_2OH$ stock solution as we did before (2 mL). The resulting mixture was stirred at room temperature for 4 hrs. After quenching with TFA (0.4 mL), the resulting mixture was subjected to HPLC purification to afford 10 mg of desired titled compound (88). HPLC: 99%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 6.36 min. $^1$H NMR (400 MHz, $CD_3OD$) δ 1.21-1.29 (1H, m), 1.45-1.52 (1H, m), 1.75-1.79 (1H, m), 2.48-2.55 (1H, m), 2.99 (2H, t, J=8.0 Hz), 3.45 (2H, t, J=8.0 Hz), 3.61 (6H, s), 3.64 (3H, s), 5.42 (2H, s), 6.40 (2H, s), 7.00-7.18 (5H, m), 7.26 (1H, d, J=8.4 Hz), 7.45 (1H, s), 7.59 (1H, d, J=8.4 Hz). MS (m/z): 502 [MH]$^+$.

EXAMPLE 57

Preparation of N-Hydroxy-3-[2-benzylsulfanyl-1-(3-dimethylamino-2-2,dimethyl-propyl)-1H-benzimidazol-5-yl]-acrylamide (89)

Step 1

3-[4-(3-dimethylamino-2,2-dimethyl-propylamino)-3-nitro-phenyl]-acrylic acid (1.93 g, 6.0 mmol, prepared as described in Example 1, step 1), Tin chloride (13.5 g, 60 mmol) and MeOH (50 mL) was mixed and heated at 45° C. for 20 hours. The reaction mixture was cooled to room temperature and solvent was removed under reduced pressure. To the residue was added 100 mL dichloromethane and 100 mL water. The pH was adjusted to 10 with concentrated ammonia. The layers were separated, and the aqueous phase was extracted with 100 mL dichloromethane. The organic extracts were combined, dried over is sodium sulfate, filtered and the solvent was removed under reduced pressure. To the resulting residue was added MeOH (100 mL), $CS_2$ (18 mL) and potassium hydroxide (3.4 g. The reaction mixture was heated at 80° C. for 16 hours, then cooled to room temperature and the solvents were removed under reduced pressure. The resulting crude product was recrystallized from MeOH.

The product, 3-[1-(3-dimethylamino-2,2-dimethyl-propyl)-2-thioxo-2,3-dihydro-1H-benzimidazol-5-yl]-acrylic acid, was obtained in 75% yield in two steps (1.5 g). MS (m/z): 334 [MH]$^+$.

Step 2

3-[1-(3-dimethylamino-2,2-dimethyl-propyl)-2-thioxo-2,3-dihydro-1H-benzimidazol-5-yl]-acrylic acid (100 mg, 0.3 mmol), benzyl bromide (360 mg, 3.6 mmol), and potassium carbonate (0.83 g) were mixed with 10 mL DMF. The resulting mixture was stirred overnight at 45° C. The desired product, 3-[2-benzylsulfanyl-1-(3-dimethylamino-2,2-dimethyl-propyl)-2,3-dihydro-1H-benzimidazol-5-yl]-acrylic acid benzyl ester, was purified by preparative HPLC: 150 mg (yield, 76.6%).

$^1$H NMR (400 MHz, DMSO-$d_6$) δ 1.08 (6H, s), 2.88 (3H, s), 2.89 (3H, s), 3.30 (2H), 4.11 (2H, s), 4.65 (2H, s), 5.24 (2H, s), 6.72 (2H, d, J=15.96 Hz), 7.26-7.47 (10H, m), 7.68(2H, bs), 7.83 (1H, d, J=15.96 Hz), 8.00(1H, s). MS (m/z): 514 [MH]$^+$.

Step 3

The titled compound (89) was obtained by treating 3-[2-benzylsulfanyl-1-(3-dimethylamino-2,2-dimethyl-propyl)-2,3-dihydro-1H-benzimidazol-5-yl]-acrylic acid benzyl ester according to method previously described for the preparation of hydroxamic acid (Step 4 of Example 1). HPLC: 99%; $t_R$=(LC/PDA: Phenomenex Luna C18 2.0×150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 2.87 min. $^1$H NMR (400 MHz, DMSO-$d_6$) δ 1.09 (6H, s), 2.88 (3H, s), 2.89 (3H, s), 3.26 (2H), 4.11 (2H, s), 4.65 (2H, s), 6.48 (2H, d, J=15.79 Hz), 7.26-7.47 (6H, m), 7.58(1H, d, J=15.79 Hz), 7.65 (1H, d, J=8.48 Hz), 7.80 (1H, s). MS (m/z): 439 [MH]$^+$.

EXAMPLE 58

Preparation of N-Hydroxy-3-[1-(3-dimethylamino-2,2-dimethyl-propyl)-2-phenylmethanesulfonyl-1H-benzimidazol-5-yl]-acrylamide (91)

Step 1

118 mg of 3-[2-benzylsulfanyl-1-(3-dimethylamino-2,2-dimethyl-propyl)-2,3-dihydro-1H-benzimidazol-5-yl]-acrylic acid benzyl ester (prepared according Example 57, step 1-2), 1.0 mL of hydrogen peroxide (30%) and 10 mL of acetic acid were mixed at 0° C. in an ice bath. Without adding additional ice, the reaction mixture was stirred overnight. The product, 3-[1-(3-dimethylamino-2,2-dimethyl-propyl)-2-phenylmethanesulfinyl-2,3-hydro -1H-benzimidazol-5-yl]-acrylic acid benzyl ester, was obtained quantitatively. MS (m/z): 530 [MH]$^+$.

Step 2

The titled compound (91) was obtained by treating 3-[1-(3-dimethylamino-2,2-dimethyl-propyl) -2-phenylmethanesulfinyl-2,3-hydro-1H-benzimidazol-5-yl]-acrylic acid benzyl ester according to the method previously described for the preparation of hydroxamic acid (Step 4 of Example 1). HPLC: 77.1%; $t_R$=(LC/PDA: Phenomenex Luna C18 2.0× 150 mm 5μ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 1.46 min. $^1$H NMR (400 MHz, DMSO-$d_6$) δ 1.11 (6H, s), 2.90 (3H, s), 2.91 (3H, s), 3.12 (2H, s), 3.82 (2H, s), 4.79 (2H, s), 6.56 (1H, d, J=15.80 Hz), 7.15-7.32 (5H, m), 7.59-7.66 (2H, m), 7.87 (1H, d, J=8.68 Hz), 8.06(1H, s). MS (m/z): 455 [MH]$^+$.

EXAMPLE 59

Preparation of N-Hydroxy-3-(2-benzyl-1-ethyl-1H-benzimidazol-5-yl)-acrylamide (92)

The titled compound (92) was prepared according to the procedures described in Example 42, by using appropriate starting materials. HPLC: 97.0%; $t_R$=(LC/PDA: Phenomenex Luna C18 2.0×150 mm 5µ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 1.60 min. $^1H$ NMR (400 MHz, DMSO-$d_6$) δ 1.17 (3H, t, J=7.1 Hz), 4.34 (2H, dd, J=6.8 Hz), 4.56 (2H, s), 6.55 (1H, d, J=15.8 Hz), 7.31-7.40 (5H, m), 7.63 (1H, d, J=15.8 Hz), 7.85-7.93 (3H, m). MS (m/z): 322 [MH]$^+$.

EXAMPLE 60

Preparation of N-Hydroxy-3-{1-ethyl-2-[3-(1H-indol-3-yl)-propyl]-1H-benzimidazol-5-yl)-acrylamide (93)

The titled compound (93) was prepared according to the procedures described in Example 42, by using appropriate starting materials. HPLC: 98.5%; $t_R$=(LC/PDA: Phenomenex Luna C18 2.0×150 mm 5µ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 1.98 min. $^1H$ NMR (400 MHz, DMSO-$d_6$) δ 1.33 (3H, t), 2.22 (2H, m), 2.87 (2H, t), 3.16 (2H, m), 4.37 (2H,m), 6.53 (1H,d), 6.98 (1H, m) 7.06 (1H,m) 7.19 (1H, s), 7.33 (1H.d), 7.54-7.88 (5H, d), 10.82 (2H, bs). MS (m/z): 389 [MH]$^+$.

EXAMPLE 61

Preparation of N-Hydroxy-3-(1-(3-dimethylamino-2,2-dimethyl-propyl)-2-[2-(3-methoxy-phenyl)-ethyl]-1H-benzimidazol-5-yl)-acrylamide (94)

The titled compound (94) was prepared according to the procedures described in Example 42, by using appropriate starting materials. HPLC: 99.7%; $t_R$=(LC/PDA: Phenomenex Luna C18 2.0×150 mm 5µ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 1.34 min. $^1H$ NMR (400 MHz, DMSO-$d_6$) δ 1.03 (6H, s), 2.90 (6H, s), 3.19 (2H, t), 3.34 (4H, s) 3.71 (3H, s) 4.29 (2H, t), 6.52 (1H,d), 6.80 (1H, m) 6.88 (2H, d) 7.22 (1H, m), 7.62 (2H.m), 7.83-7.89 (2H, m), 9.34 (1H, s), 10.77 (1H, bs). MS (m/z): 451 [MH]$^+$.

EXAMPLE 62

Preparation of N-Hydroxy-3-[1-ethyl-2-(3-phenoxy-propyl)-1H-benzimidazol-5-yl]-acrylamide (96)

The titled compound (96) was prepared according to the procedures described in Example 46, by using appropriate starting materials. HPLC: 99.6%; $t_R$=(LC/PDA: Phenomenex Luna C18 2.0×150 mm 5µ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 1.83 min. $^1H$ NMR (400 MHz, DMSO-$d_6$) δ 1.36 (3H, t), 2.32 (2H, m), 3.34 (2H, m), 4.12 (2H, m), 4.46 (2H,m), 6.58 (1H,d), 6.73 (2H, d) 6.90 (1H,m) 7.22 (2H, m), 7.65 (1H.d), 7.80 (1H, d), 7.94 (2H, m). MS (m/z): 366 [MH]$^+$.

EXAMPLE 63

Preparation of N-Hydroxy-3-(2-{[2-(4-methoxy-phenyl)-acetylamino]-methyl}-1-methyl-H-benzimidazol-5-yl)-acrylamide (99)

The titled compound (99) was prepared according to the procedures described in Example 42, by using appropriate starting materials. HPLC: 97.0%; $t_R$=(LC/PDA: Phenomenex Luna C18 2.0×150 mm 5µ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 2.75 min. $^1H$ NMR (400 MHz, DMSO-$d_6$) δ 3.48 (2H, s), 3.67 (3H, s), 3.87 (3H, s), 4.71 (2H, m), 6.55 (1H,d), 6.86 (3H, m) 7.18 (3H, m) 7.84-7.92 (2H, m), 10.77 (1H, s). MS (m/z): 395 [MH]$^+$.

EXAMPLE 64

Preparation of 2-(1-Methyl-2-phenethyl-1H-benzimidazol-5-yl)-cyclopropanecarboxylic acid hydroxyamide (100)

The titled compound (100) was prepared according to the procedures described in Example 56, by using appropriate starting materials. HPLC: 99%; $t_R$=(LC/PDA: Phenomenex Luna C18 2.0×150 mm 5µ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 6.36 min $^1H$ NMR (400 MHz, CDCl$_3$, with one drop of $d_6$-DMSO-$d_6$) δ 1.25 (1H, m), 1.64 (1H, m), 1.88 (1H, m), 1.98 (3H, s), 2.63 (1H, m), 3.23 (2H, t, J=8.0 Hz), 3.52 (2H, t, J=8.0 Hz), 7.08-7.45 (7H, m), 7.57 (1H, s). MS (m/z): 336 [MH]$^+$.

EXAMPLE 65

Preparation of N-Hydroxy-3-(1-methyl-1H-benzimidazol-5-yl)-acrylamide (49)

The titled compound (49) was prepared according to the procedures described in Example 1, by using appropriate starting materials. HPLC: 99%; $t_R$=(LC/PDA: Phenomenex Luna C18 2.0×150 mm 5µ column; 0.8 mL/min, gradient 5-65% B over 15.5 min, Solvent A: $H_2O$ with 0.1% trifluoroacetic acid; Solvent B: Acetonitrile with 0.1% trifluoroacetic acid; UV 254): 1.05 min. $^1H$ NMR: (400 MHz, CD$_3$OD) δ 4.05 (3H, s), 6.52 (1H, d, J=15.8 Hz), 7.62 (1H, d, J=15.8 Hz), 7.77-7.89 (3H, m), 9.19 (1H, s). MS (m/z): 218 [MH]$^+$.

The following compounds are some representative examples prepared by methods disclosed or analogous to those disclosed in above Examples 1-65:

TABLE 1

| Compound | Structures | m/z [MH]+ |
|---|---|---|
| 1 | 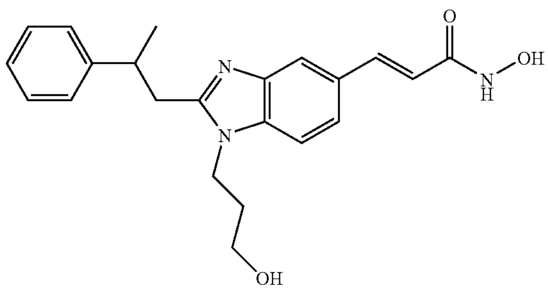 | 380 |
| 2 | 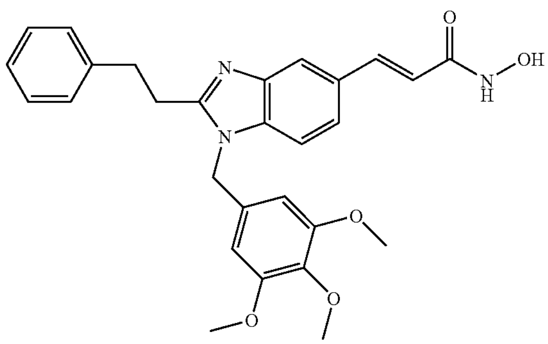 | 488 |
| 3 | 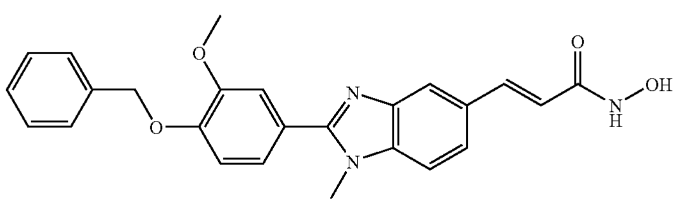 | 431 |
| 4 | 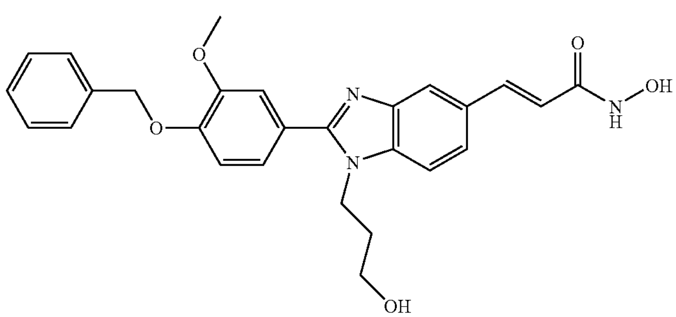 | 474 |
| 5 | 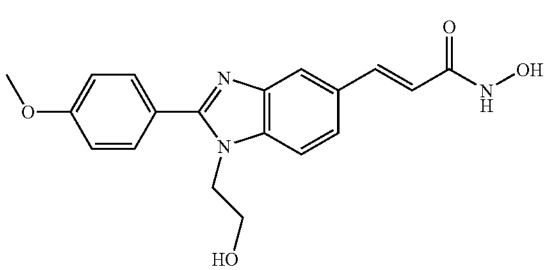 | 354 |

TABLE 1-continued

| Compound | Structures | m/z [MH]+ |
|---|---|---|
| 6 | 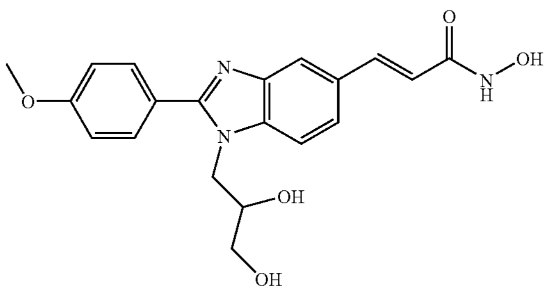 | 383 |
| 7 | 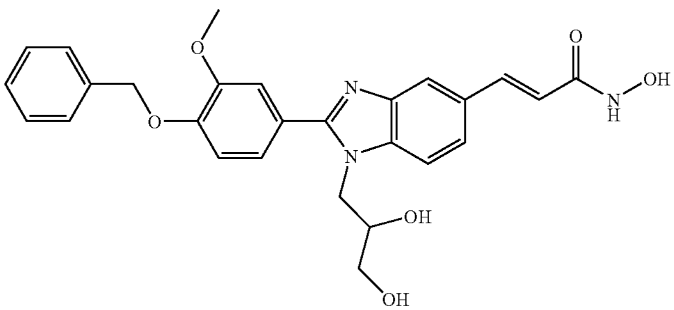 | 490 |
| 8 | 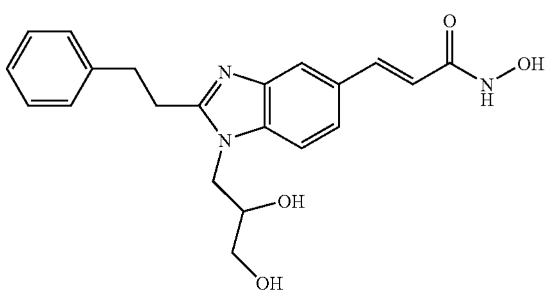 | 382 |
| 9 | 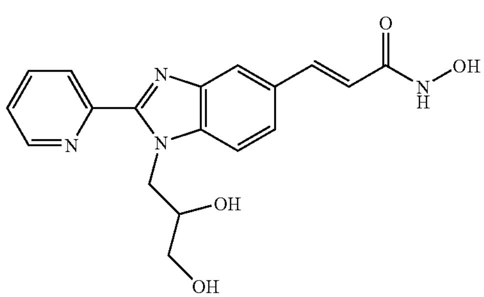 | 355 |
| 10 | 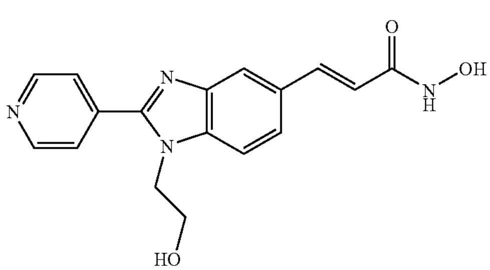 | 325 |

TABLE 1-continued

| Compound | Structures | m/z [MH]+ |
|---|---|---|
| 11 | 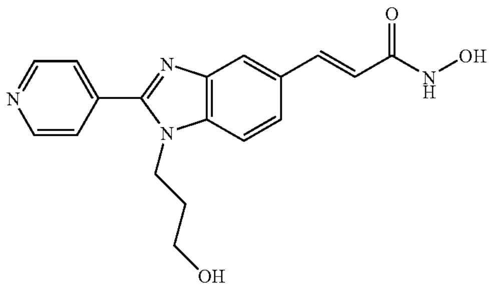 | 339 |
| 12 | 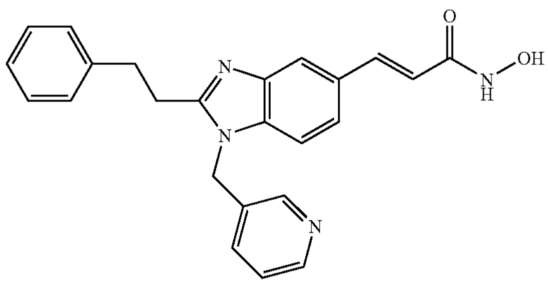 | 399 |
| 13 | 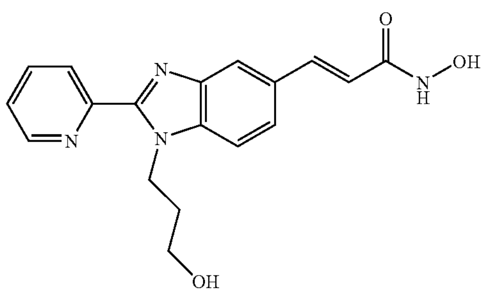 | 339 |
| 14 | 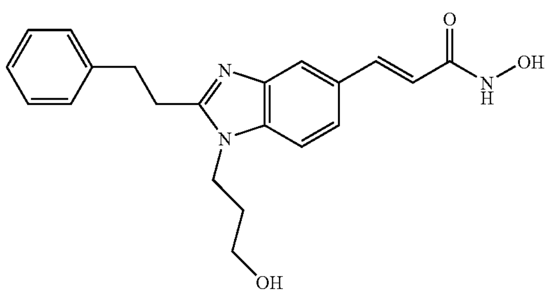 | 366 |
| 15 | 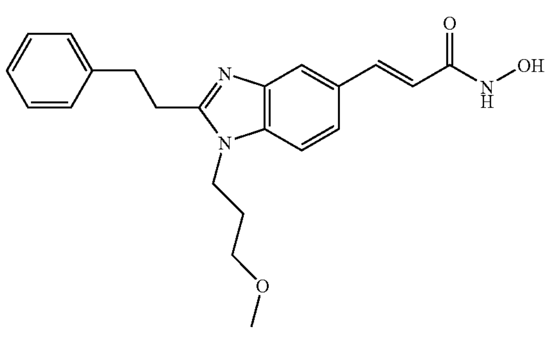 | 380 |

TABLE 1-continued
| Compound | Structures | m/z [MH]+ |
|---|---|---|
| 16 | 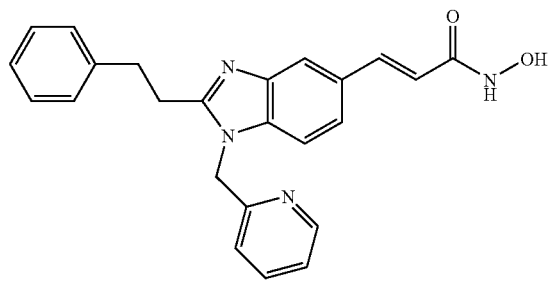 | 399 |
| 17 | 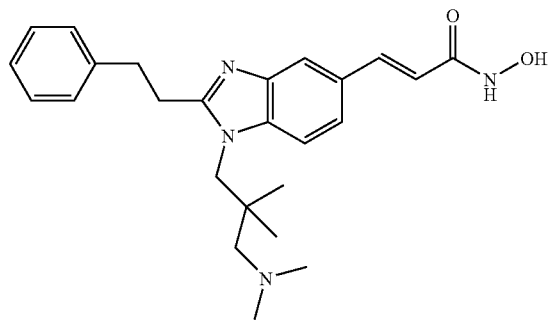 | 421 |
| 18 | 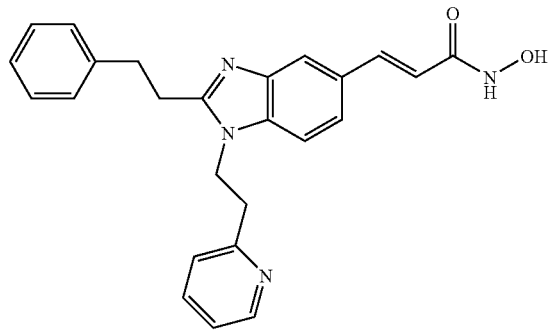 | 413 |
| 19 | 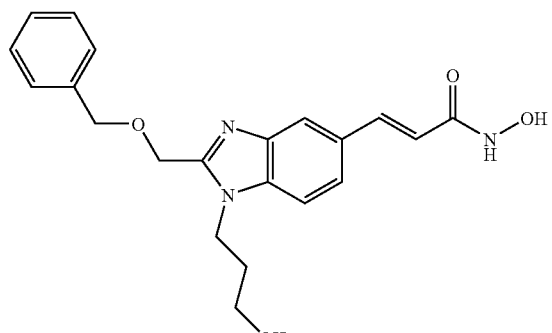 | 382 |

TABLE 1-continued

| Compound | Structures | m/z [MH]+ |
|---|---|---|
| 20 | 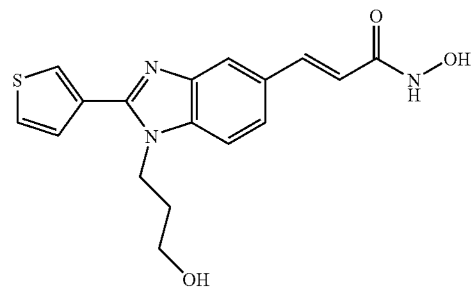 | 344 |
| 21 | 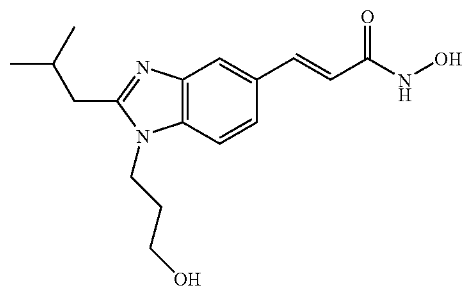 | 318 |
| 22 | 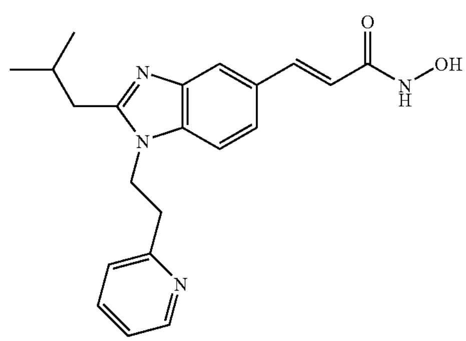 | 365 |
| 23 | 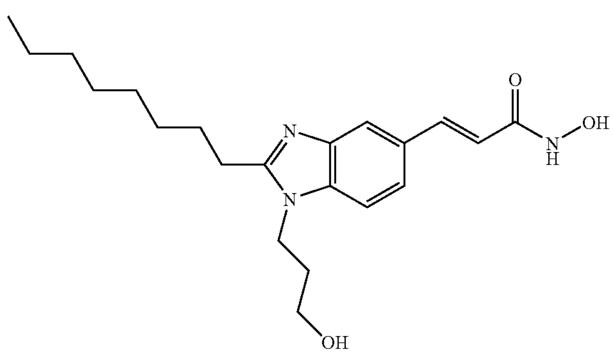 | 374 |
| 24 | 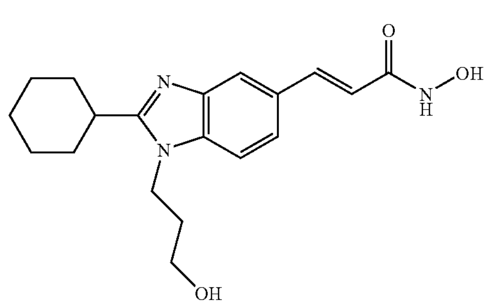 | 344 |

TABLE 1-continued

| Compound | Structures | m/z [MH]+ |
|---|---|---|
| 25 | 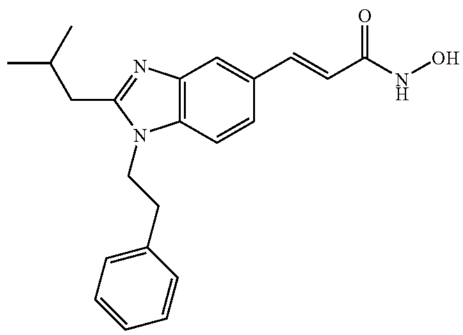 | 364 |
| 26 | 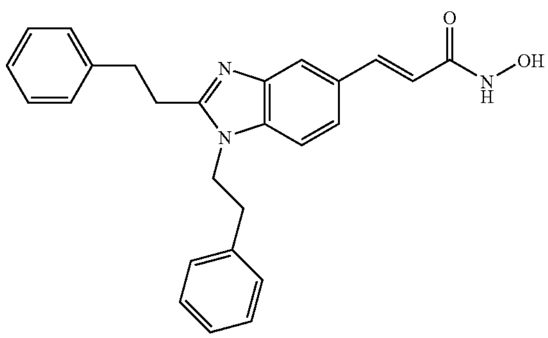 | 412 |
| 27 | 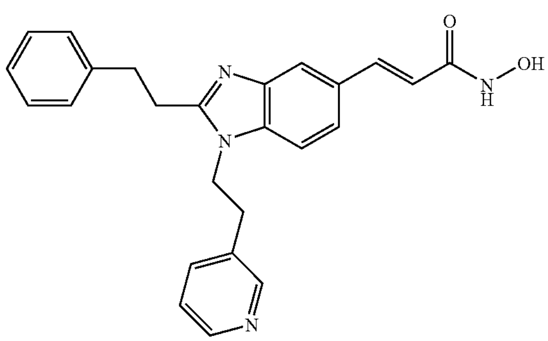 | 413 |
| 28 | 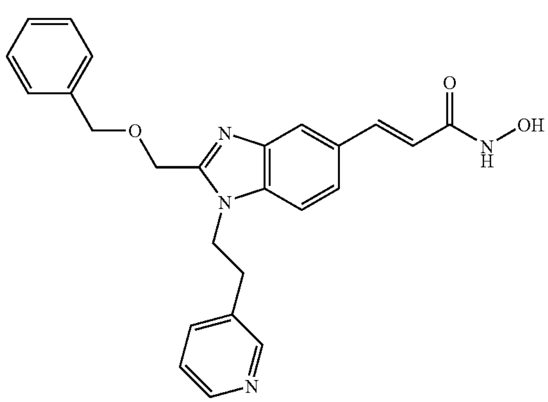 | 429 |

TABLE 1-continued
| Compound | Structures | m/z [MH]+ |
|---|---|---|
| 29 | 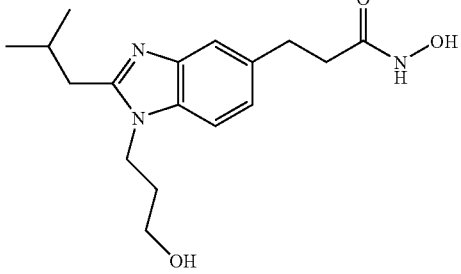 | 320 |
| 30 | 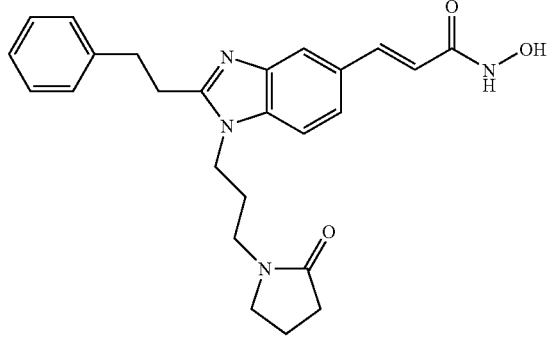 | 433 |
| 31 | 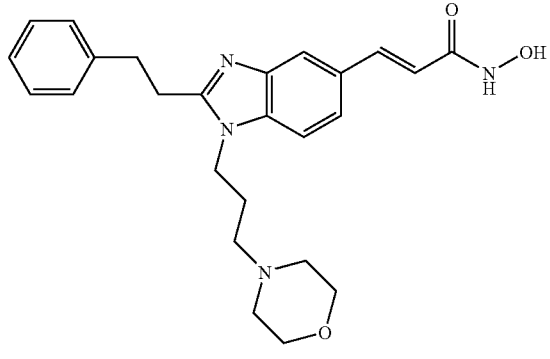 | 435 |
| 32 | 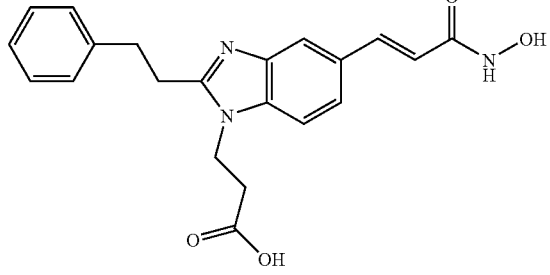 | 380 |

TABLE 1-continued

| Compound | Structures | m/z [MH]+ |
|---|---|---|
| 33 | 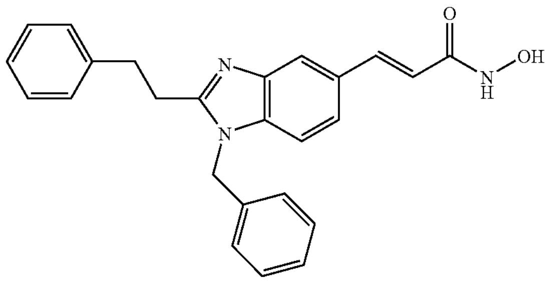 | 398 |
| 34 | 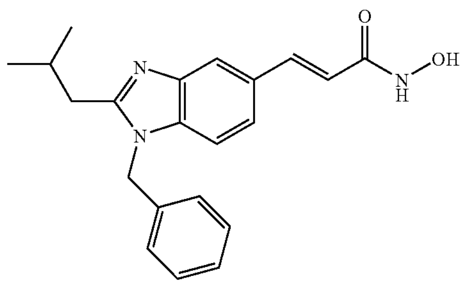 | 350 |
| 35 | 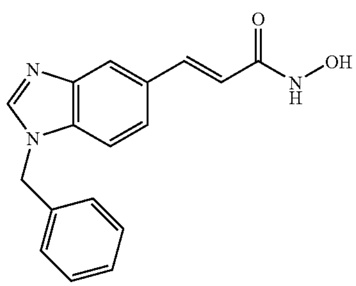 | 294 |
| 36 | 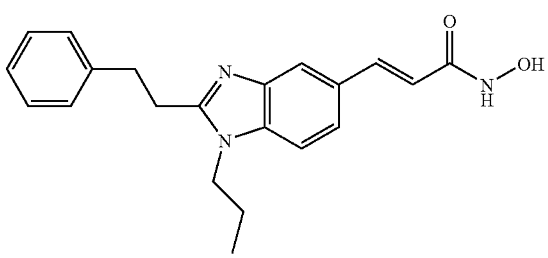 | 350 |
| 37 | 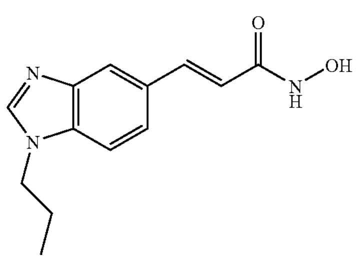 | 246 |
| 38 | 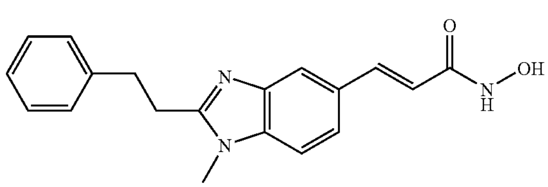 | 336 |

TABLE 1-continued

| Compound | Structures | m/z [MH]+ |
|---|---|---|
| 39 | 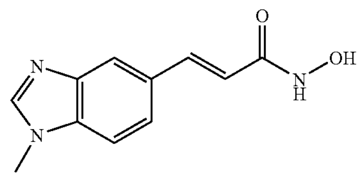 | 232 |
| 40 | 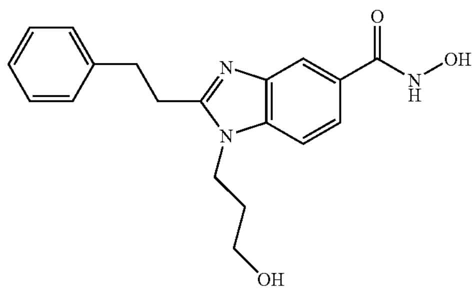 | 340 |
| 41 | 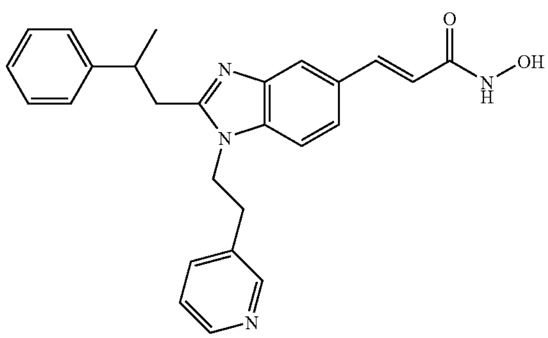 | 427 |
| 42 | 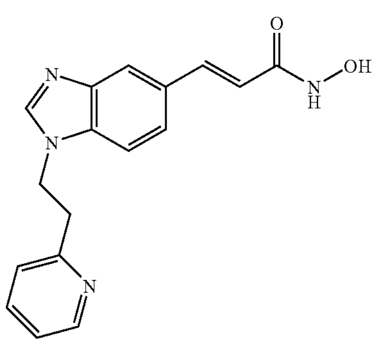 | 309 |
| 43 | 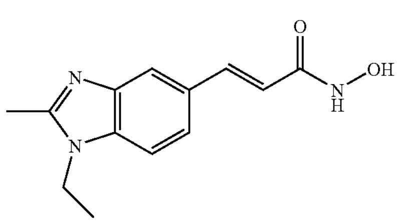 | 246 |

TABLE 1-continued

| Compound | Structures | m/z [MH]+ |
|---|---|---|
| 44 | 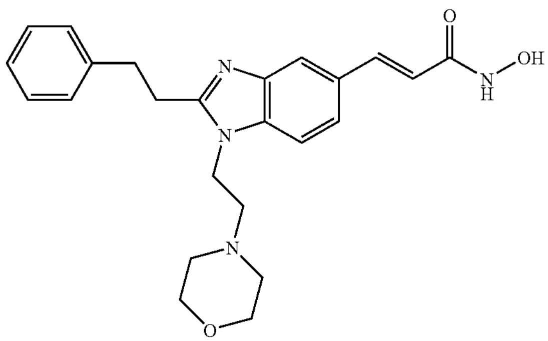 | 421 |
| 45 | 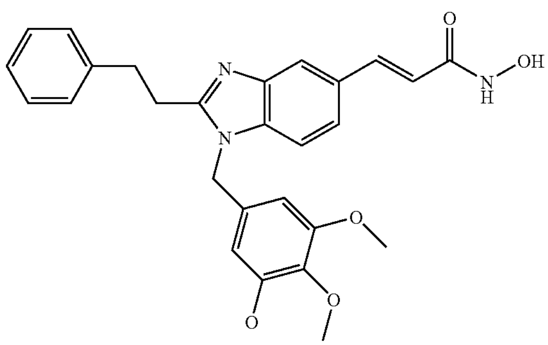 | 490 |
| 46 | 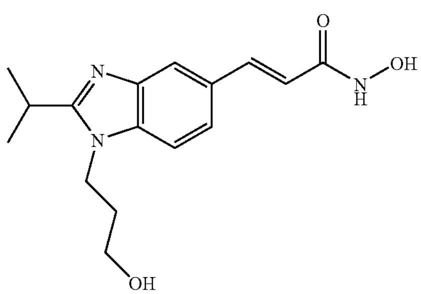 | 304 |
| 47 | 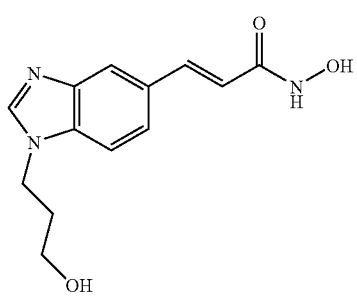 | 262 |
| 48 | 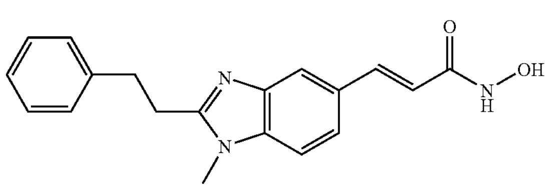 | 322 |

TABLE 1-continued
| Compound | Structures | m/z [MH]+ |
|---|---|---|
| 49 | 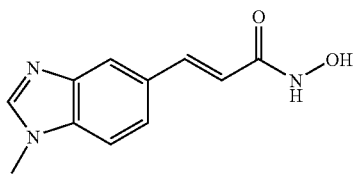 | 218 |
| 50 | 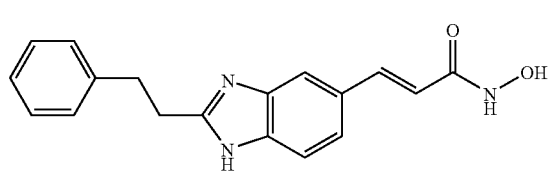 | 308 |
| 51 | 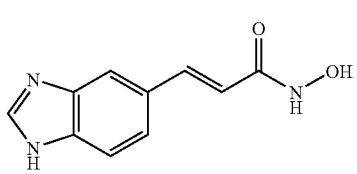 | 204 |
| 52 | 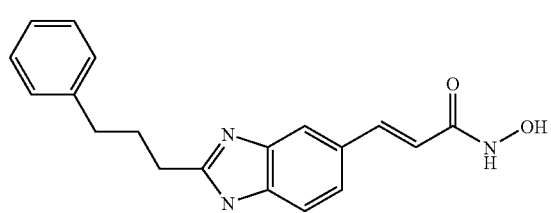 | 336 |
| 53 | 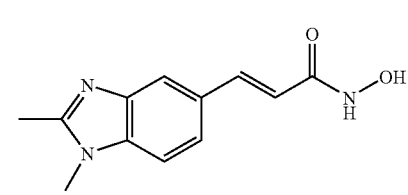 | 232 |
| 54 | 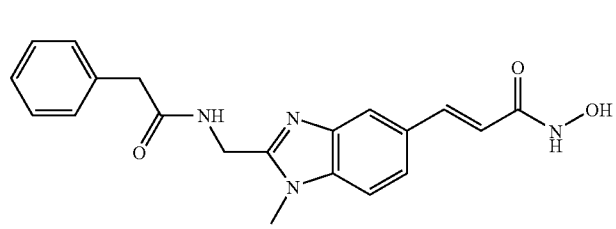 | 365 |
| 55 | 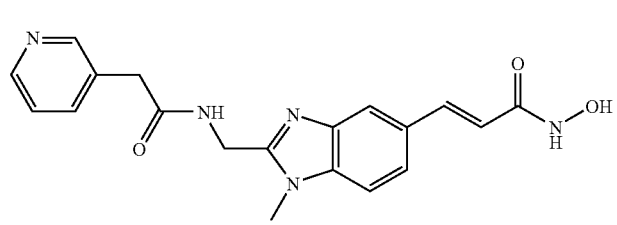 | 352 |

TABLE 1-continued
| Compound | Structures | m/z [MH]+ |
|---|---|---|
| 56 | 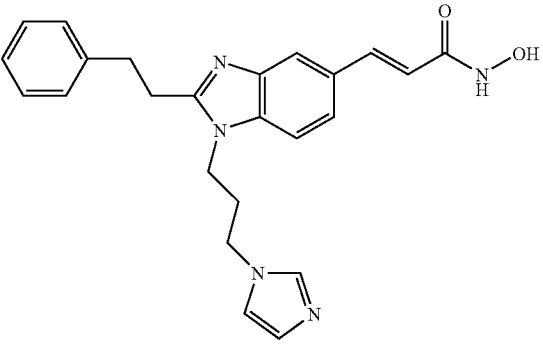 | 416 |
| 57 | 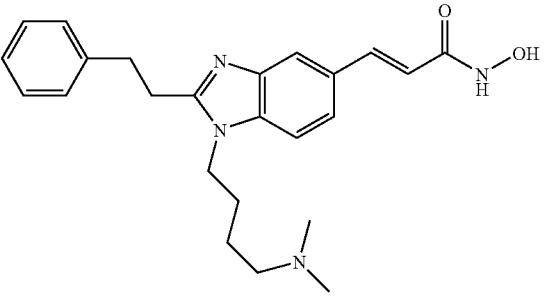 | 407 |
| 58 | 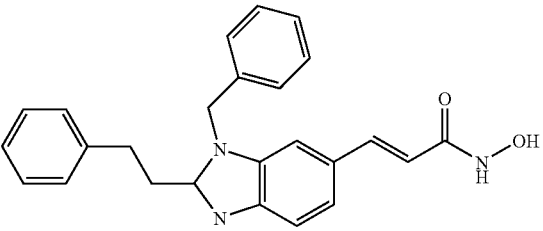 | 398 |
| 59 | 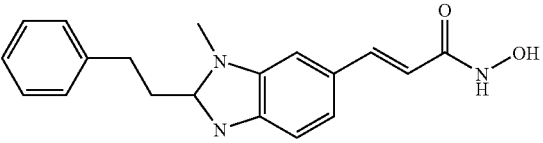 | 322 |
| 60 | 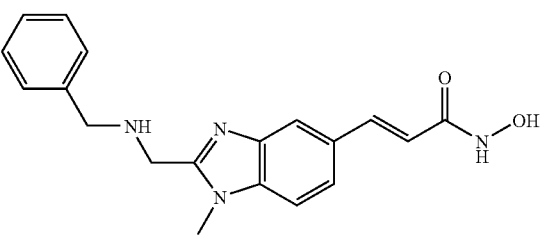 | 337 |
| 61 | 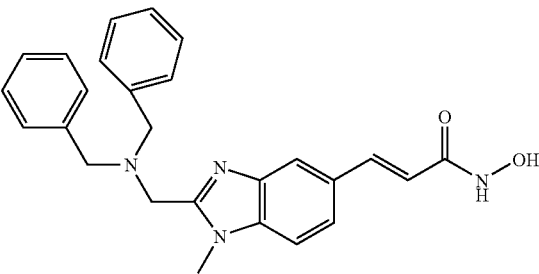 | 427 |

TABLE 1-continued

| Compound | Structures | m/z [MH]+ |
|---|---|---|
| 62 | 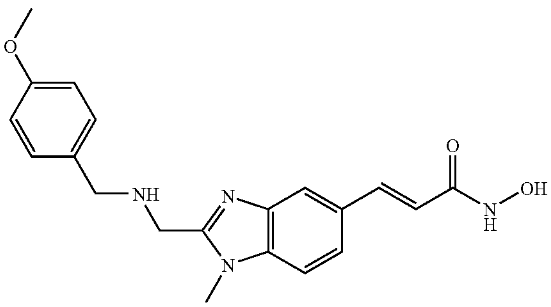 | 367 |
| 63 | 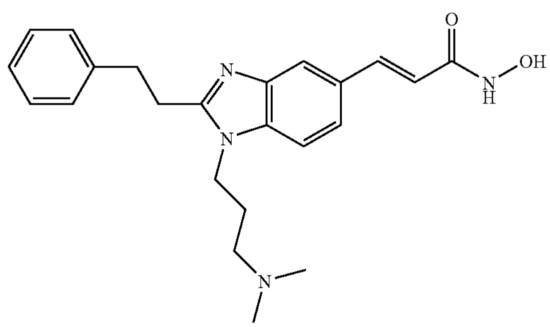 | 393 |
| 64 | 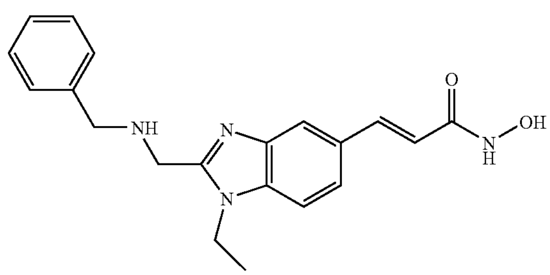 | 351 |
| 65 | 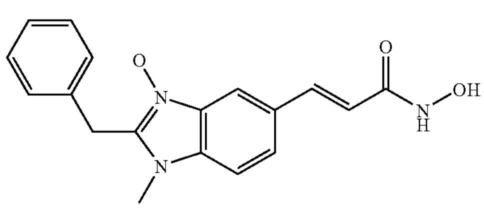 | 309 |
| 66 | 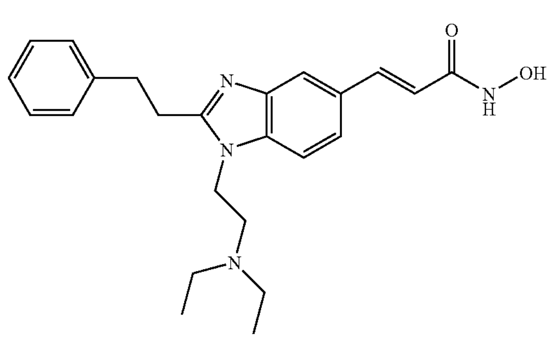 | 407 |

TABLE 1-continued

| Compound | Structures | m/z [MH]+ |
|---|---|---|
| 67 | 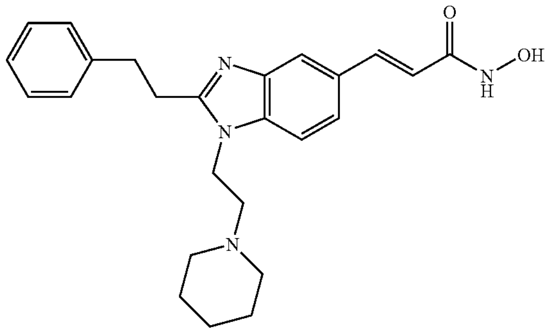 | 419 |
| 68 | 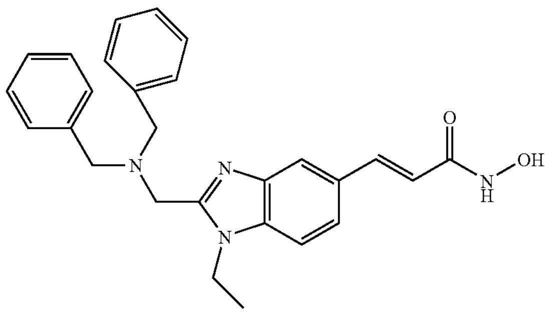 | 441 |
| 69 | 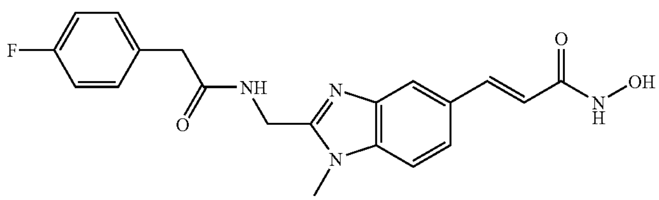 | 383 |
| 70 | 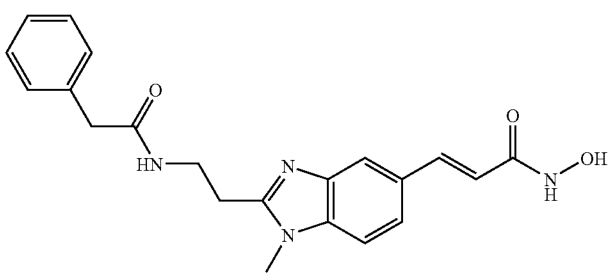 | 393 |
| 71 | 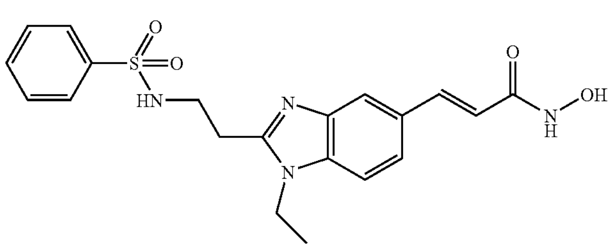 | 415 |

TABLE 1-continued
| Compound | Structures | m/z [MH]+ |
|---|---|---|
| 72 | 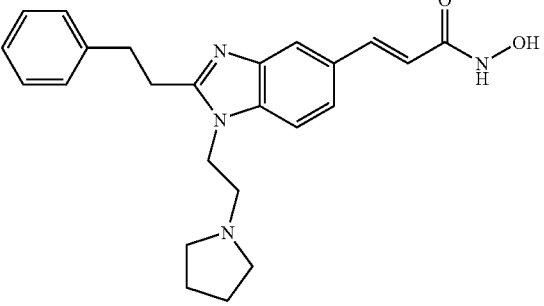 | 405 |
| 73 | 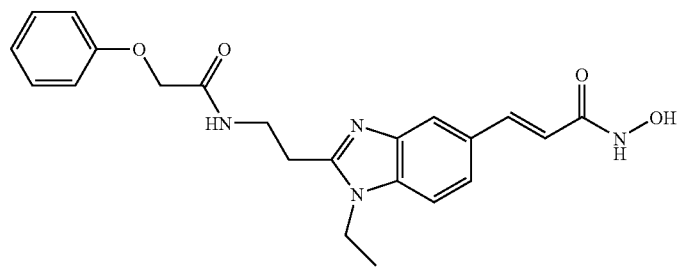 | 409 |
| 74 | 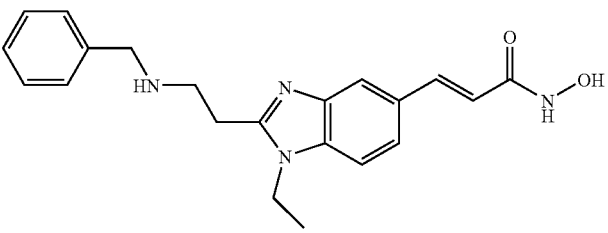 | 365 |
| 75 | 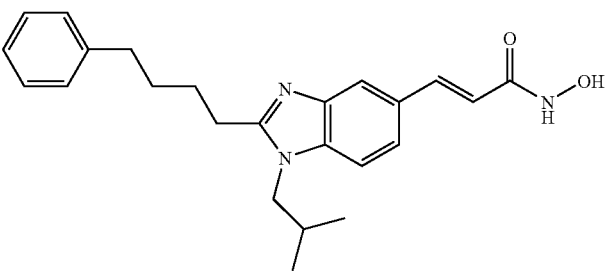 | 378 |
| 76 | 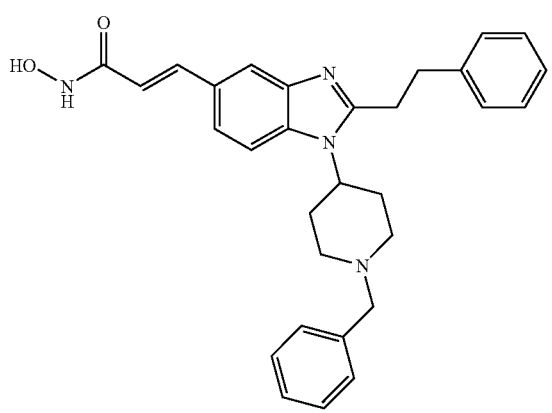 | 481 |

TABLE 1-continued
| Compound | Structures | m/z [MH]+ |
|---|---|---|
| 77 | 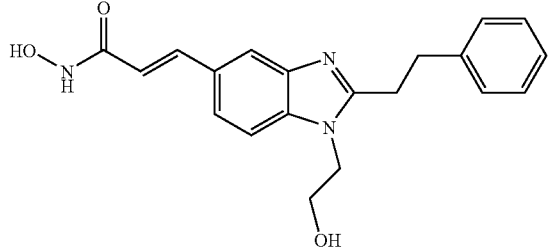 | 352 |
| 78 | 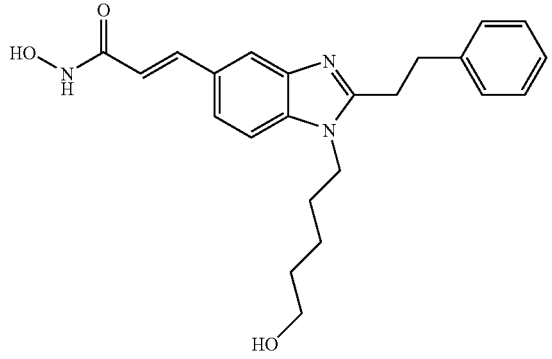 | 394 |
| 79 | 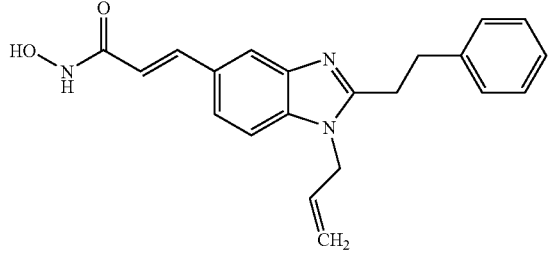 | 348 |
| 80 | 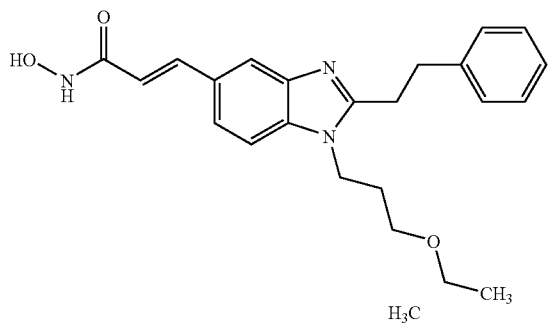 | 408 |

TABLE 1-continued

| Compound | Structures | m/z [MH]+ |
|---|---|---|
| 81 | 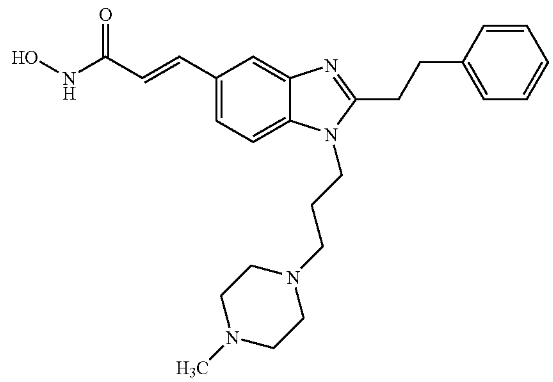 | 448 |
| 82 | 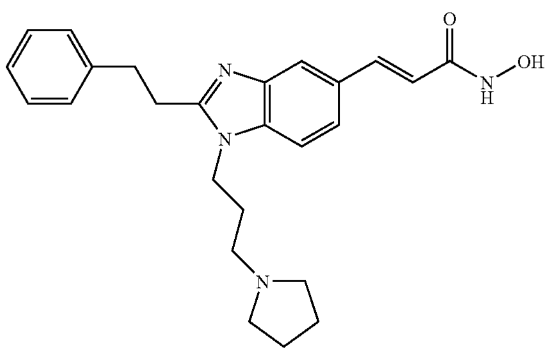 | 419 |
| 83 | 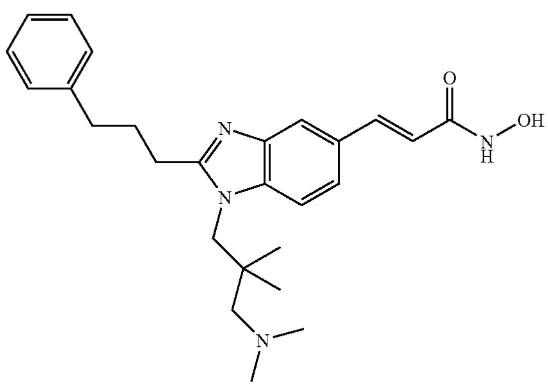 | 435 |
| 84 | 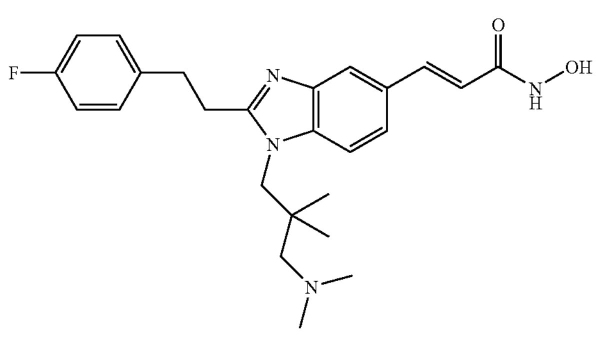 | 439 |

TABLE 1-continued

| Compound | Structures | m/z [MH]+ |
|---|---|---|
| 85 | 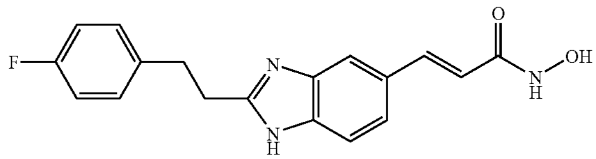 | 326 |
| 86 | 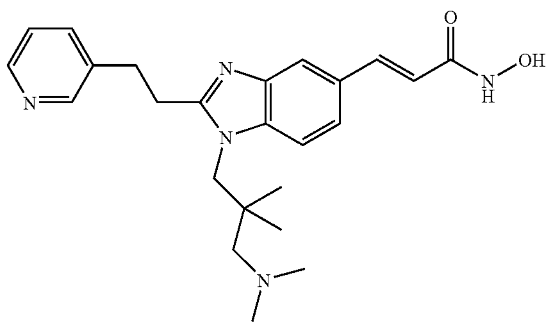 | 422 |
| 87 | 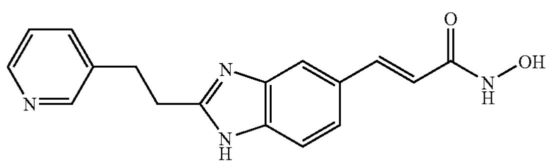 | 309 |
| 88 | 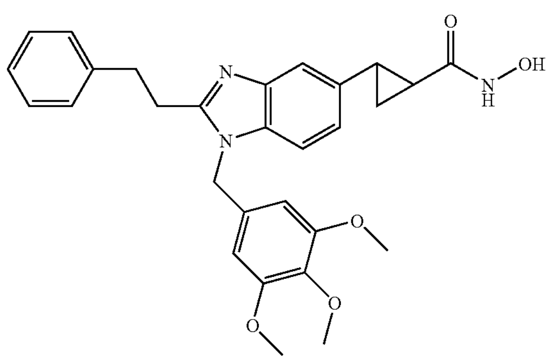 | 502 |
| 89 | 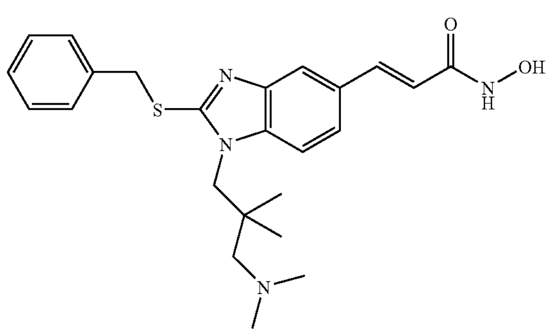 | 439 |

TABLE 1-continued

| Compound | Structures | m/z [MH]+ |
|---|---|---|
| 90 | 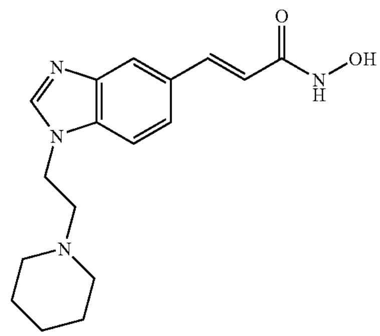 | 315 |
| 91 | 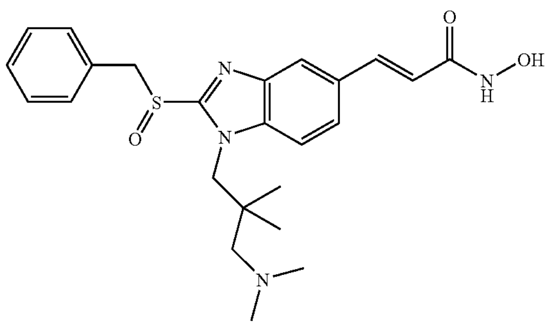 | 455 |
| 92 | 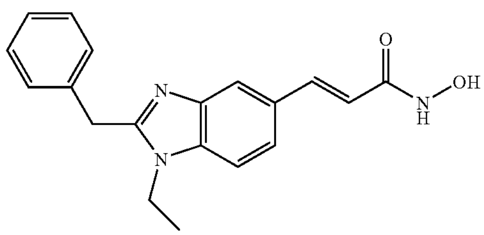 | 322 |
| 93 | 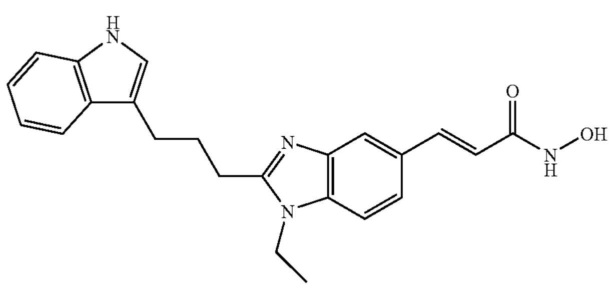 | 389 |
| 94 | 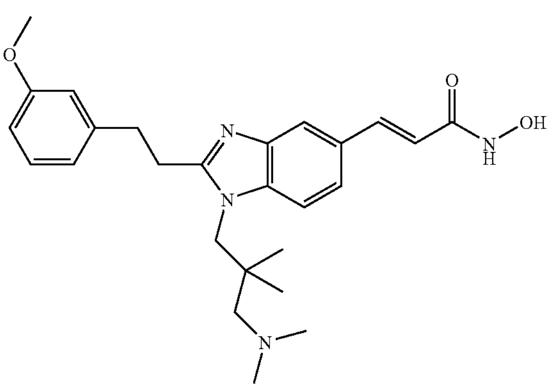 | 451 |

TABLE 1-continued

| Compound | Structures | m/z [MH]+ |
|---|---|---|
| 95 | 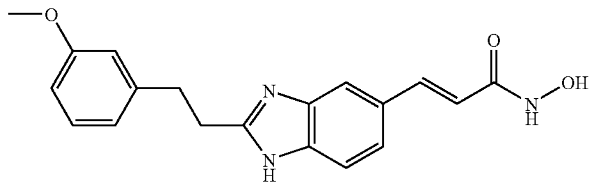 | 338 |
| 96 | 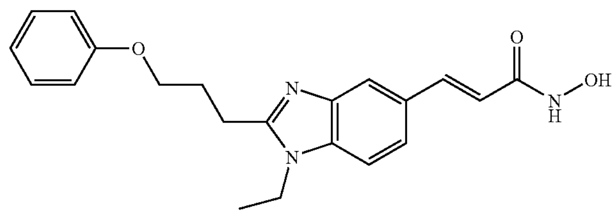 | 366 |
| 97 | 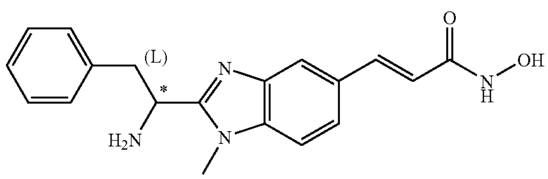 | 336 |
| 98 | 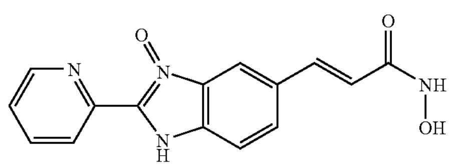 | 297 |
| 99 | 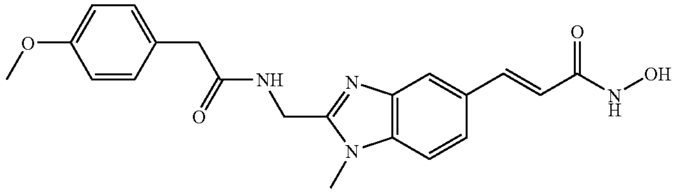 | 395 |
| 100 | 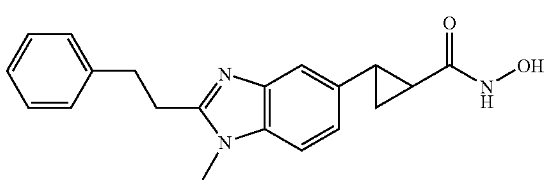 | 336 |

By methods analogous to those disclosed above, a wide variety of compounds of Formula I could be prepared, including, but not limited to, those in Table 2(a):

TABLE 2(a)

| 101 | | N-Hydroxy-3-[1-methyl-2-(2-piperidin-1-yl-ethyl)-1H-benzimidazol-5-yl]-acrylamide |
|---|---|---|

TABLE 2(a)-continued

| # | Name |
|---|---|
| 102 | N-Hydroxy-3-[2-(2-diethylamino-ethyl)-1-methyl-1H-benzimidazol-5-yl]-acrylamide |
| 103 | N-Hydroxy-3-[2-(2-cyclohexyl-ethyl)-1-(2-pyridin-1-yl-ethyl)-1H-benzimidazol-5-yl]-acrylamide |
| 104 | N-Hydroxy-N-methyl-3-[2-(2-cyclohexyl-ethyl)-1-(2-pyrrolidin-1-yl-ethyl)-1H-benzimidazol-5-yl]-acrylamide |
| 105 | N-Hydroxy-[2-(2-cylohexyl-ethyl)-1-methyl-1H-benzimidazol-5-yl]-acrylamide |
| 106 | N-Hydroxy-[2-(2-cyclopenthyl-ethyl)-1-(2-pyrrolidin-1-yl-ethyl)-1H-benzimidazol-5-yl]-acrylamide |
| 107 | N-Hydroxy-3-[1-methyl-2-(2-pyrrolidin-1-yl-ethyl)-1H-benzimidazol-5-yl]-acrylamide |

TABLE 2(a)-continued

| | | |
|---|---|---|
| 108 | | (L)-N-Hydroxy-3-[2-(1-benzylamino-2-phenyl-ethyl)-1-methyl-1H benzimidazol-5-yl]-acrylamide |
| 109 | | N-Hydroxy-3-[2-benzyloxy-1-(2-pyrrolidin-1-ethyl)-1H-benzimidazol-5-yl]-acrylamide |
| 110 | | N-Hydroxy-3-(2-benzylsulfanyl-1-methyl-1H-benzimidazol-5-yl)-acrylamide |
| 111 | | N-Hydroxy-3-[2-phenethylamino-1-(2-pyrrolidin-1-yl-ethyl)-1H-benzimidazol-5-yl]-acrylamide |
| 112 | | N-Hydroxy-3-(1-methyl-2-quinolin-3-ylmethyl-1H-benzimdazol-5-yl)-acrylamide |

TABLE 2(a)-continued

| | | |
|---|---|---|
| 113 | 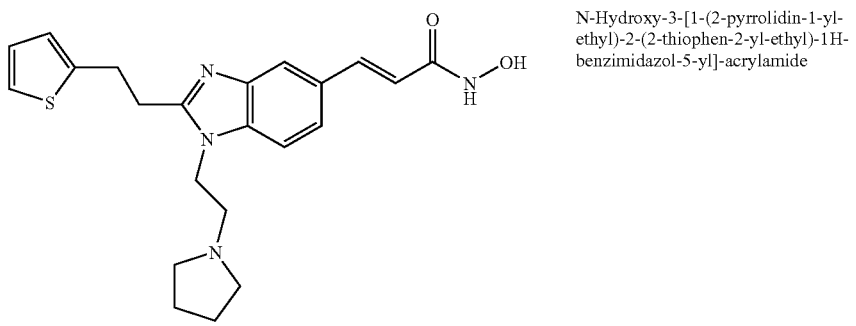 | N-Hydroxy-3-[1-(2-pyrrolidin-1-yl-ethyl)-2-(2-thiophen-2-yl-ethyl)-1H-benzimidazol-5-yl]-acrylamide |
| 114 | 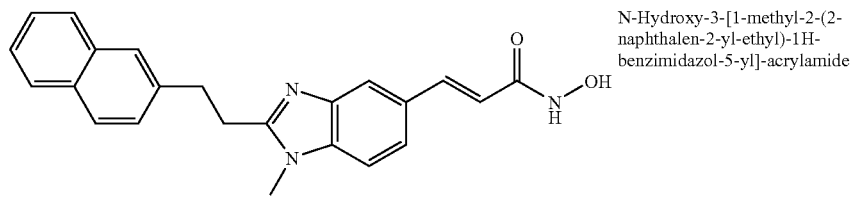 | N-Hydroxy-3-[1-methyl-2-(2-naphthalen-2-yl-ethyl)-1H-benzimidazol-5-yl]-acrylamide |
| 115 | 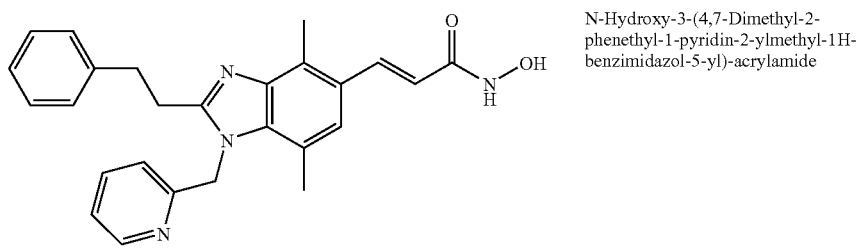 | N-Hydroxy-3-(4,7-Dimethyl-2-phenethyl-1-pyridin-2-ylmethyl-1H-benzimidazol-5-yl)-acrylamide |
| 116 | 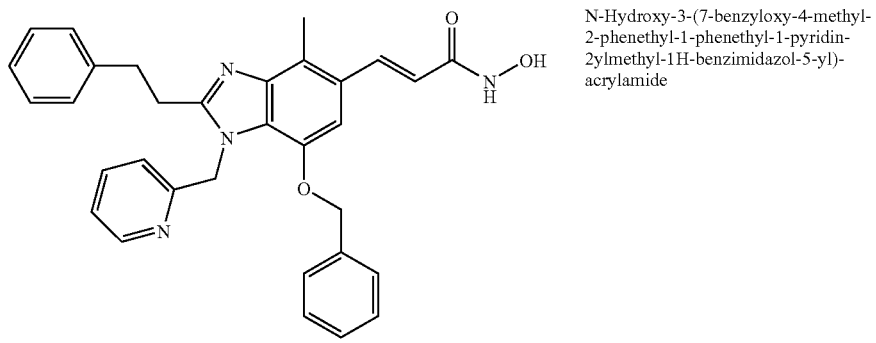 | N-Hydroxy-3-(7-benzyloxy-4-methyl-2-phenethyl-1-phenethyl-1-pyridin-2ylmethyl-1H-benzimidazol-5-yl)-acrylamide |
| 117 | 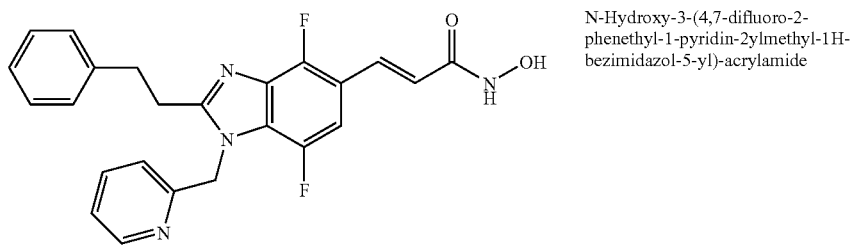 | N-Hydroxy-3-(4,7-difluoro-2-phenethyl-1-pyridin-2ylmethyl-1H-bezimidazol-5-yl)-acrylamide |

By methods analogous to those disclosed above and by varying the starting materials used in the synthesis, a wide variety of compounds of Formula I could be prepared, including, but not limited to, those in Table 2(b):

TABLE 2(B)

| | R₁ | R₂ | R₃ | R₄ | X | Y |
|---|---|---|---|---|---|---|
| 118 | H | 2-cyclopentylethyl | H | H | H | CH₃ |
| 119 | H | 1-methyl-2-phenylethyl(benzyl)amino | CH₃ | H | F | OCH₃ |
| 120 | H | 2-(pyridin-2-yl)ethyl | H | CH₃ | Cl | CH₃ |
| 121 | H | cyclohexylmethyl-A- (A = C, N, O, S) | CH₃ | CH₃ | Br | H |
| 122 | H | 2-(pyrrolidin-1-yl)ethyl | H | H | CH₃ | F |
| 123 | H | 3-(diethylamino)propyl | CH₃ | H | OCH₃ | Cl |
| 124 | Propyl | 2-cyclohexyl-1-(dimethylamino)ethyl | H | CH₃ | CF₃ | Br |
| 125 | Propyl | 1-(dimethylamino)-1-methyl-2-phenylethyl | CH₃ | CH₃ | CN | CH₃ |

TABLE 2(B)-continued
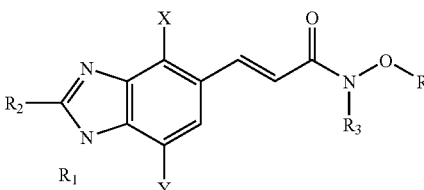
| | R₁ | R₂ | R₃ | R₄ | X | Y |
|---|---|---|---|---|---|---|
| 126 | Propyl | 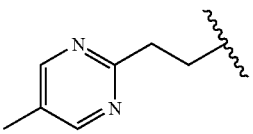 | H | H | OCF₃ | OCH₃ |
| 127 | Propyl | 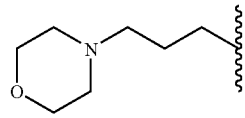 | CH₃ | H | NO₂ | CF₃ |
| 128 | Propyl | 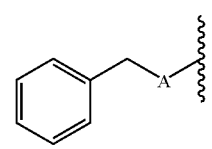<br>A = C, N, O, S | H | CH₃ | CH₃ | CN |
| 129 | Propyl | 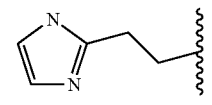 | CH₃ | CH₃ | OCH₃ | OCF₃ |
| 130 | Propyl | 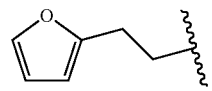 | H | H | F | NO₂ |
| 131 | Propyl | 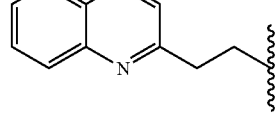 | CH₃ | H | CH₃ | CH₃ |
| 132 | 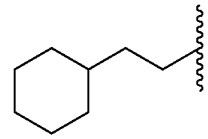 | 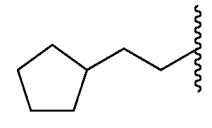 | H | CH₃ | OCH₃ | OCH₃ |
| 133 | 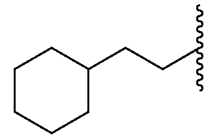 | 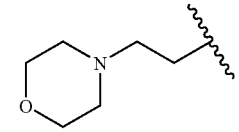 | CH₃ | CH₃ | F | H |
| 134 | 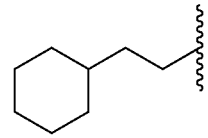 | 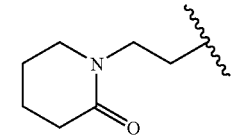 | H | H | CH₃ | F |

TABLE 2(B)-continued
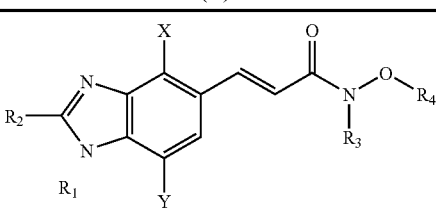
| | R₁ | R₂ | R₃ | R₄ | X | Y |
|---|---|---|---|---|---|---|
| 135 | 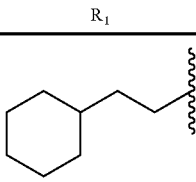 | 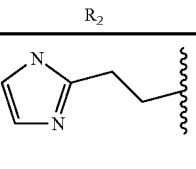 | CH₃ | H | OCH₃ | Cl |
| 136 | 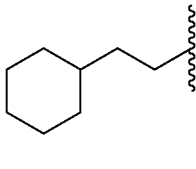 | 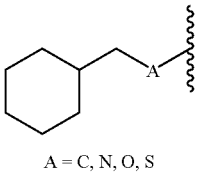<br>A = C, N, O, S | H | CH₃ | F | Br |
| 137 | 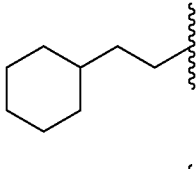 | 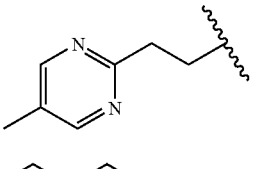 | CH₃ | CH₃ | CH₃ | CH₃ |
| 138 | 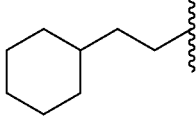 | 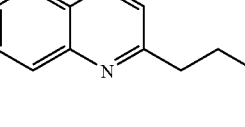 | H | H | CH₃ | OCH₃ |
| 139 | 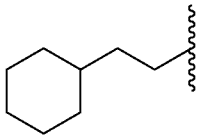 | 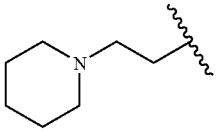 | CH₃ | H | OCH₃ | CF₃ |
| 140 | 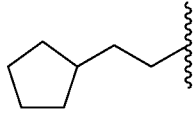 | 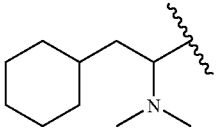 | H | CH₃ | F | CN |
| 141 | 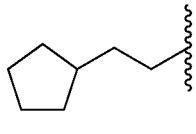 | 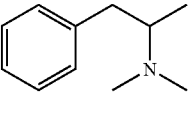 | CH₃ | CH₃ | F | OCF₃ |
| 142 | 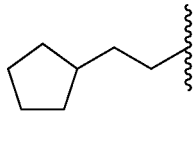 | 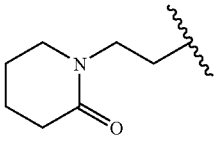 | H | H | Cl | NO₂ |
| 143 | 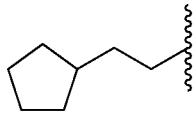 | 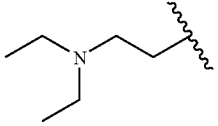 | CH₃ | H | Br | F |

TABLE 2(B)-continued
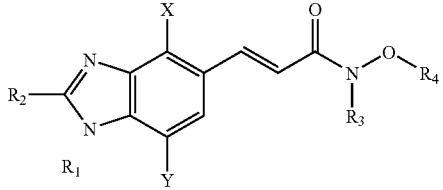
| | R₁ | R₂ | R₃ | R₄ | X | Y |
|---|---|---|---|---|---|---|
| 144 | 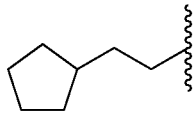 | 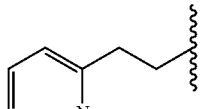 | H | CH₃ | CH₃ | CH₃ |
| 145 | 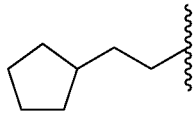 | 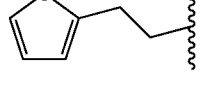 | CH₃ | CH₃ | OCH₃ | OCH₃ |
| 146 | 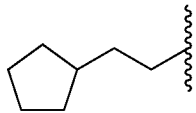 | 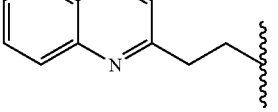 | H | H | CF₃ | CH₃ |
| 147 | 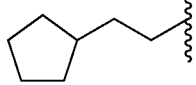 | 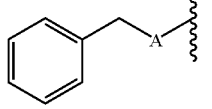  A = C, N, O, S | CH₃ | H | CN | H |
| 148 | 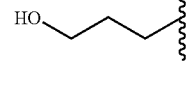 | 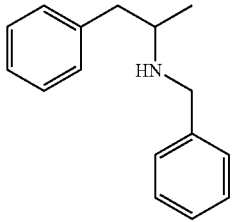 | H | CH₃ | OCF₃ | F |
| 149 | 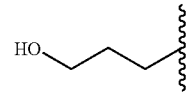 | 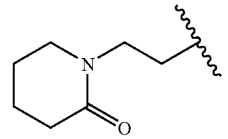 | CH₃ | CH₃ | NO₂ | Cl |
| 150 | 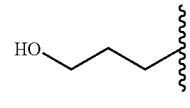 | 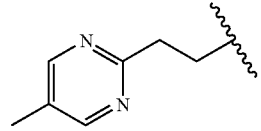 | H | H | CH₃ | Br |
| 151 | 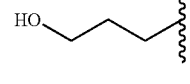 | 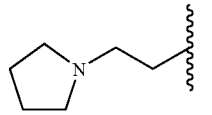 | CH₃ | H | CH₃ | CH₃ |

TABLE 2(B)-continued

| | R₁ | R₂ | R₃ | R₄ | X | Y |
|---|---|---|---|---|---|---|
| 152 | HO-(CH₂)₃-~ | quinolin-2-yl-CH₂CH₂-~ | H | CH₃ | OCH₃ | OCH₃ |
| 153 | HO-(CH₂)₃-~ | (Et)₂N-CH₂CH₂-~ | CH₃ | CH₃ | F | CF₃ |
| 154 | HO-(CH₂)₃-~ | piperidin-1-yl-CH₂CH₂-~ | H | H | CH₃ | CN |
| 155 | HO-(CH₂)₃-~ | morpholin-4-yl-CH₂CH₂CH₂-~ | CH₃ | H | OCH₃ | OCF₃ |
| 156 | CH₃O-(CH₂)₃-~ | cyclopentyl-CH₂CH₂-~ | H | CH₃ | CH₃ | NO₂ |
| 157 | CH₃O-(CH₂)₃-~ | PhCH₂CH(N(CH₃)₂)-~ | CH₃ | CH₃ | OCH₃ | CH₃ |
| 158 | CH₃O-(CH₂)₃-~ | morpholin-4-yl-CH₂CH₂CH₂-~ | H | H | F | F |
| 159 | CH₃O-(CH₂)₃-~ | quinolin-2-yl-CH₂CH₂-~ | CH₃ | H | H | CH₃ |
| 160 | CH₃O-(CH₂)₃-~ | imidazol-2-yl-CH₂CH₂-~ | H | CH₃ | F | OCH₃ |

TABLE 2(B)-continued

| # | R₁ | R₂ | R₃ | R₄ | X | Y |
|---|----|----|----|----|---|---|
| 161 | methoxypropyl | cyclohexylmethyl-A- (A = C, N, O, S) | CH₃ | CH₃ | Cl | CH₃ |
| 162 | methoxypropyl | benzyl-A- (A = C, N, O, S) | H | H | Br | H |
| 163 | methoxypropyl | 2-pyridylethyl | CH₃ | H | CH₃ | F |
| 164 | (5-methylpyrimidin-2-yl)ethyl | 1-phenyl-2-(dimethylamino)propyl | H | CH₃ | OCH₃ | Cl |
| 165 | (5-methylpyrimidin-2-yl)ethyl | 2-(thiophen-2-yl)ethyl | CH₃ | CH₃ | CF₃ | Br |
| 166 | (5-methylpyrimidin-2-yl)ethyl | 2-(quinolin-2-yl)ethyl | H | H | CN | CH₃ |
| 167 | (5-methylpyrimidin-2-yl)ethyl | 3-(2-oxopiperidin-1-yl)propyl | CH₃ | H | OCF₃ | OCH₃ |
| 168 | (5-methylpyrimidin-2-yl)ethyl | 1-phenyl-2-(benzylamino)propyl | H | CH₃ | NO₂ | CF₃ |

TABLE 2(B)-continued

| | R₁ | R₂ | R₃ | R₄ | X | Y |
|---|---|---|---|---|---|---|
| 169 | 5-methylpyrimidin-2-yl-methyl | furan-2-yl-methyl | CH₃ | CH₃ | CH₃ | CN |
| 170 | 5-methylpyrimidin-2-yl-methyl | quinolin-2-yl-methyl | H | H | OCH₃ | OCF₃ |
| 171 | 5-methylpyrimidin-2-yl-methyl | piperidin-1-yl-methyl | CH₃ | H | F | NO₂ |
| 172 | pyridin-2-yl-methyl | cyclopentyl-methyl | H | CH₃ | CH₃ | CH₃ |
| 173 | pyridin-2-yl-methyl | morpholin-4-yl-methyl | CH₃ | CH₃ | OCH₃ | H |
| 174 | pyridin-2-yl-methyl | quinolin-2-yl-methyl | H | H | H | F |
| 175 | pyridin-2-yl-methyl | pyridin-2-yl-methyl | CH₃ | H | F | Cl |
| 176 | pyrimidin-2-yl-methyl | quinolin-2-yl-methyl | H | CH₃ | Cl | Br |
| 177 | pyrimidin-2-yl-methyl | pyrrolidin-1-yl-methyl | CH₃ | CH₃ | Br | CH₃ |

TABLE 2(B)-continued

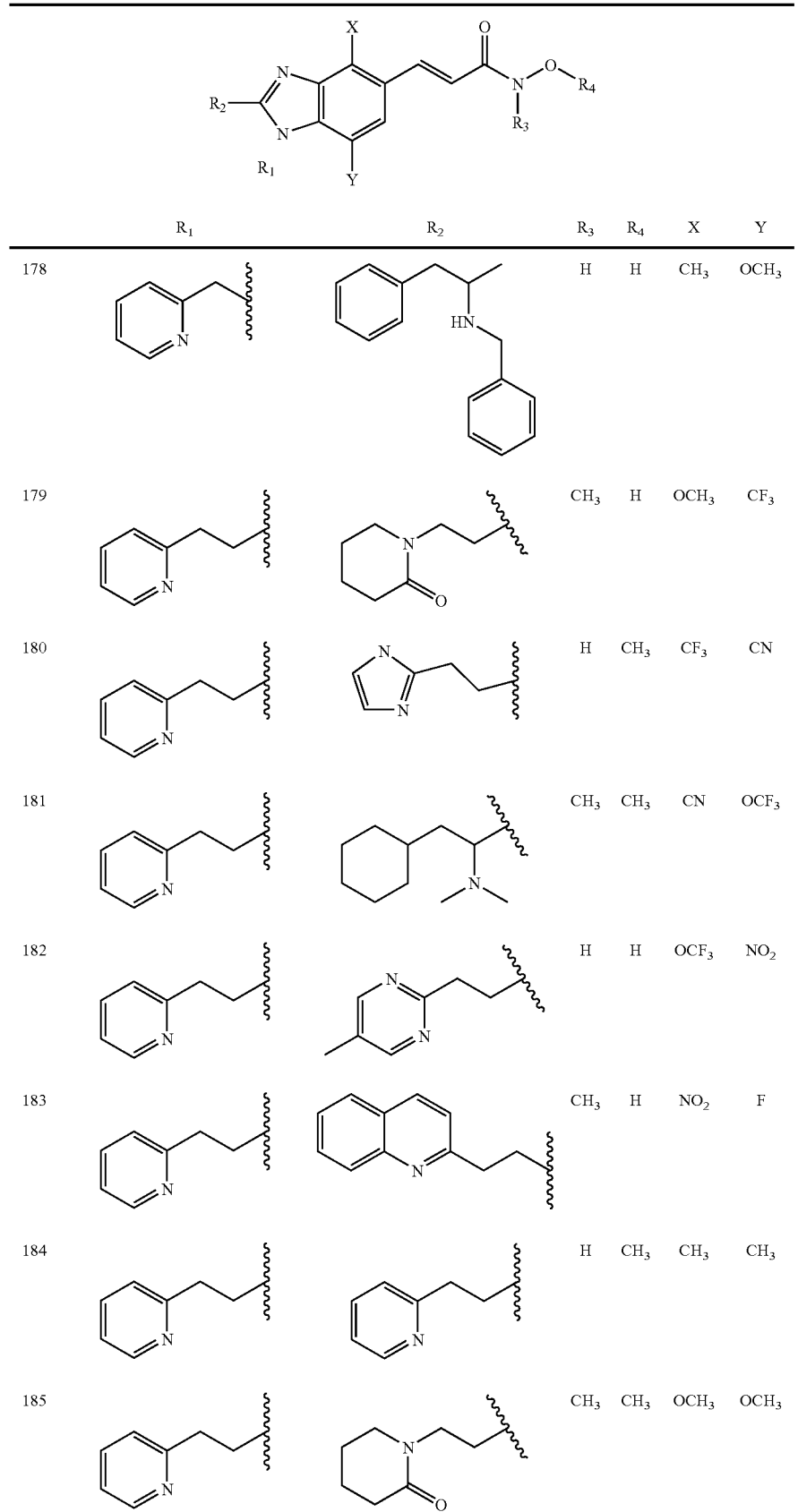

| | R₁ | R₂ | R₃ | R₄ | X | Y |
|---|---|---|---|---|---|---|
| 178 | 2-pyridyl-CH₂- | PhCH₂CH(CH₃)NH-CH₂Ph | H | H | CH₃ | OCH₃ |
| 179 | 2-pyridyl-CH₂CH₂- | piperidinone-N-CH₂CH₂- | CH₃ | H | OCH₃ | CF₃ |
| 180 | 2-pyridyl-CH₂CH₂- | imidazol-2-yl-CH₂CH₂- | H | CH₃ | CF₃ | CN |
| 181 | 2-pyridyl-CH₂CH₂- | cyclohexyl-CH₂CH(N(CH₃)₂)- | CH₃ | CH₃ | CN | OCF₃ |
| 182 | 2-pyridyl-CH₂CH₂- | 5-methylpyrimidin-2-yl-CH₂CH₂- | H | H | OCF₃ | NO₂ |
| 183 | 2-pyridyl-CH₂CH₂- | quinolin-2-yl-CH₂CH₂- | CH₃ | H | NO₂ | F |
| 184 | 2-pyridyl-CH₂CH₂- | 2-pyridyl-CH₂CH₂- | H | CH₃ | CH₃ | CH₃ |
| 185 | 2-pyridyl-CH₂CH₂- | piperidinone-N-CH₂CH₂- | CH₃ | CH₃ | OCH₃ | OCH₃ |

TABLE 2(B)-continued

| | R₁ | R₂ | R₃ | R₄ | X | Y |
|---|---|---|---|---|---|---|
| 186 | 2-pyridyl-ethyl | 2-furyl-ethyl | H | H | F | H |
| 187 | morpholinyl-propyl | quinolin-2-yl-ethyl | CH₃ | H | CH₃ | F |
| 188 | morpholinyl-propyl | pyrrolidin-1-yl-ethyl | H | CH₃ | OCH₃ | Cl |
| 189 | morpholinyl-propyl | 1-cyclohexyl-2-(dimethylamino) | CH₃ | CH₃ | CH₃ | Br |
| 190 | morpholinyl-propyl | 2-thienyl-ethyl | H | H | OCH₃ | CH₃ |
| 191 | morpholinyl-propyl | quinolin-2-yl-ethyl | CH₃ | H | CH₃ | OCH₃ |
| 192 | morpholinyl-propyl | 3-(diethylamino)propyl | H | CH₃ | CH₃ | CF₃ |
| 193 | morpholinyl-propyl | cyclohexyl-CH₂-A- (A = C, N, O, S) | CH₃ | CH₃ | OCH₃ | CN |
| 194 | morpholinyl-propyl | benzyl-A- (A = C, N, O, S) | H | H | F | OCF₃ |

TABLE 2(B)-continued
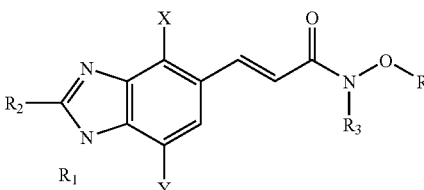
| | R₁ | R₂ | R₃ | R₄ | X | Y |
|---|---|---|---|---|---|---|
| 195 | 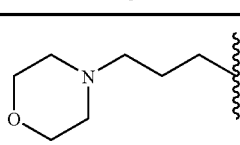 | 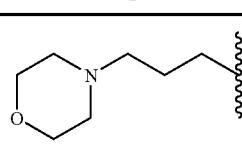 | CH₃ | H | H | NO₂ |
| 196 | 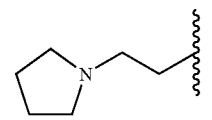 | 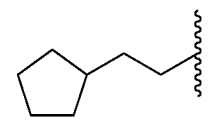 | H | CH₃ | F | CH₃ |
| 197 | 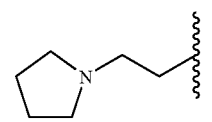 | 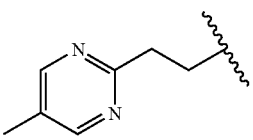 | CH₃ | CH₃ | Cl | OCH₃ |
| 198 | 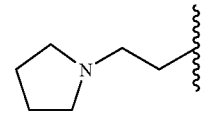 | 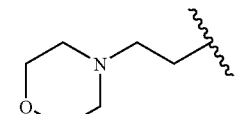 | H | H | Br | F |
| 199 | 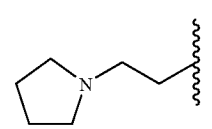 | 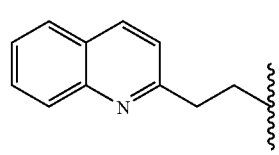 | CH₃ | H | CH₃ | CH₃ |
| 200 | 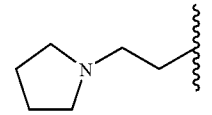 | 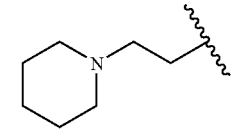 | H | CH₃ | OCH₃ | OCH₃ |
| 201 | 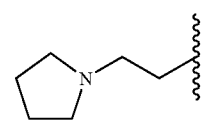 | 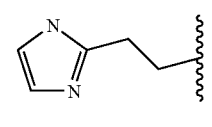 | CH₃ | CH₃ | CF₃ | CH₃ |
| 202 | 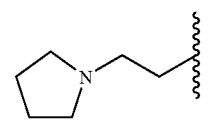 | 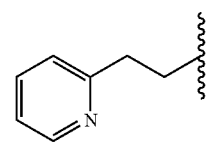 | H | H | CN | F |
| 203 | 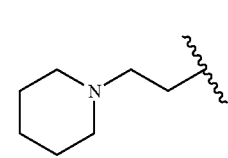 | 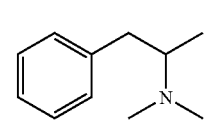 | CH₃ | H | OCF₃ | CH₃ |

TABLE 2(B)-continued

| | R₁ | R₂ | R₃ | R₄ | X | Y |
|---|---|---|---|---|---|---|
| 204 | piperidinyl-propyl | 2-thienyl-ethyl | H | CH₃ | NO₂ | OCH₃ |
| 205 | piperidinyl-propyl | 2-oxo-piperidinyl-propyl | CH₃ | CH₃ | CH₃ | CH₃ |
| 206 | piperidinyl-propyl | 2-furyl-ethyl | H | H | OCH₃ | H |
| 207 | piperidinyl-propyl | cyclohexyl-CH₂-A- (A = C, N, O, S) | CH₃ | H | CH₃ | F |
| 208 | piperidinyl-propyl | benzyl-A- (A = C, N, O, S) | H | CH₃ | OCH₃ | Cl |
| 209 | piperidinyl-propyl | morpholinyl-propyl | CH₃ | CH₃ | F | Br |
| 210 | 2-thienyl-ethyl | N-benzyl-α-methyl-phenethylamino | H | H | CH₃ | CH₃ |
| 211 | 2-thienyl-ethyl | 5-methyl-pyrimidin-2-yl-ethyl | CH₃ | H | H | OCH₃ |

TABLE 2(B)-continued
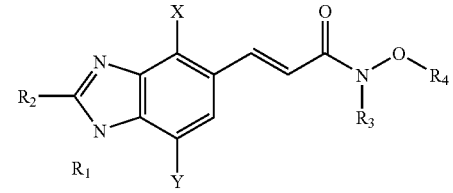
| | R₁ | R₂ | R₃ | R₄ | X | Y |
|---|---|---|---|---|---|---|
| 212 | 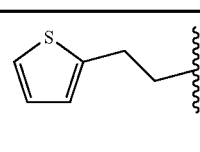 | 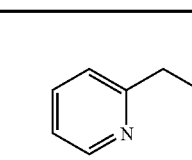 | H | CH₃ | F | CF₃ |
| 213 | 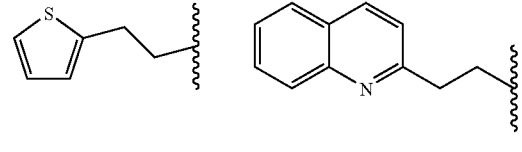 | 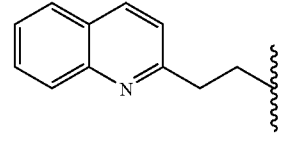 | CH₃ | CH₃ | Cl | CN |
| 214 |  | 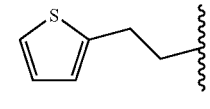 | H | H | Br | OCF₃ |
| 215 | 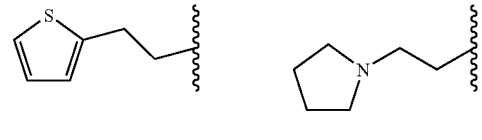 | 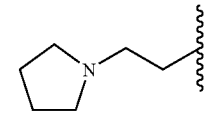 | CH₃ | H | CH₃ | NO₂ |
| 216 |  | 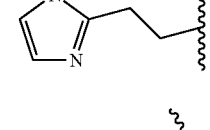 | H | H | OCH₃ | CH₃ |
| 217 | 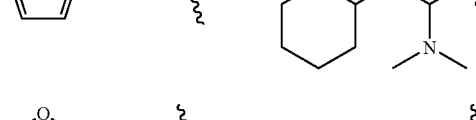 | 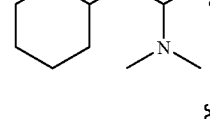 | CH₃ | H | CF₃ | F |
| 218 |  | 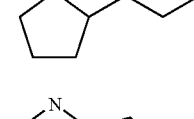 | H | CH₃ | CN | CH₃ |
| 219 |  | 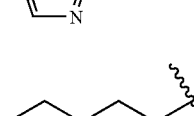 | CH₃ | CH₃ | OCF₃ | OCH₃ |
| 220 |  | 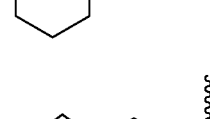 | H | H | NO₂ | CH₃ |
| 221 |  | 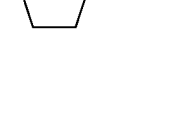 | CH₃ | H | CH₃ | OCH₃ |

TABLE 2(B)-continued
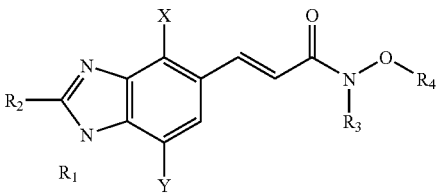
| | R₁ | R₂ | R₃ | R₄ | X | Y |
|---|---|---|---|---|---|---|
| 222 | 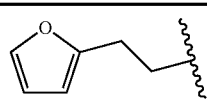 | 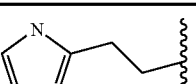 | H | CH₃ | H | H |
| 223 | 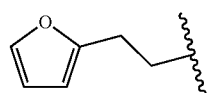 | 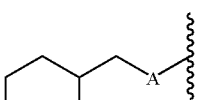<br>A = C, N, O, S | CH₃ | CH₃ | F | F |
| 224 | 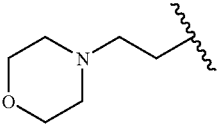 | 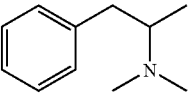 | H | H | Cl | Cl |
| 225 | 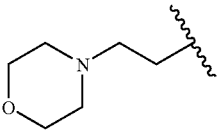 | 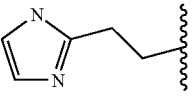 | CH₃ | H | Br | Br |
| 226 | 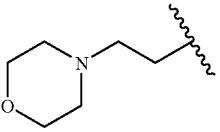 | 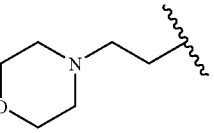 | H | CH₃ | CH₃ | CH₃ |
| 227 | 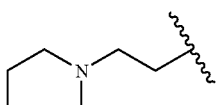 | 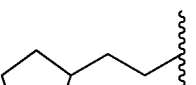 | CH₃ | CH₃ | OCH₃ | OCH₃ |
| 228 | 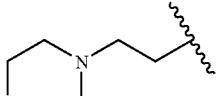 | 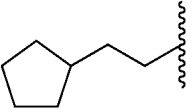 | H | H | CF₃ | CF₃ |
| 229 | 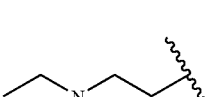 | 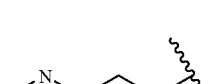 | CH₃ | H | CN | CN |
| 230 | 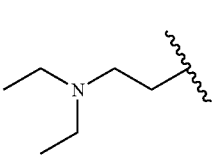 | 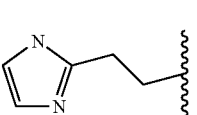 | H | CH₃ | OCF₃ | OCF₃ |

TABLE 2(B)-continued
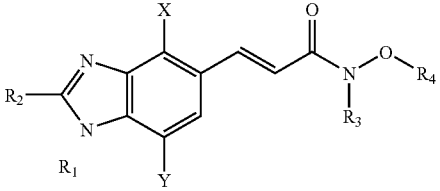
| | R₁ | R₂ | R₃ | R₄ | X | Y |
|---|---|---|---|---|---|---|
| 231 | 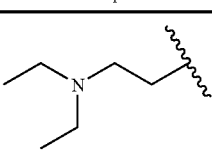 | 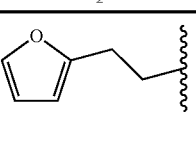 | CH₃ | CH₃ | NO₂ | NO₂ |
| 232 | 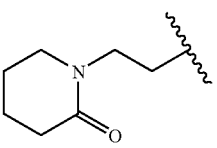 | 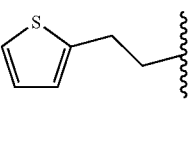 | H | H | CH₃ | CH₃ |
| 233 | 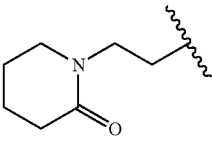 | 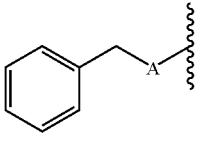 A = C, N, O, S | CH₃ | H | OCH₃ | OCH₃ |
| 234 | 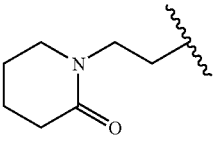 | 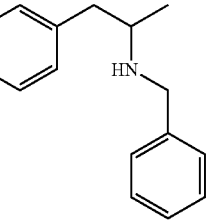 | H | CH₃ | F | F |
| 235 | 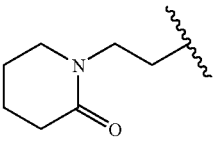 | 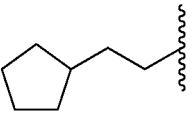 | CH₃ | CH₃ | CH₃ | CH₃ |
| 236 | 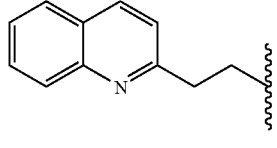 | 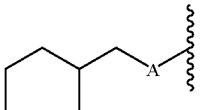 A = C, N, O, S | H | H | OCH₃ | OCH₃ |
| 237 | 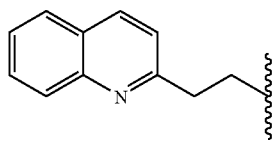 | 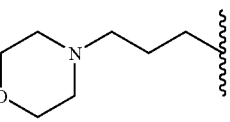 | CH₃ | H | CH₃ | F |
| 238 | 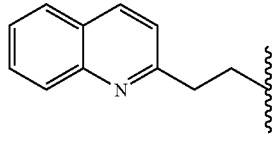 | 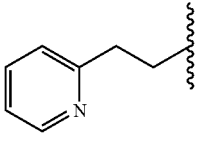 | H | CH₃ | OCH₃ | CH₃ |

TABLE 2(B)-continued

| | $R_1$ | $R_2$ | $R_3$ | $R_4$ | X | Y |
|---|---|---|---|---|---|---|
| 239 | quinolin-2-ylethyl | cyclopentylethyl | $CH_3$ | $CH_3$ | F | $OCH_3$ |

Biological Testing and Enzyme Assays

Recombinant GST-HDAC1 Protein Expression and Purification

Human cDNA library was prepared using cultured SW620 cells. Amplification of human HDAC1 and HDAC8 coding region from this cDNA library was cloned separately into the baculovirus expression pDEST20 vector and pFASTBAC vector respectively (GATEWAY Cloning Technology, Invitrogen Pte Ltd). The pDEST20-HDAC1 and pFASTBAC-HTGST-HDAC 8 constructs were confirmed by DNA sequencing. Recombinant baculovirus was prepared using the Bac-To-Bac method following the manufacturer's instruction (Invitrogen Pte Ltd). Baculovirus titer was determined by plaque assay to be about $10^8$ PFU/ml.

Expression of GST-HDAC1 or HTGST-HDAC8 was done by infecting SF9 cells (Invitrogen Pte Ltd) with pDEST20-HDAC1 or pFASTBAC-GST-HDAC8 baculovirus at MOI=1 for 48 h. Soluble cell lysate was incubated with pre-equilibrated Glutathione Sepharose 4B beads (Amersham) at 4° C. for 2 h. The beads were washed with PBS buffer for 3 times. The GST-HDAC1 protein or GST-HDAC8 protein was eluted by elution buffer containing 50 mM Tris, pH8.0, 150 mM NaCl, 1% Triton X-100 and 10 mM or 20 mM reduced Glutathione. The purified GST-HDAC1 protein or purified GST-HDAC8 protein was dialyzed with HDAC storage buffer containing 10 mM Tris, pH7.5, 100 mM NaCl and 3 mM $MgCl_2$. 20% Glycerol was added to purified GST-HDAC1 protein or purified GST-HDAC8 before storage at −80° C.

In Vitro HDAC Assay for Determination of IC50 Values

The assay has been carried out in 96 well format and the BIOMOL fluorescent-based HDAC activity assay has been applied. The reaction composed of assay buffer, containing 25 mM Tris pH 7.5, 137 mM NaCl, 2.7 mM KCl, 1 mM $MgCl_2$, 1 mg/ml BSA, tested compounds, 500 nM HDAC8 enzyme or 600 nM HDAC1 enzyme, 200 µM Flur de lys p53 peptide substrate for HDAC8 enzyme or 500 µM Flur de lys generic substrate for HDAC1 enzyme and subsequently was incubated at room temperature for 2 h. Flur de lys Developer was added and the reaction was incubated for 10 min. Briefly, deacetylation of the substrate sensitizes it to the developer, which then generates a fluorophore (symbol). The fluorophore is excited with 360 nm light and the emitted light (460 nm) is detected on a fluorometric plate reader (Tecan Ultra Microplate detection system, Tecan Group Ltd.).

The analytical software, Prism 3.0 has been used to generate $IC_{50}$ from a series of data. The HDAC enzyme inhibition results of representative compounds are shown in Table 3.

TABLE 3

| Compound | HDAC1 Enzyme Activity $IC_{50}$ (µM) | HDAC8 Enzyme Activity $IC_{50}$ (µM) |
|---|---|---|
| 1 | 0.051 | 0.119 |
| 2 | 0.026 | 0.355 |
| 3 | 1.37 | 1.71 |
| 4 | 1.34 | 0.790 |
| 5 | 4.32 | 0.401 |
| 6 | 1.38 | 0.262 |
| 7 | 1.52 | 0.336 |
| 8 | 0.286 | 0.454 |
| 9 | 1.34 | 0.344 |
| 10 | 2.66 | 0.883 |
| 11 | 0.846 | 0.161 |
| 12 | 0.131 | 0.202 |
| 13 | 0.385 | 0.141 |
| 14 | 0.171 | 0.251 |
| 15 | 0.206 | 0.313 |
| 16 | 0.194 | 0.366 |
| 17 | 0.024 | 0.353 |
| 18 | 0.438 | 0.290 |
| 19 | 0.165 | 0.145 |
| 20 | 1.91 | 0.537 |
| 21 | 0.064 | 0.238 |
| 22 | 1.326 | 0.234 |
| 23 | 0.529 | 0.402 |
| 24 | 3.24 | 0.203 |
| 25 | 1.32 | 0.601 |
| 26 | 0.876 | 1.005 |
| 27 | 0.092 | 0.329 |
| 28 | 0.206 | 0.300 |
| 29 | 49.06 | 33.96 |
| 30 | 0.195 | 0.724 |
| 31 | 0.246 | 1.09 |
| 32 | 2.21 | 1.89 |
| 33 | 0.449 | 1.45 |
| 34 | 1.46 | 0.846 |
| 35 | 0.371 | 0.412 |
| 36 | 0.227 | |
| 37 | 0.897 | |
| 38 | 0.218 | 0.148 |
| 39 | 1.22 | 0.201 |
| 40 | 3.30 | 0.441 |
| 41 | 0.195 | 0.159 |
| 42 | 0.479 | 0.237 |
| 43 | 0.947 | 0.192 |
| 44 | 0.268 | 0.345 |
| 45 | 0.167 | |
| 46 | 1.67 | |

TABLE 3-continued

| Compound | HDAC1 Enzyme Activity IC$_{50}$ (μM) | HDAC8 Enzyme Activity IC$_{50}$ (μM) |
|---|---|---|
| 47 | 1.09 | |
| 48 | 0.356 | 0.291 |
| 49 | 1.40 | |
| 50 | 0.173 | |
| 51 | 0.896 | |
| 52 | 0.160 | |
| 53 | 1.85 | |
| 54 | 0.100 | |
| 55 | 0.137 | |
| 56 | 0.158 | |
| 57 | 0.153 | |
| 58 | 1.14 | |
| 59 | 0.382 | |
| 60 | 0.116 | |
| 61 | 0.196 | |
| 62 | 0.234 | |
| 63 | 0.162 | |
| 64 | 0.230 | |
| 65 | 0.062 | |
| 66 | 0.072 | 0.255 |
| 67 | 0.039 | 0.254 |
| 68 | 0.294 | |
| 69 | 0.146 | |
| 70 | 0.923 | |
| 71 | 0.167 | |
| 72 | 0.052 | |
| 73 | 0.560 | |
| 74 | 0.371 | |
| 75 | 0.290 | |
| 76 | 1.03 | |
| 77 | 0.570 | |
| 78 | >100 | |
| 79 | 1.26 | |
| 80 | 1.69 | |
| 81 | 1.60 | |
| 82 | 0.304 | |
| 83 | 0.071 | |
| 84 | 0.054 | |
| 85 | 0.131 | |
| 86 | 0.400 | |
| 87 | 0.517 | |
| 88 | 0.297 | |
| 89 | 0.116 | |
| 90 | 0.166 | |
| 91 | 0.030 | |
| 92 | 0.168 | |
| 93 | 0.065 | |
| 94 | 0.052 | |
| 95 | 0.061 | |
| 96 | 0.125 | |

Cell-Based Proliferation Assay for Determination of GI$_{50}$ Values

Human colon cancer cell lines (Colo205 and HCT116), human breast cancer cell lines (MDA-MB435 and MDA-MB231), and human lung cancer cell line (A549) were obtained from ATCC. Colo205 cells were cultivated in RPMI1640 containing 2 mM L-Glutamine, 5% FBS, 1.0 mM Na Pyruvate. A549 and MDA-MB231 were cultivated in RPMI 1640 containing 2 mM L-glutamine, 5% FBS. MDA-MB435 cells were cultivated in DMEM containing 2 L-Glutamine, 5% FBS. HCT116 cells were cultivated in IMEM containing 2 mM L-Glutamine, 5% FBS. A549 and Colo205 cells were seeded in 96-wells plate at 2000 and 5000 cells per well respectively. MDA-MB435, HCT116, MDA-MB231 cells were seeded in 96-wells plate at 6000 cells per well. The plates were incubated at 37° C., 5% CO$_2$, for 24 h. Cells were treated with compounds at various concentration for 96 h. Cell growth was then monitored using cyquant cell proliferation assay (Invitrogen Pte Ltd). Dose response curves were plotted to determine GI$_{50}$ values for the compounds using XL-fit.

The cell activity results of representative compounds are shown in Table 4. Table 5 summarized the antiproliferative activities of selected compounds including their different salts for additional cancer cell lines. These data indicate that compounds in this invention are highly active in inhibition of tumor cell growth.

TABLE 4

| Compound | GI50 (Colo 205, μM) | GI50 (MDA-MB435, μM) |
|---|---|---|
| 1 | 0.52 | 1.64 |
| 2 | 0.43 | 0.32 |
| 4 | 29.87 | 25.70 |
| 5 | >100 | |
| 6 | >100 | |
| 7 | >100 | |
| 8 | 41.36 | 58.42 |
| 9 | >100 | >100 |
| 11 | >100 | >100 |
| 12 | 0.38 | 1.07 |
| 13 | 12.32 | 14.05 |
| 14 | 3.07 | 5.99 |
| 15 | 1.99 | 4.07 |
| 16 | 0.94 | 0.98 |
| 17 | 0.06 | 0.56 |
| 18 | 4.69 | 6.16 |
| 19 | 4.10 | 3.97 |
| 20 | 30.86 | 37.22 |
| 21 | 25.91 | 30.26 |
| 22 | 13.47 | 13.35 |
| 23 | 3.65 | 3.72 |
| 24 | 30.70 | 35.02 |
| 25 | 8.10 | 6.82 |
| 26 | 8.79 | 6.67 |
| 27 | 2.23 | 3.44 |
| 28 | 2.53 | 5.15 |
| 30 | 11.44 | 19.85 |
| 31 | 1.87 | 4.06 |
| 33 | 1.54 | 3.38 |
| 35 | 1.89 | 6.76 |
| 36 | 2.29 | 2.17 |
| 37 | 7.82 | 7.90 |
| 38 | 1.47 | 1.53 |
| 39 | 11.68 | 12.05 |
| 40 | 25.62 | 30.97 |
| 41 | 1.65 | 1.91 |
| 42 | 14.41 | 15.75 |
| 43 | 9.18 | 8.62 |
| 44 | 2.82 | 3.65 |
| 45 | 2.41 | 1.90 |
| 48 | 1.45 | 1.78 |
| 50 | 4.29 | 5.19 |
| 52 | 2.04 | 3.58 |
| 54 | 4.47 | 5.92 |
| 55 | >100 | >100 |
| 56 | >100 | >100 |
| 57 | 1.11 | 1.39 |
| 59 | 2.72 | 3.69 |
| 60 | 2.47 | 3.60 |
| 61 | 2.69 | 3.05 |
| 62 | 11.65 | 19.80 |
| 63 | 2.00 | |
| 64 | 1.70 | |
| 65 | 36.89 | |
| 66 | 0.22 | |
| 67 | 0.08 | |
| 68 | 0.73 | |
| 69 | 7.16 | |
| 70 | 2.90 | |
| 71 | 7.09 | |
| 72 | 0.18 | |
| 73 | 6.67 | |
| 74 | 2.07 | |
| 75 | 2.88 | |

TABLE 4-continued

| Compound | GI50 (Colo 205, μM) | GI50 (MDA-MB435, μM) |
|---|---|---|
| 82 | 0.72 | |
| 83 | 0.25 | |
| 84 | 0.17 | |
| 85 | 1.65 | |
| 86 | 13.13 | |
| 87 | 47.71 | |
| 88 | 1.26 | |
| 89 | 0.12 | |

TABLE 5

| | Compound 2 | | Compound 17 | | | Compound 67 | |
|---|---|---|---|---|---|---|---|
| Activity | Free base | Salt of CF3COOH | Free base | Salt of HCl | Salt of Methane sulfonic acid | Salt of CF3COOH | Free base | Salt of CF3COOH |
| IC$_{50}$ (HDAC1, μM) | 0.043 | 0.049 | 0.029 | 0.044 | 0.051 | 0.024 | 0.037 | 0.039 |
| IC$_{50}$ (HDAC3, μM) | 0.064 | | 0.029 | | | | 0.056 | |
| IC$_{50}$ (HDAC8, μM) | 0.267 | | 0.353 | | | | 0.254 | |
| GI$_{50}$ (Colo205, μM) | 0.4 | 0.4 | 0.06 | 0.06 | 0.04 | 0.11 | 0.09 | 0.09 |
| GI$_{50}$ (HCT116, μM) | 0.4 | | 0.3 | | | | 0.06 | |
| GI$_{50}$ (MDA-MB435, μM) | 0.3 | | 0.6 | | | | 0.19 | |
| GI$_{50}$ (MDA-MB231, μM) | 0.5 | | 0.7 | | | | 0.06 | |
| GI$_{50}$ (A549, μM) | 0.3 | | 0.2 | | | | 0.08 | |

Histone H3 Acetylation Assay

A hallmark of histone deacetylase (HDAC) inhibition is the increase in the acetylation level of histones. Histone acetylation, including H3, H4 and H2A can be detected by immuno-blotting (western-blot). Colo205 cells, approximately 1.5× $10^6$ cells/10 cm dish, were seeded in the previously described medium, cultivated for 24 h and subsequently treated with HDAC inhibitory agents at 0.1, 1, 5 and 10 μM final concentration. After 24 h, cells were harvested and lysed according to the instruction from Sigma Mammalian Cell Lysis Kit. The protein concentration was quantified using BCA method (Sigma Pte Ltd). The protein lysate was separated using 4-12% bis-tris SDS-PAGE gel (Invitrogen Pte Ltd) and was transferred onto PVDF membrane (BioRad Pte Ltd). The membrane was probed separately using primary antibody specific for acetylated H3, acetylated H4 or acetylated H2A (Upstate Pte Ltd). The detection antibody, goat anti rabbit antibody conjugated with HRP was used according to the manufacturing instruction (Pierce Pte Ltd). After removing the detection antibody from the membrane, an enhanced chemiluminescent substrate for detection of HRP (Pierce Pte Ltd) was added onto the membrane. After removing the substrate, the membrane was exposed to an X-ray film (Kodak) for 1 sec-20 mins. The X-ray film was developed using the X-ray film processor. The density of each band observed on the developed film could be analysed using UVP Bioimaging software (UVP, Inc, Upland Calif.). The values were then normalized against the density of actin in the corresponding samples to obtain the expression of the protein.

The results of immuno-blotting assay using histone deacetylase H3, H4 and H2A antibodies are shown in Table 6.

TABLE 6

| | Histone acetylation activities | | |
|---|---|---|---|
| Compound | Histone-3 | Histone-4 | Histone-2A |
| 1 | Active | Active | Active |
| 2 | Active | Active | Active |
| 12 | Active | Active | |
| 17 | Active | Active | Active |
| 67 | Active | Active | Active |

These data demonstrate that compounds in this invention inhibit histone deacetylases, thereby resulting in accumulation of acetylated histones.

Histone H3 Acetylation Assay—ELISA Approach

An Enzyme Linked Immunosorbent Assay (ELISA) can be applied to detect and quantify the acetylated histone3 (ACH3) in the protein lysate obtained from cancer cell lines treated with the HDAC inhibitors.

The ELISA assay was developed to detect the level of AcH3 from the Colo205 colon cancer cell line treated with 10 μM HDAC inhibitory compounds. The protein lysates from untreated and treated Colo205 were obtained as previously described. The concentration of protein from lysed cells was determined using the BCA method (Sigma-Aldrich Pte Ltd).

Different combinations of antibodies (see Table 7) that could be used as primary antibody (capture antibody) or secondary antibody were investigated in order to determine suitable antibodies as well as to optimize antibody concentrations and assay conditions. It was found that the combination of mouse monoclonal antibody against H3 and rabbit polyclonal antibody against ACH3 (Lys9/14) produced the best binding to the antigens, either peptides or protein lysate from Colo205 colon cancer cell line treated with the HDAC inhibitors. No background was observed. The detection antibody used in this ELISA was donkey anti rabbit conjugated with peroxidase.

To determine $EC_{50}$ where acetylated histone 3 was induced by 50%, Colo205 cells was cultivated in 96 well plate at $1.5 \times 10^5$ cells/well for 24 h. Colo205 cells were subsequently treated with HDAC inhibitors at different doses (in duplicates, 9 doses treatment, 4-fold dilutions from 100 μM). After treatment for 24 h, cells were lysed and the protein concentration was determined.

The ELISA plate (immulon 2HB plate, Biolaboratories Pte Ltd) was coated with 4 μg/ml of mouse monoclonal antibody against H3 at 4° C. overnight. After removed mouse monoclonal antibody against H3, the plate was washed with PBS buffer containing 0.05% Tween-20 and blocked with the superblock solution (Pierce Pte Ltd) at 37° C., 1 h. The superblock solution was removed and the plate was washed with the PBS buffer containing 0.05% Tween. The ACH3 peptide, H3 peptide and the protein lysates from treated Colo205 with the HDAC inhibitors were applied. The capture reaction between the primary antibody and the antigen, which is histone 3 in the samples, was carried out at 37° C. for 1 h. After removing the samples, the plate was washed with PBS buffer containing 0.05% Tween. The secondary antibody, 0.5 μg/ml of rabbit polyclonal antibody against ACH3 (Lys9/14), was applied to detect the acetylation H3 in the samples at 37° C. for 1 h. After removing the secondary antibodies, the plate was washed with PBS buffer containing 0.05% Tween. The detection antibody was applied to detect the secondary antibody that captured ACH3 in the samples at 37° C. for 30 min. The substrate, 1-step Turbo TMB (Pierce Pte Ltd) was applied for 30 min until the color was developed. The reaction was stopped using 1M $H_2SO_4$. The absorbance was measured at OD450 nm using Spectromax reader (Molecular Devices Corporation, Sunnyvale, Calif.).

The standard curve was drawn and the concentration of ACH3 [(Lys9/14), μg/ml] in a sample was determined using the Softmax software in Spectromax. The amount of ACH3 in a sample was calculated based on the following formula;

$$pg \text{ of } AcH3\,(Lys9/14)/\mu g \text{ of total protein total} = \frac{(\mu g \text{ of } AcH3(Lys9/14) \text{ in the assay}) * 10^6}{\mu g \text{ of protein in the assay}}$$

Dose response curves were plotted to determine $EC_{50}$ values for the compounds using XL-fit (ID Business Solution, Emeryville, Calif.). [Table 8]

TABLE 7

Antibodies used in the cross-species reactivity test and the combination antibodies studies

| Antibodies used as either primary or secondary antibody | Detection antibody conjugated with HRP (horse radish peroxidase) |
|---|---|
| Rabbit polyclonal antibody against AcH3 (Lys9/14; Upstate Pte Ltd), | Donkey anti rabbit (Pierce Pte Ltd) |
| Rabbit polyclonal antibody against AcH3 (Lys14; Upstate Pte Ltd), | Goat anti rabbit (Pierce Pte Ltd) |
| Rabbit polyclonal antibody against AcH3 (Lys9, Upstate Pte Ltd), | Goat anti mouse (Pierce Pte Ltd) |
| Goat polyclonal antibody against AcH3 (Lys9/14, Santa Cruz Pte Ltd), | Rabbit anti goat (Pierce Pte Ltd) |
| Goat polyclonal antibody against H3 (N-20, Santa Cruz Pte Ltd) | Mouse anti goat (Pierce Pte Ltd) |
| Mouse monoclonal antibody against H3 (Upstate Pte Ltd) | |

Data for selected compounds are presented in Table 8, as the concentration effective for induction of acetylation of histone 3 ([AcH3(lys9/14)]) signal by 50% ($EC_{50}$).

TABLE 8

| Compound | Structure | $EC_{50}$ (μM) |
|---|---|---|
| 2 | 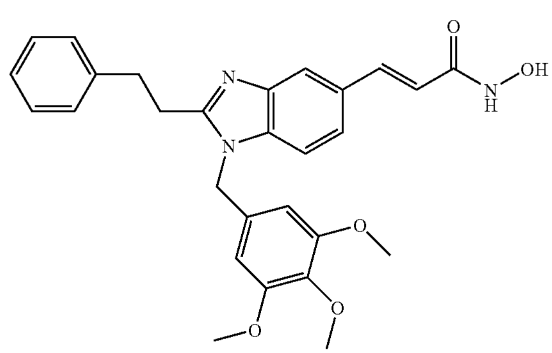 | 1.7 |

TABLE 8-continued

| Compound | Structure | EC$_{50}$ (μM) |
|---|---|---|
| 17 | 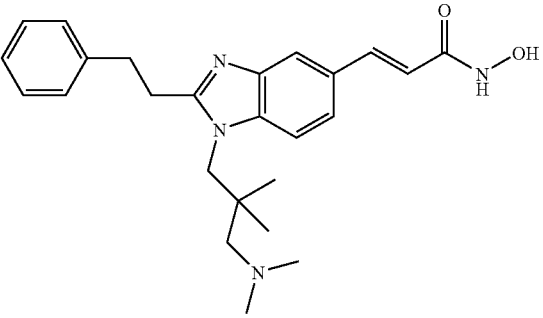 | 1.1 |
| 67 | 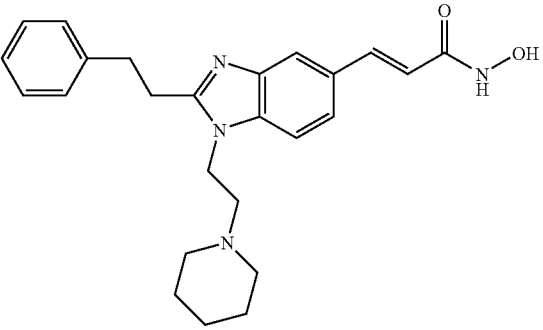 | 0.5 |

In vivo Antineoplastic (or Anti-Tumor) Effect of HDAC Inhibiting Agents:

In data not shown, selected compounds were tested for maximal tolerated dose in normal mice and were found to be well tolerated by the mice with no obvious signs of toxicity or side effects in the dose range applied (which can be >200 mg/kg/day).

The efficacy of the compounds of the invention can then be determined using in vivo animal xenograft studies.

In these studies Female atymic nude mice (Harlan), 12-14 weeks of age would be implanted subcutaneously in the flank with 5×10$^6$ cells of HCT116 or with 1×10$^6$ cells of Colo205 human colon carcinoma suspended in 50% Matrigel. When the tumor reaches the size 100 mm$^3$, the xenograft nude mice would be paired-match into various treatment groups. The selected HDAC inhibitors would be dissolved in appropriate vehicles, such as 10% DMA/10% Cremophore/80% water and administered to xenograft nude mice intraperitoneally by daily for 14 days. The dosing volume will be 0.2-ml/20 g mouse. Paclitaxol, used as positive control, will be prepared for intravenous administration in 10% Ethanol/10% Cremophore/80% water. The dosing volume for Paclitaxol will be 0.015-ml/g mouse. Tumor volume will be calculated every second day of post injection using the formula: Tumor volume (mm$^3$)=(w×l)/2, where w=width and l=length in mm of an HCT116 or Colo205 carcinoma. Compounds in this invention that are tested would show significant reduction in tumor volume relative to controls treated with vehicle only. The activity of histone deacetylase when measured shall be reduced and results in accumulation of acetylated histone relative to vehicle treated control group.

The details of specific embodiments described in this invention are not to be construed as limitations. Various equivalents and modifications may be made without departing from the essence and scope of this invention, and it is understood that such equivalent embodiments are part of this invention.

What is claimed is:

1. A compound of the formula:

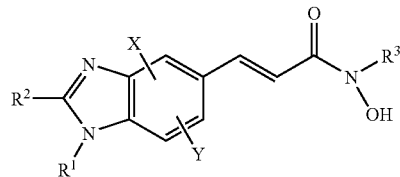

wherein

R$^1$ is selected from the group consisting of: H and unsubstituted or substituted C$_1$-C$_{10}$ alkyl, alkenyl, alkynyl, haloalkyl, heteroalkyl, cycloalkyl, heterocycloalkyl, aryl, heteroaryl, cycloalkylalkyl, C$_4$-C$_9$ heterocycloalkylalkyl, arylalkyl, and heteroarylalkyl, each of which may be unsubstituted or substituted with one or more substituents independently selected from the group consisting of: halogen, =O, =S, —CN, —NO$_2$, alkyl, alkenyl, alkynyl, haloalkyl, heteroalkyl, cycloalkyl, heterocycloalkyl, aryl, heteroaryl, hydroxy, hydroxyalkyl, alkoxy, alkoxyalkyl, alkylamino, acylamino, aminoalkyl, phenoxy, benzyloxy, alkylsulfonyl, arylsulfonyl, aminosulfonyl, —COOH, —C(O)OR$^5$, —SH, and acyl;

R$^2$ is selected from the group consisting of: H, halogen, and unsubstituted or substituted C$_1$-C$_{10}$ alkyl, alkenyl, alkynyl, haloalkyl, heteroalkyl, cycloalkyl, heterocycloalkyl, aryl, heteroaryl, cycloalkylalkyl, C$_4$-C$_9$ heterocycloalkylalkyl, arylalkyl, and heteroarylalkyl, each of which may be unsubstituted or substituted with one or more substituents independently selected from the group consisting of: halogen, =O, =S, —CN, —NO$_2$, alkyl, alkenyl, alkynyl, haloalkyl, heteroalkyl, cycloalkyl, heterocycloalkyl, aryl, heteroaryl, hydroxy, hydroxyalkyl, alkoxy, alkoxyalkyl, phenoxy, benzyloxy, alkylamino, acylamino, aminoalkyl, alkylsulfonyl, arylsulfonyl, aminosulfonyl, —COOH, —C(O)OR$^5$, —SH, and acyl;

R$^3$ is selected from the group consisting of H, C$_1$-C$_6$ alkyl, and acyl;

X and Y are the same or different and are independently selected from the group consisting of: H, halogen, —CN, —NO$_2$, —CF$_3$, C$_1$-C$_4$ alkyl, —COR$^5$, —SR$^6$, —OR$^6$, and —NR$^7$R$^8$;

R$^5$ is C$_1$-C$_4$ alkyl;

R$^6$ is C$_1$-C$_4$ alkyl;

R$^7$ and R$^8$ are each independently selected from the group consisting of: H, C$_1$-C$_4$ alkyl, C$_4$-C$_9$ cycloalkyl, C$_4$-C$_9$ heterocycloalkyl, aryl, heteroaryl, arylalkyl and heteroarylalkyl;

or a pharmaceutically acceptable salt thereof.

2. A compound according to claim 1 wherein R$^3$=H.

3. A compound according to claim 1 wherein X and Y=H.

4. A compound according to claim 1 wherein R$_1$ is selected from the group consisting of: H and unsubstituted or substituted hydroxyalkyl, C$_1$-C$_{10}$ alkyl, heteroalkyl, arylalkyl, heteroarylalkyl, and heterocycloalkyl, each of which may be unsubstituted or substituted as defined in claim 1.

5. The compound according to claim 1 wherein R$_1$ is selected from the group consisting of: H, methyl; (pyridin-3-yl)methyl; 2-hydroxy-ethyl; 2,3-di-hydroxy-propyl; and 3-hydroxy-propyl.

6. A compound according to claim 1 wherein R$^2$ is selected from the group consisting of H, and unsubstituted or substituted C$_1$-C$_{10}$ alkyl, arylalkyl, aryl, heteroaryl, heteroalkyl, and cycloalkyl, each of which may be unsubstituted or substituted as defined in claim 1.

7. A compound according to claim 1 wherein R$^2$ is selected from the group consisting of 2-phenyl-propyl, 2-phenyl-ethyl, 4-methoxy-phenyl, 4-benzyloxy-3-methoxy-phenyl, pyridin-2-yl, and pyridin-4-yl.

8. The compound of claim 1 wherein the compound is selected from compounds, and their pharmaceutically acceptable salts, selected from the group consisting of

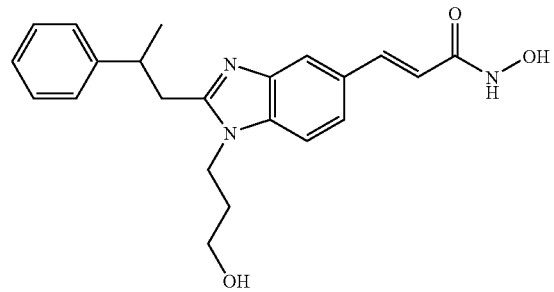

N-Hydroxy-3-[1-(3-hydroxy-propyl)-2-(2-phenyl-propyl)-1H-benzimidazol-5-yl]-acrylamide -continued

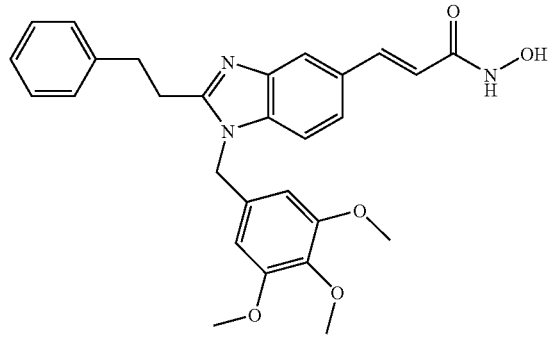

N-Hydroxy-3-[1-(3,4,5-trimethoxybenzyl)-2-(2-phenyl-ethyl)-1H-benzimidazol-5-yl]-acrylamide

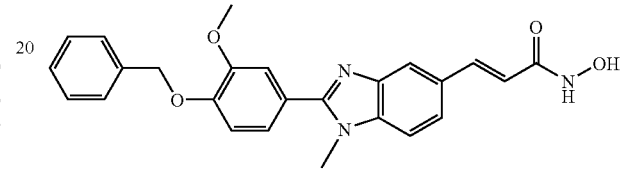

N-Hydroxy-3-[2-(4-benzyloxy-3-methoxy-phenyl)-1-methyl-1H-benzimidazole-5-y]-acrylamide

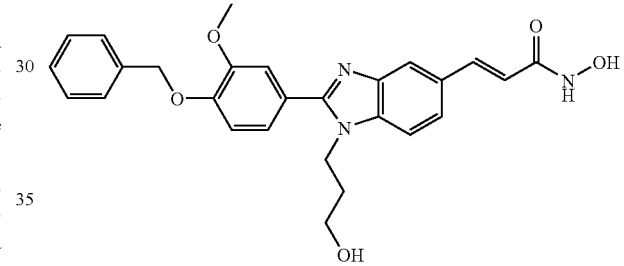

N-Hydroxy-3-[2-(4-benzyloxy-3-methoxy-phenyl)-1-(3-hydroxy-propyl)-1H-benzimidazole-5-yl]-acrylamide

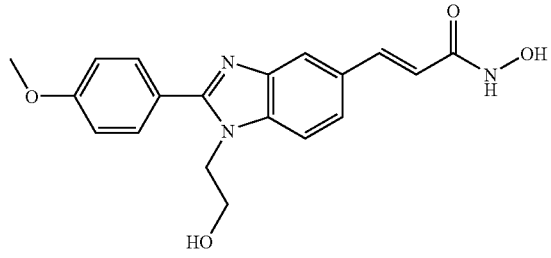

N-Hydroxy-3-[1-(2-hydroxy-ethyl)-2-(4-methoxy-phenyl)-1H-benzimidazole-5-yl]-acrylamide

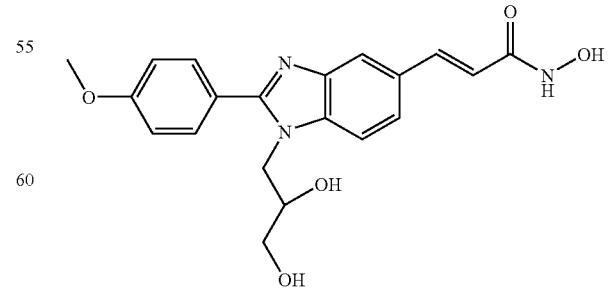

N-Hydroxy-3-[1-(2,3-hydroxy-propyl)-2-(4-methoxy-phenyl)-1H-benzimidazole-5-yl]-acrylamide

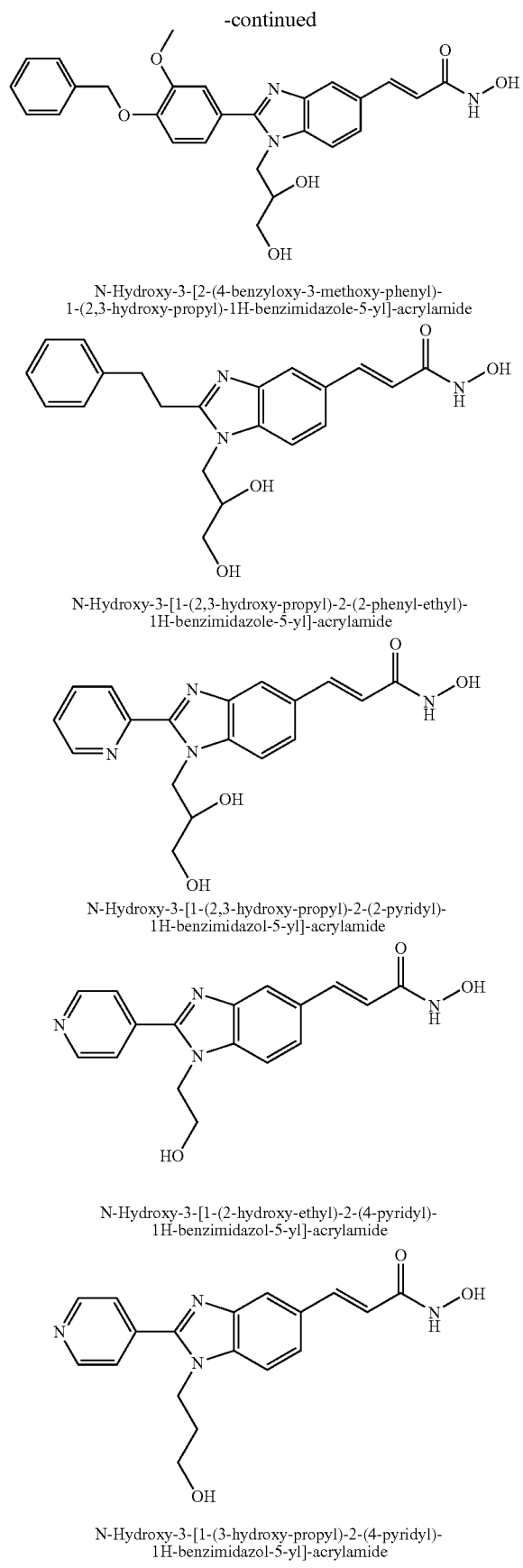

N-Hydroxy-3-[2-(4-benzyloxy-3-methoxy-phenyl)-1-(2,3-hydroxy-propyl)-1H-benzimidazole-5-yl]-acrylamide N-Hydroxy-3-[1-(2,3-hydroxy-propyl)-2-(2-phenyl-ethyl)-1H-benzimidazole-5-yl]-acrylamide N-Hydroxy-3-[1-(2,3-hydroxy-propyl)-2-(2-pyridyl)-1H-benzimidazol-5-yl]-acrylamide N-Hydroxy-3-[1-(2-hydroxy-ethyl)-2-(4-pyridyl)-1H-benzimidazol-5-yl]-acrylamide N-Hydroxy-3-[1-(3-hydroxy-propyl)-2-(4-pyridyl)-1H-benzimidazol-5-yl]-acrylamide

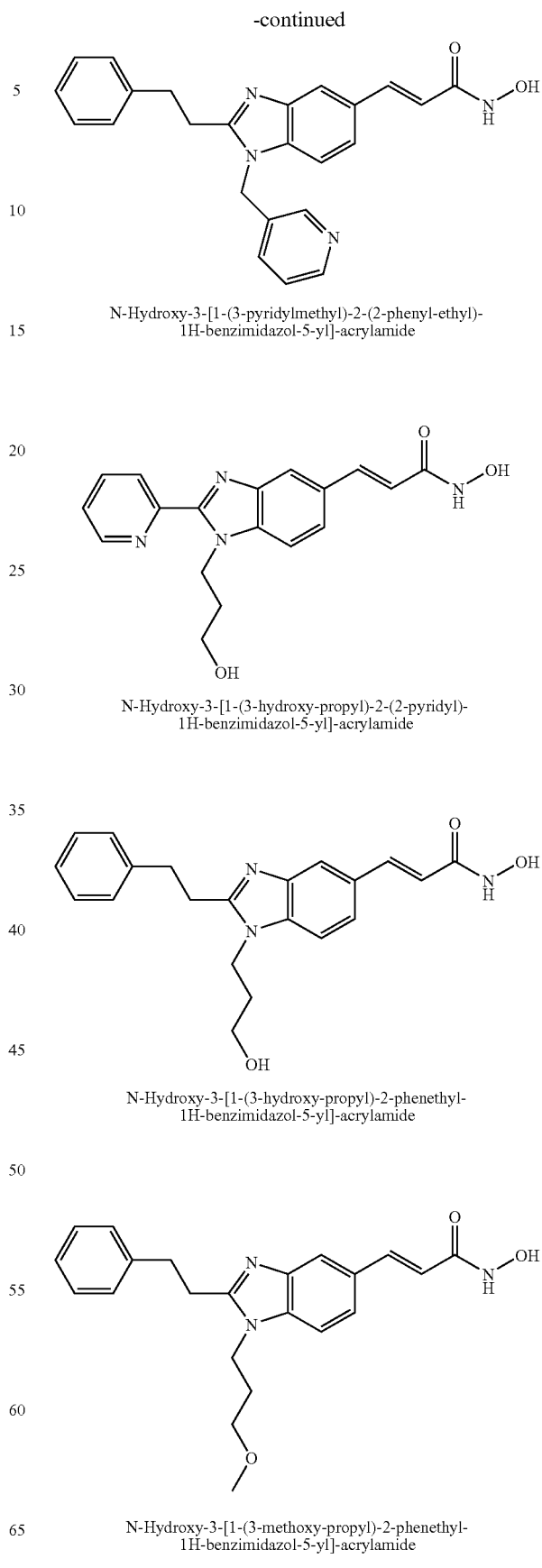

N-Hydroxy-3-[1-(3-pyridylmethyl)-2-(2-phenyl-ethyl)-1H-benzimidazol-5-yl]-acrylamide N-Hydroxy-3-[1-(3-hydroxy-propyl)-2-(2-pyridyl)-1H-benzimidazol-5-yl]-acrylamide N-Hydroxy-3-[1-(3-hydroxy-propyl)-2-phenethyl-1H-benzimidazol-5-yl]-acrylamide N-Hydroxy-3-[1-(3-methoxy-propyl)-2-phenethyl-1H-benzimidazol-5-yl]-acrylamide -continued

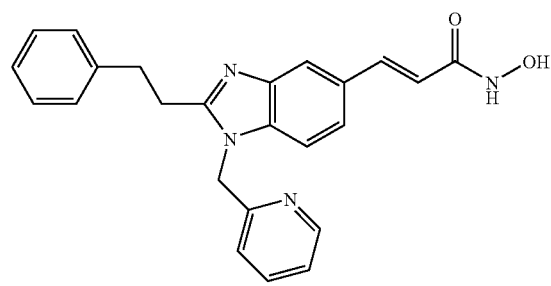

N-Hydroxy-3-(2-phenethyl-1-(pyridin-2-yl)methyl-
1H-benzimidazol-5-yl)-acrylamide

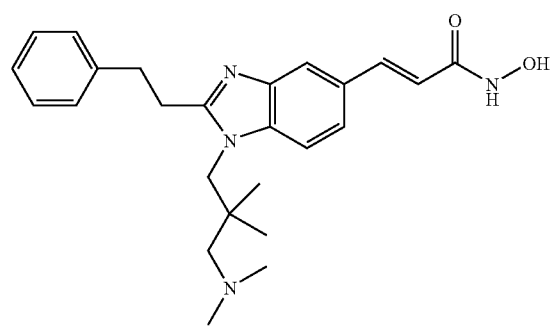

N-Hydroxy-3-[1-(3-Dimethylamino-2,2-dimethyl-
proppyl)-2-phenethyl-1H-benzimidazol-5-yl]-acrylamide

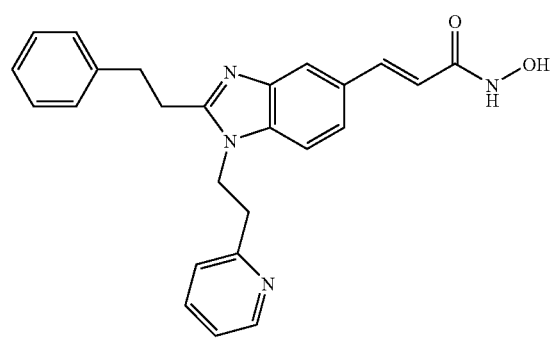

N-Hydroxy-3-[2-phenethyl-1-(2-pyridin-2-yl-ethyl)-
1H-benzimidazol-5-yl]-acrylamide

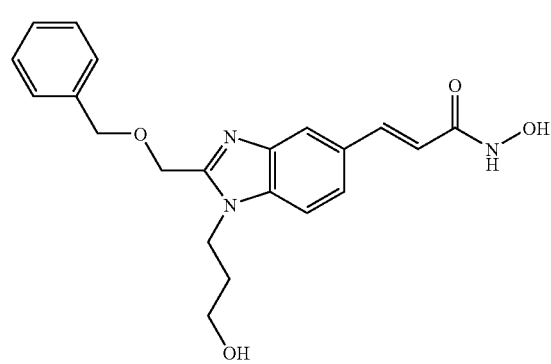

N-Hydroxy-3-[2-Benzyloxymethyl-1-(3-hydroxy-
propyl-1H-benzimidazl-5yl]-acrylamide -continued

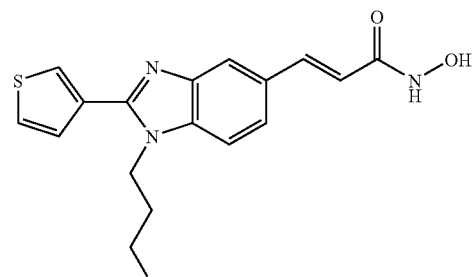

N-Hydroxy-3-[1-(3-hydroxy-propyl)-2-thiophen-3-
yl-1H-benzimidazol-5-yl]-acrylamide

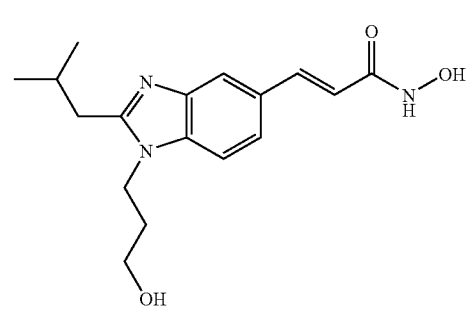

N-Hydroxy-3-[1-(3-hydroxy-propyl)-2-isobutyl-1H-
benzimidazol-5-yl]-acrylamide

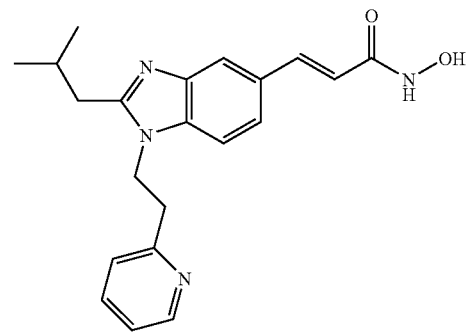

N-Hydroxy-3-[2-isobutyl-1-(2-pyridin-2-yl-ethyl)-
1H-benzimidazol-5-yl]-acrylamide

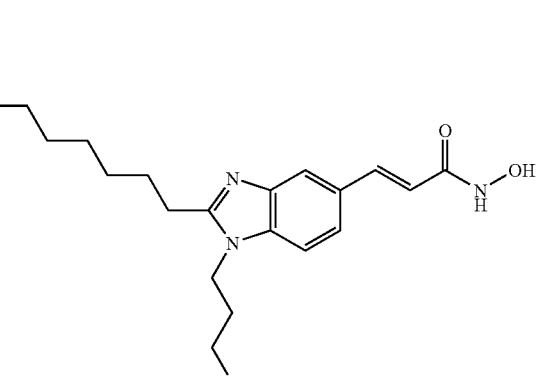

N-Hydroxy-3-[1-(3-hydroxy-propyl)-2-octyl-1H-
benzimidazol-5-yl]-acrylamide

-continued

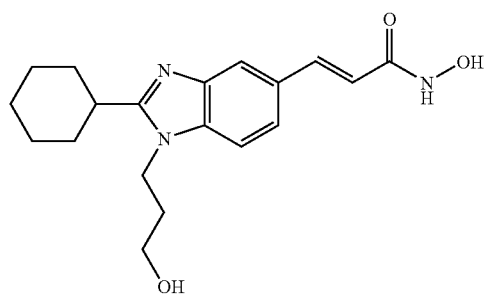
N-Hydroxy-[2-cyclohexyl-1-(3-hydroxy-propyl)-1H-benzimidazol-5-yl]-acrylamide

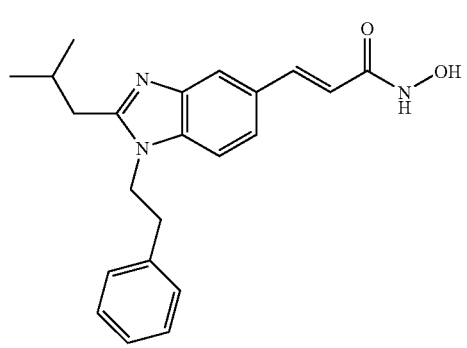
N-Hydroxy-3-(2-isobutyl-1-phenethyl-1H-benzimidazol-5-yl)-acrylamide

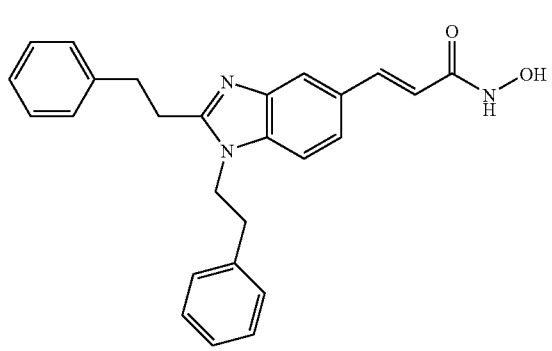
N-Hydroxy-3-(1,2-Diphenethyl-1H-benzimidazol-5-yl]-acrylamide

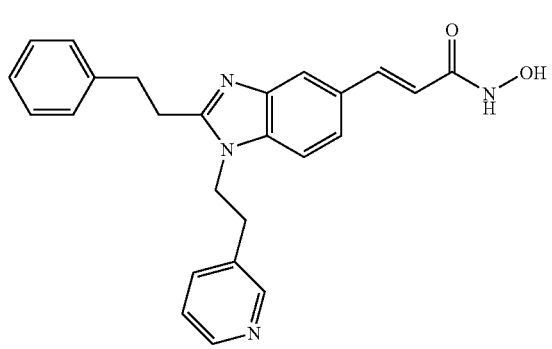
N-Hydroxy-3-(2-phenethyl-1-(2-pyridin-3-yl-ethyl)-1H-benzimidazol-5-yl]-acrylamide -continued

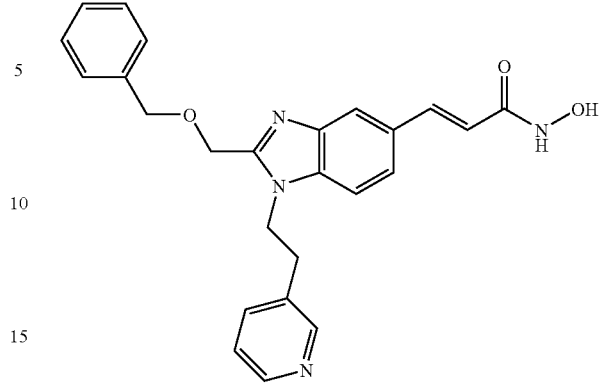
N-Hydroxy-3-[2-Benzyloxymethyl-1-(2-pyridin-3-ethyl)-1H-benzimidazol-5-yl]-acrylamide

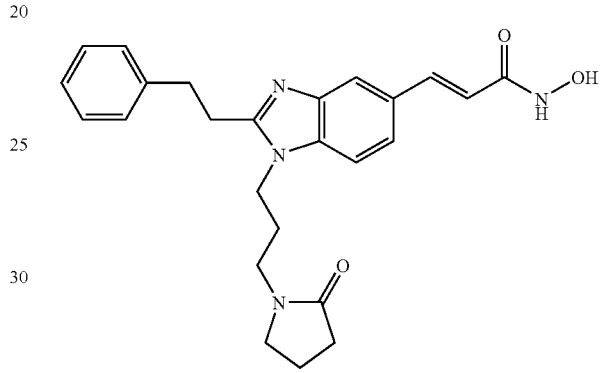
N-Hydroxy-3-{1-[3-(2-oxo-pyrrolidin-1-yl)-propyl]-2-phenethyl-1H-benzimidazol-5-yl}-acrylamide

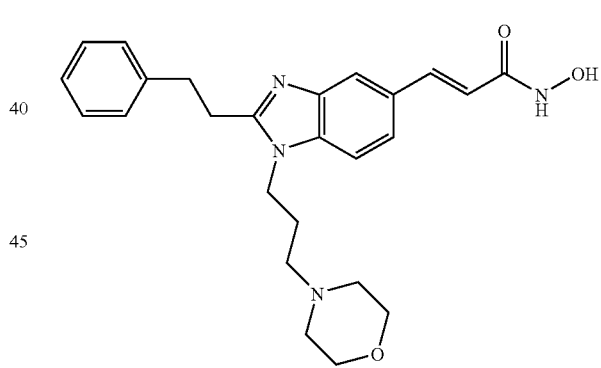
N-Hydroxy-3-[1-(3-morpholin-4-propyl]-2-phenethyl-1H-benzimidazol-5-yl}-acrylamide

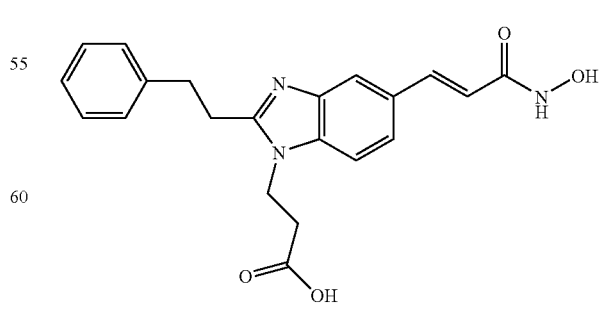
3-[5-(2-Hydrocarbamoyl-vinyl)-2-phenethyl-1H-benzimidazol-1-yl]-propionic acid -continued

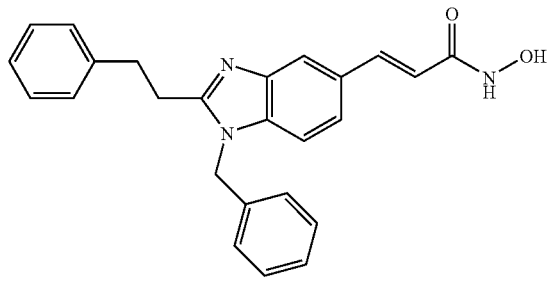

N-Hydroxy-3-(1-Benzyl-2-phenethyl-1H-benzimidazol-5-yl}-acrylamide

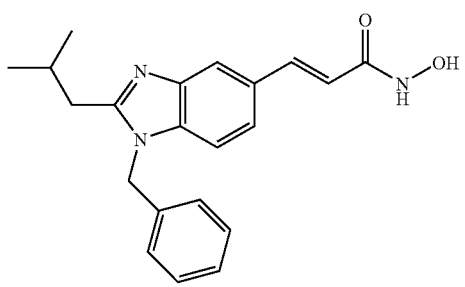

N-Hydroxy-3-(1-Benzyl-2-isobutyl-1H-benzimidazol-5-yl}-acrylamide

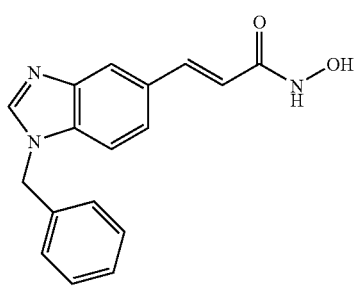

N-Hydroxy-3-(1-benzyl-1H-benzimidazol-5-yl}-acrylamide

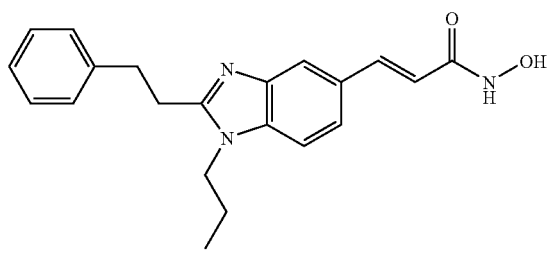

N-Hydroxy-3-(2-phenethyl-1-propyl-1H-benzimidazol-5-yl}-acrylamide

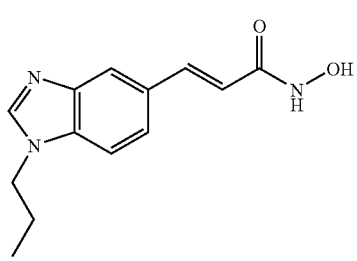

N-Hydroxy-3-(1-propyl-1H-benzimidazol-5-yl}-acrylamide

-continued

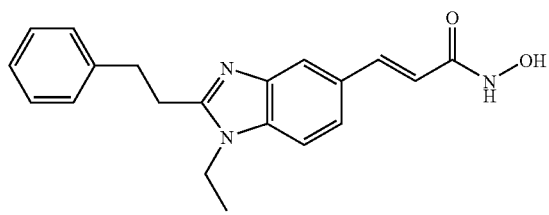

N-Hydroxy-3-(1-Ethyl-2-phenethyl-1H-benzimidazol-5-yl}-acrylamide

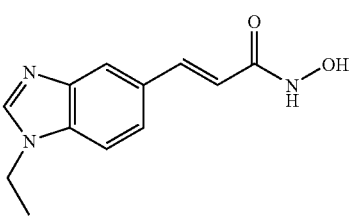

N-Hydroxy-3-(1-Ethyl-1H-benzimidazol-5-yl}-acrylamide

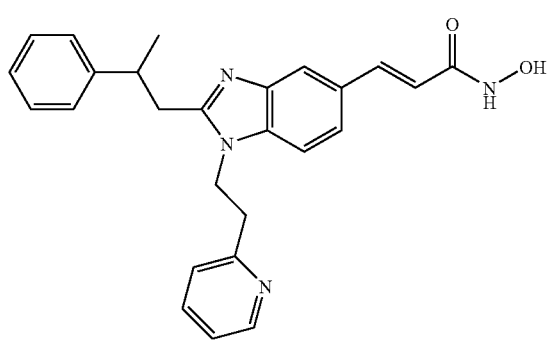

N-Hydroxy-3-[2-(2-phenyl-propyl)-1-(2-pyridin-3-yl-ethyl)-1H-benzimidazol-5-yl]-acrylamide

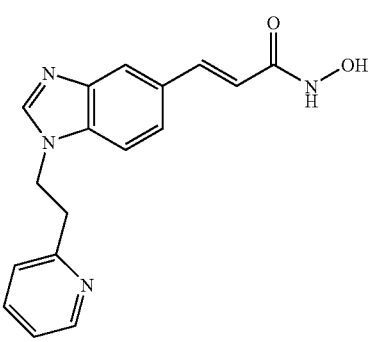

N-Hydroxy-3-[1-(2-pyridin-2-yl-ethyl)-1H-benzimidazol-5-yl]-acrylamide

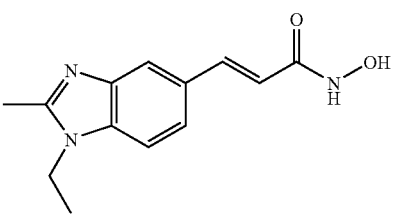

N-Hydroxy-3-(1-Ethyl-2-methyl-1H-benzimidazol-5-yl}-acrylamide

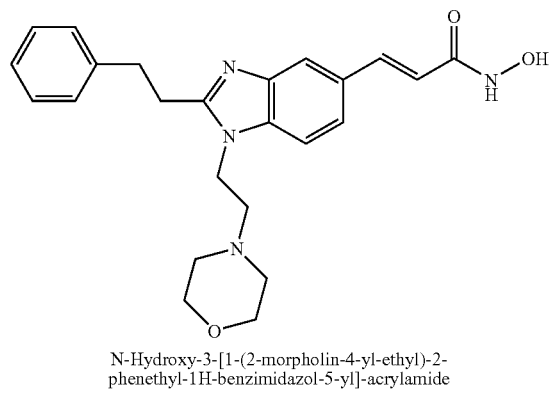

N-Hydroxy-3-[1-(2-morpholin-4-yl-ethyl)-2-phenethyl-1H-benzimidazol-5-yl]-acrylamide

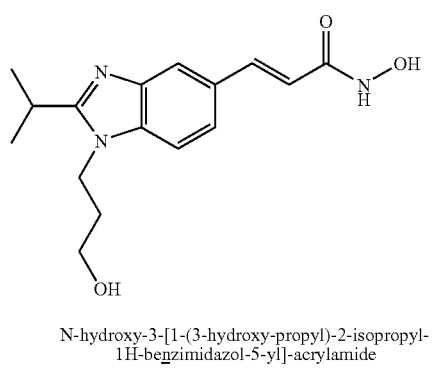

N-hydroxy-3-[1-(3-hydroxy-propyl)-2-isopropyl-1H-benzimidazol-5-yl]-acrylamide

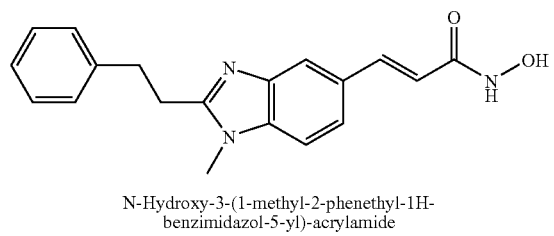

N-Hydroxy-3-(1-methyl-2-phenethyl-1H-benzimidazol-5-yl)-acrylamide

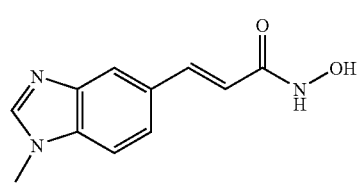

N-Hydroxy-3-(1-methyl-1H-benzimidazol-5-yl)-acrylamide

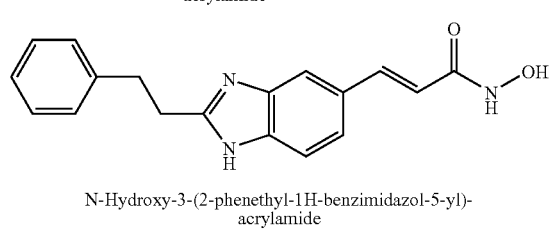

N-Hydroxy-3-(2-phenethyl-1H-benzimidazol-5-yl)-acrylamide

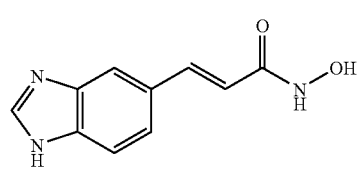

N-Hydroxy-3-(1H-benzimidazol-5-yl)-acrylamide

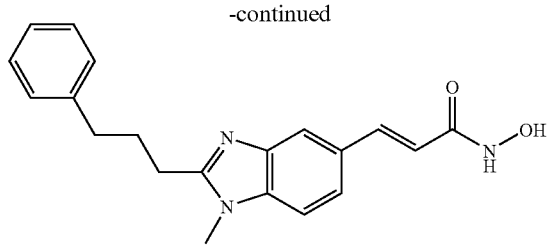

N-Hydroxy-3-[1-methyl-2-(3-phenyl-propyl)-1H-benzimidazol-5-yl]-acrylamide

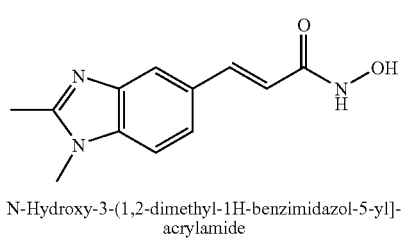

N-Hydroxy-3-(1,2-dimethyl-1H-benzimidazol-5-yl)-acrylamide

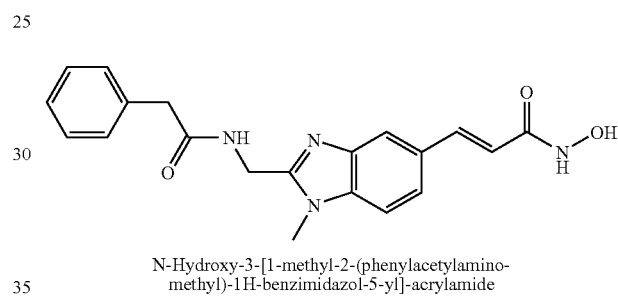

N-Hydroxy-3-[1-methyl-2-(phenylacetylamino-methyl)-1H-benzimidazol-5-yl]-acrylamide

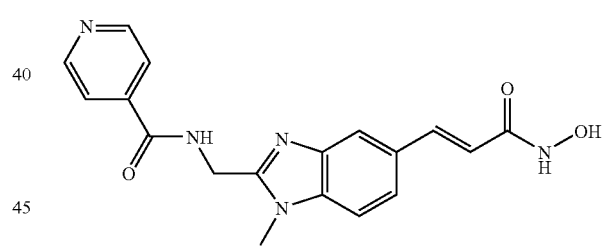

N-[5-(2-Hydroxycarbomoyl-vinyl)-1-methyl-1H-benzimidazol-2-ylmethyl]-isonicotinamide

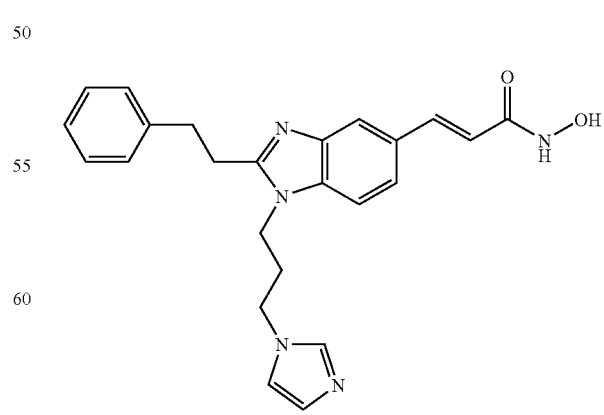

N-Hydroxy-3-[1-(3-imidazol-1-yl-propyl)-2-phenethyl-1H-benzimidazol-5-yl]-acrylamide -continued

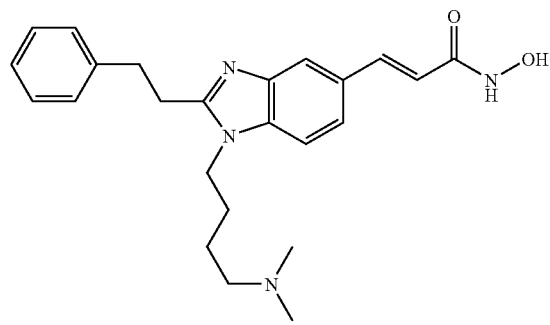

N-Hydroxy-3-[1-(4-dimethylamino-butyl)-2-
phenethyl-1H-benzimidazol-5-yl]-acrylamide

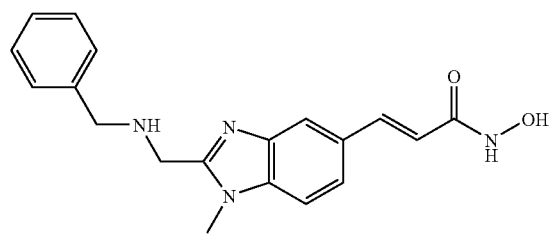

N-Hydroxy-3-[2-(benzylamino-methyl)-1-methyl-1H-
benzimidazol-5-yl]-acrylamide

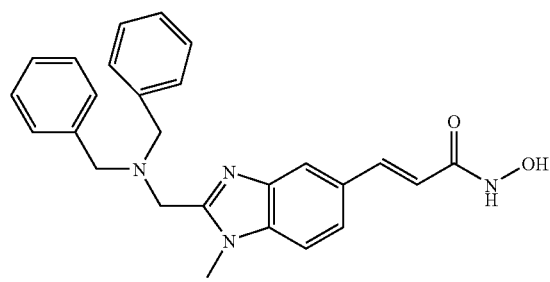

N-Hydroxy-3-{2-[(dibenzylamino)-methyl]-1-
methyl-1H-benzimidazol-5-yl}-acrylamide

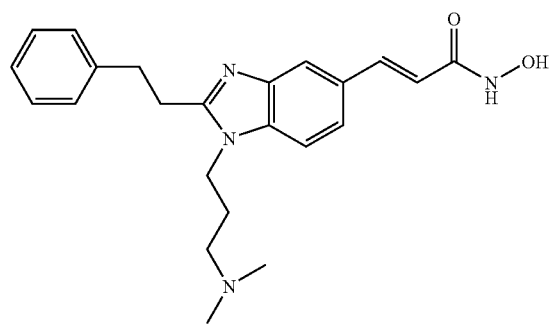

N-Hydroxy-3-[1-(3-dimethylamino-propyl)-2-phenethyl-1H-
benzimidazol-5-yl]-acrylamide -continued

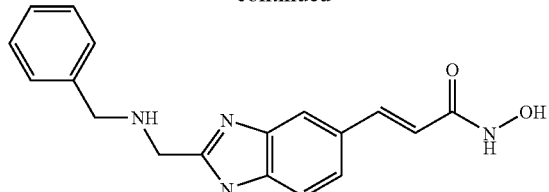

N-Hydroxy-3-[2-(benzylamino-methyl)-ethyl-1H-
benzimidazol-5-yl]-acrylamide

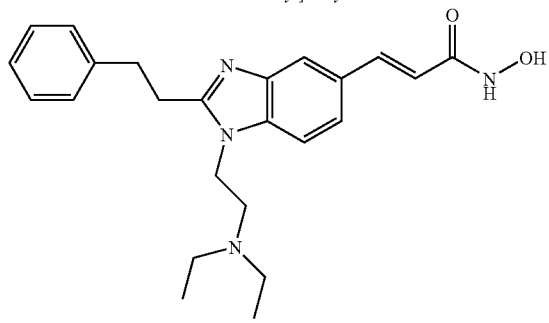

N-Hydroxy-3-[1-(2-diethylamino-ethyl)-2-phenethyl-1H-
benzimidazol-5-yl]-acrylamide

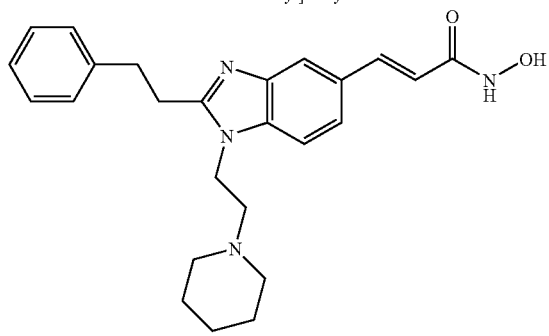

N-Hydroxy-3-[2-phenethyl-1-(piperidin-1-yl-ethyl)-
1H-benzimidazol-5-yl]-acrylamide

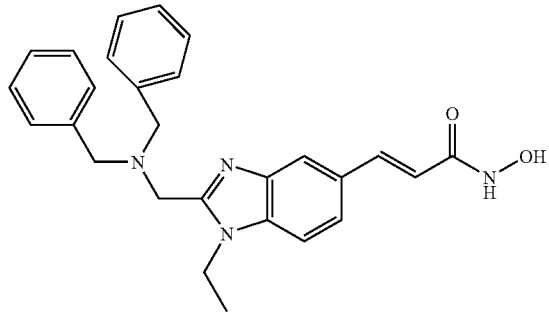

N-Hydroxy-3-{2-[(dibenzylamino)-methyl]-1-ethyl-1H-
benzimidazol-5-yl}-acrylamide

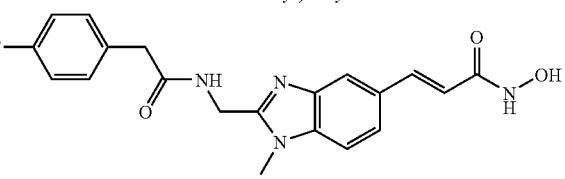

N-Hydroxy-3-(2-{[2-(4-fluoro-phenyl)-acetylamino]-methyl}-
1-methyl-1H-benzimidazol-5-yl)-acrylamide

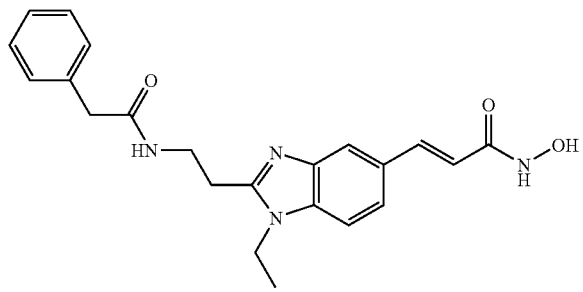

N-Hydroxy-3-[1-ethyl-2-(2-phenylacetylamino-ethyl)-1H-benzimidazol-5-yl]-acrylamide

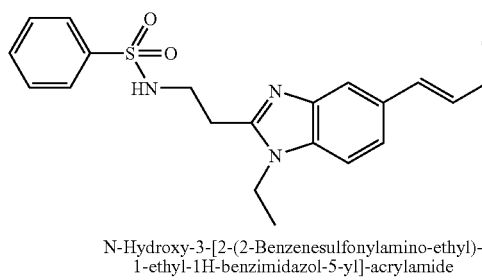

N-Hydroxy-3-[2-(2-Benzenesulfonylamino-ethyl)-1-ethyl-1H-benzimidazol-5-yl]-acrylamide

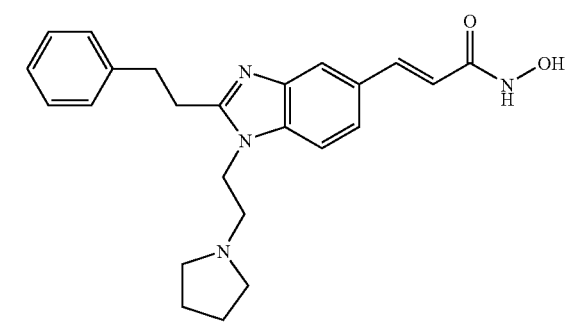

N-Hydroxy-3-[2-phenyethyl-1-(2-pyrrolidin-1-yl-ethyl)-1H-benzimidazol-5-yl]-acrylamide

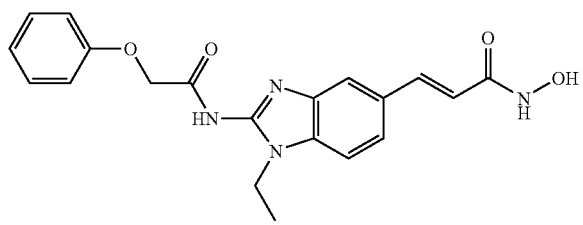

N-Hydroxy-3-{1-ethyl-2-[2-(2-phenoxy-acetylamino)-ethyl]-1H-benimidazol-5-yl}-acrylamide

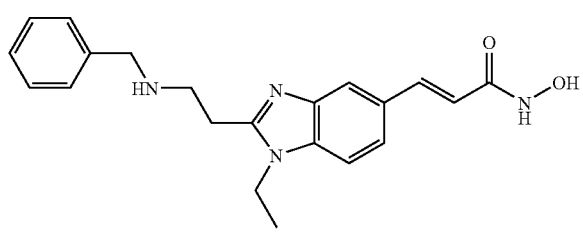

N-Hydroxy-3-[2-(2-benzylamino-ethyl)-1-ethyl-1H-benzimidazol-5-yl]-acrylamide

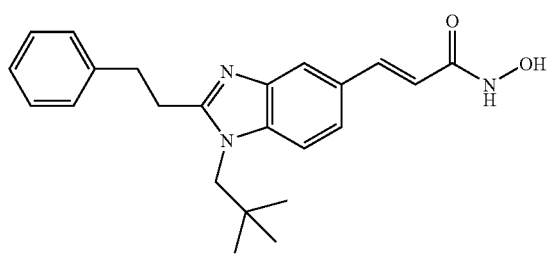

N-Hydroxy-3-[1-(2,2-dimethyl-propyl)-2-phenethyl-1H-benzimidazol-5-yl]-acrylamide

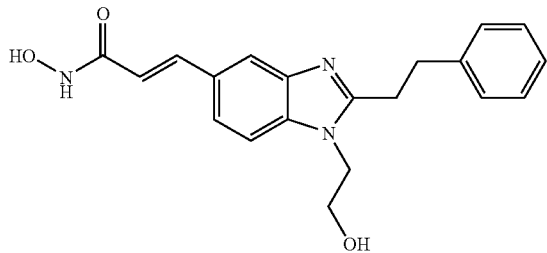

N-Hydroxy-3-[1-(2-hydroxyethyl)-2-phenethyl-1H-benzimidazol-5-yl]-acrylamide

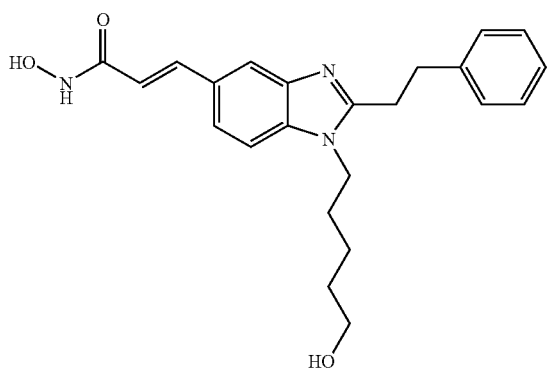

N-Hydroxy-3-[1-(5-hydroxy-pentyl)-2-phenthyl-1H-benzimidazol-5-yl]-acrylamide

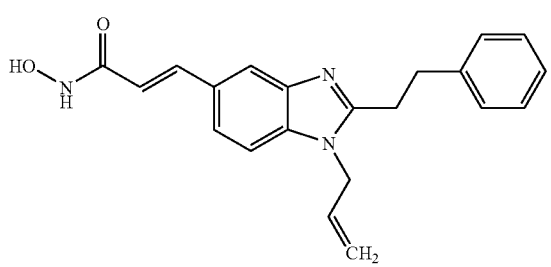

N-Hydroxy-3-(1-allyl-2-phenethyl-1H-benzimidazol-5-yl)-acrylamide

-continued

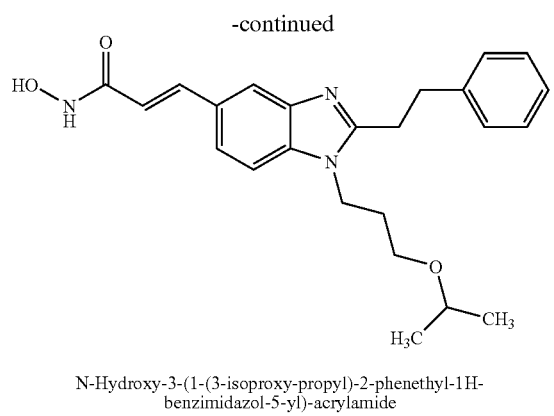

N-Hydroxy-3-(1-(3-isoproxy-propyl)-2-phenethyl-1H-benzimidazol-5-yl)-acrylamide

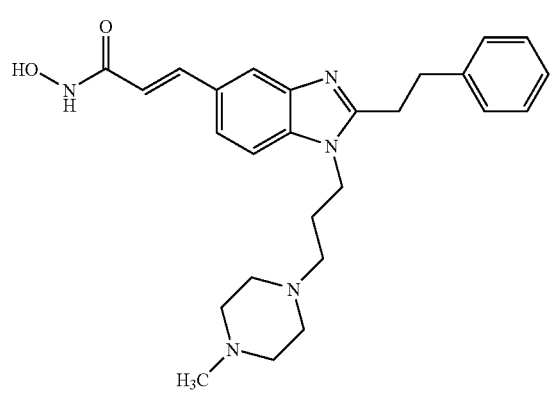

N-Hydroxy-3-{1-[3-(4-methyl-piperzin-1-yl)-2-phenethyl-1H-benzimidazol-5-yl}-acrylamide

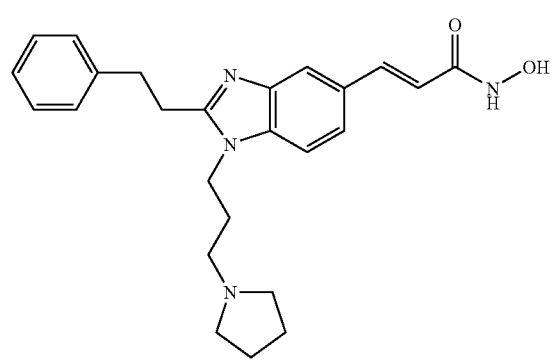

N-Hydroxy-3-[2-phenethyl-1-(3-pyrrolidin-1-yl-propyl)-1H-benzimidazol-5-yl]-acrylamide -continued

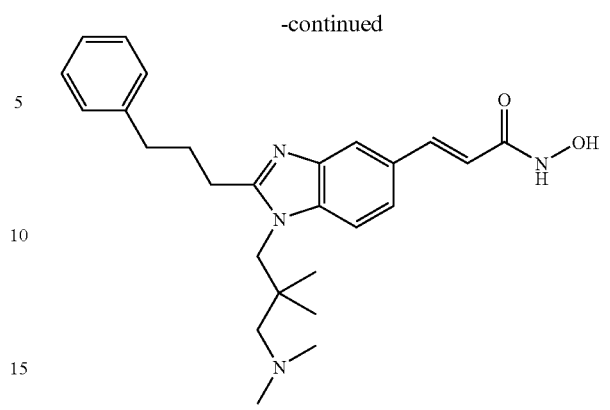

N-Hydroxy-3-[1-(3-Dimethylamino-2,2-dimethyl-propyl)-2-(3-phenyl-propyl)-1H-benzimidazol-5-yl]-acrylamide

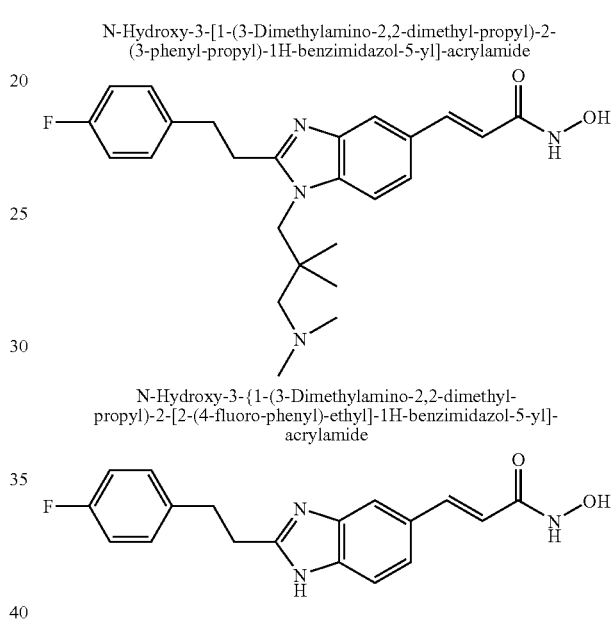

N-Hydroxy-3-{1-(3-Dimethylamino-2,2-dimethyl-propyl)-2-[2-(4-fluoro-phenyl)-ethyl]-1H-benzimidazol-5-yl]-acrylamide N-Hydroxy-3-{2-(4-fluoro-phenyl)-ethyl]-1H-benzimidazol-5-yl}-acrylamide

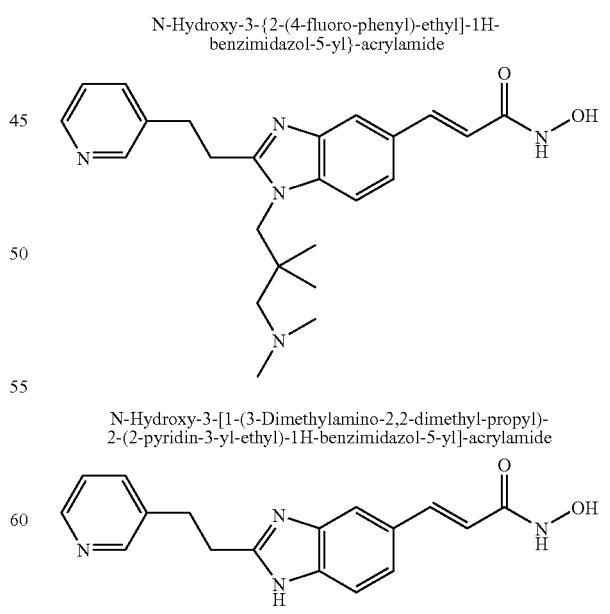

N-Hydroxy-3-[1-(3-Dimethylamino-2,2-dimethyl-propyl)-2-(2-pyridin-3-yl-ethyl)-1H-benzimidazol-5-yl]-acrylamide N-Hydroxy-3-[2-(2-pyridin-3-yl-propyl)-1H-benzimidazol-5-yl]-acrylamide -continued

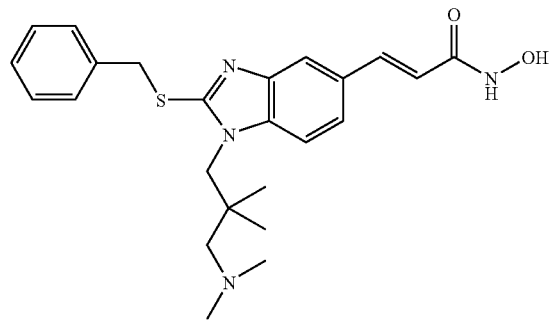

N-Hydroxy-3-[2-benzylsulfanyl-1-(3-dimethylamino-2-2,dimethyl-propyl)-1H-benzimidazol-5-yl]-acrylamide

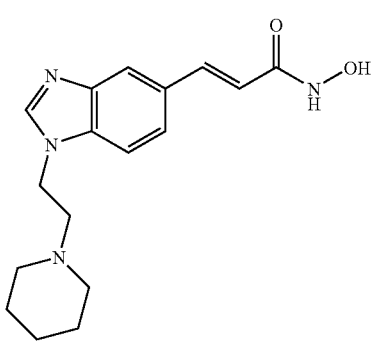

N-Hydroxy-3-[1-(2-piperidin-1-yl-ethyl)-1H-benzimidazol-5-yl]-acrylamide

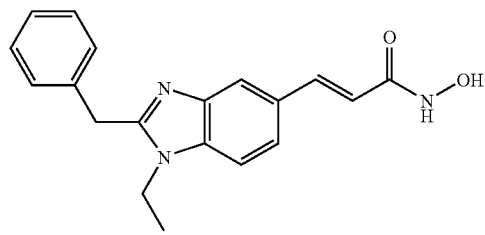

N-Hydroxy-3-(2-benzyl-1-ethyl-1H-benzimidazol-5-yl)-acrylamide

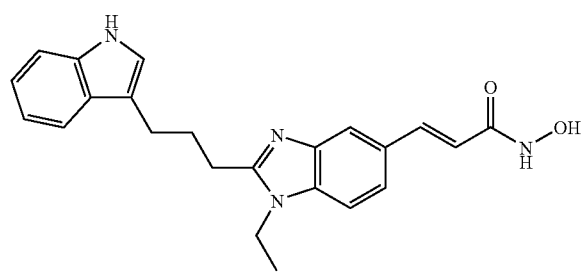

N-Hydroxy-3-{1-ethyl-2-[3-(1H-indol-3-yl)-propyl]-1H-benzimidazol-5-yl)-acrylamide -continued

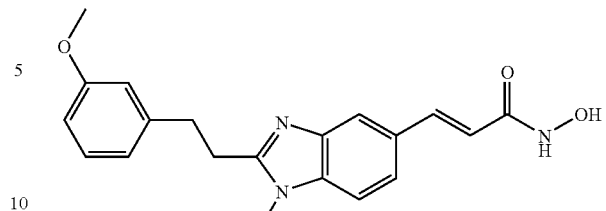

N-Hydroxy-3-{1-(3-dimethylamino-2,2-dimethyl-propyl)-2-[2-(3-methoxy-phenyl)-ethyl]-1H-benzimidazol-5-yl]-acrylamide

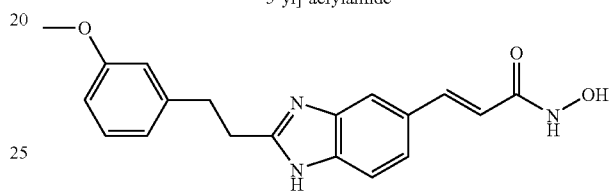

N-Hydroxy-3-{2-(3-methoxy-phenyl)-ethyl]-1H-benzimidazol-5-yl}-acrylamide

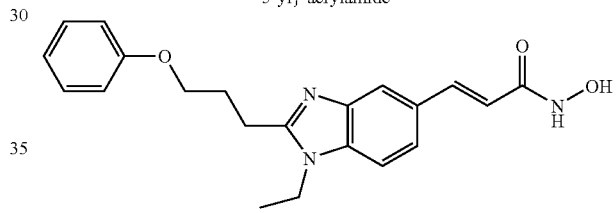

N-Hydroxy-3-[1-ethyl-2-(3-phenoxy-propyl)-1H-benzimidazol-5-yl]-acrylamide

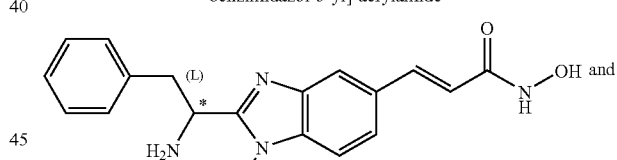

(L)-N-Hydroxy-3-[2-(1-amino-2-phenyl-ethyl)-1-methyl-1H-benzimidazol-5-yl]-acrylamide

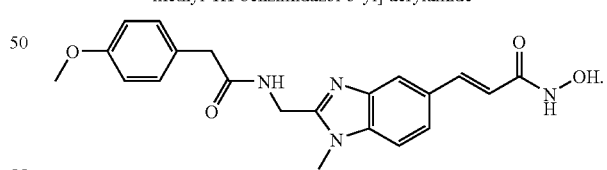

N-Hydroxy-3-(2-{[2-(4-methoxy-phenyl)-acetylamino]-methyl}-1-methyl-1H-benzimidazol-5-yl)-acrylamide 9. A pharmaceutical composition comprising a compound according to claim 1 and a pharmaceutically acceptable diluent, excipient or carrier.

10. The compound of claim 1 wherein the compound is selected from compounds, and their pharmaceutically acceptable salts, selected from the group consisting of

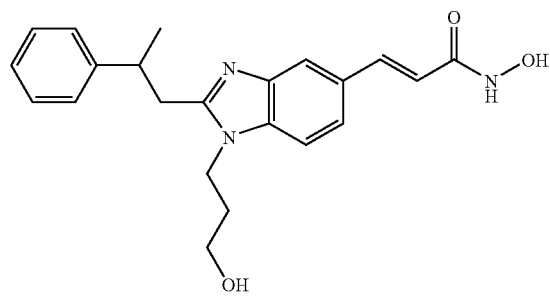

N-Hydroxy-3-[1-(3-hydroxy-propyl)-2-(2-phenyl-propyl)-1H-benzimidazol-5-yl]-acrylamide

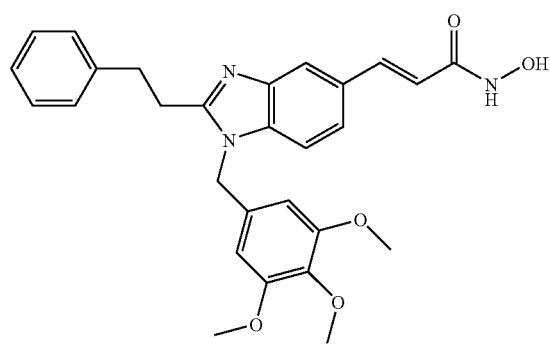

N-Hydroxy-3-[1-(3,4,5-trimethoxybenzyl)-2-(2-phenyl-ethyl)-1H-benzimidazol-5-yl]-acrylamide

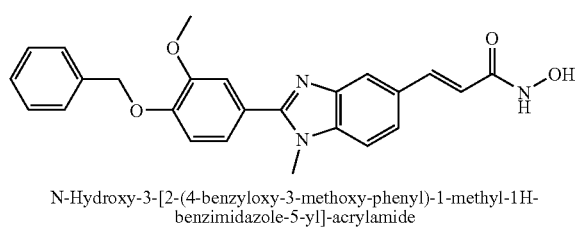

N-Hydroxy-3-[2-(4-benzyloxy-3-methoxy-phenyl)-1-methyl-1H-benzimidazole-5-yl]-acrylamide

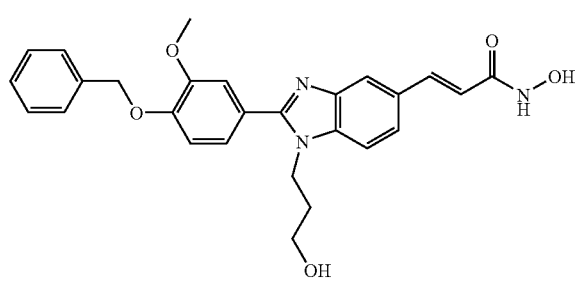

N-Hydroxy-3-[2-(4-benzyloxy-3-methoxy-phenyl)-1-(3-hydroxy-propyl)-1H-benzimidazole-5-yl]-acrylamide

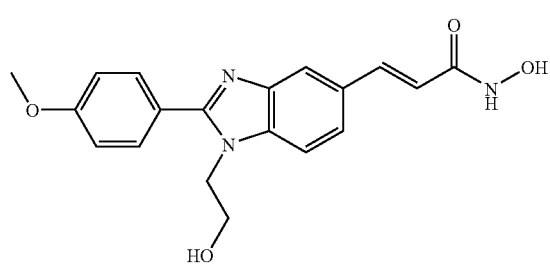

N-Hydroxy-3-[1-(2-hydroxy-ethyl)-2-(4-methoxy-phenyl)-1H-benzimidazole-5-yl]-acrylamide -continued

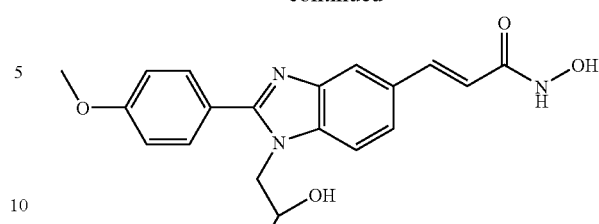

N-Hydroxy-3-[1-(2,3-hydroxy-propyl)-2-(4-methoxy-phenyl)-1H-benzimidazole-5-yl]-acrylamide

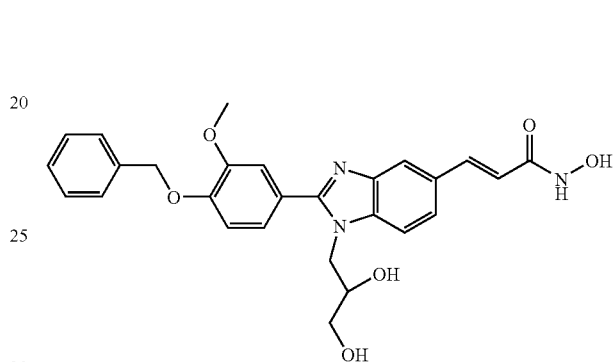

N-Hydroxy-3-[2-(4-benzyloxy-3-methoxy-phenyl)-1-(2,3-hydroxy-propyl)-1H-benzimidazole-5-yl]-acrylamide

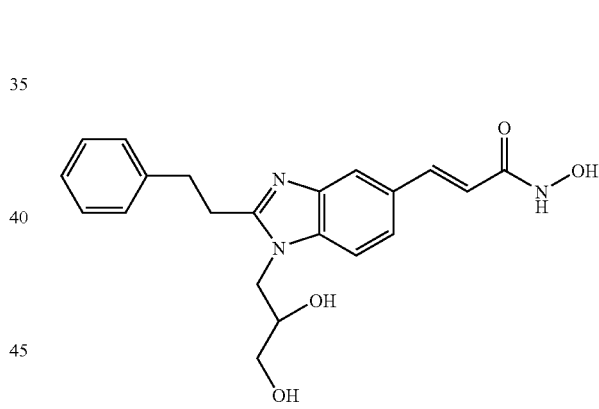

N-Hydroxy-3-[1-(2,3-hydroxy-propyl)-2-(2-phenyl-ethyl)-1H-benzimidazol-5-yl]-acrylamide

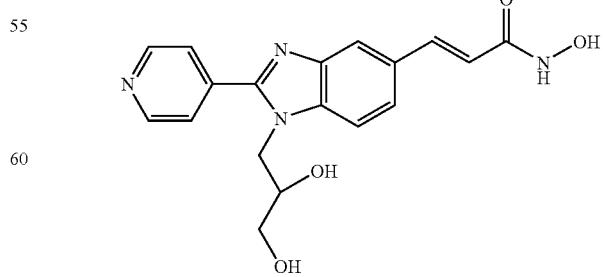

N-Hydroxy-3-[1-(2,3-hydroxy-propyl)-2-(4-pyridyl)-1H-benzimidazol-5-yl]-acrylamide -continued

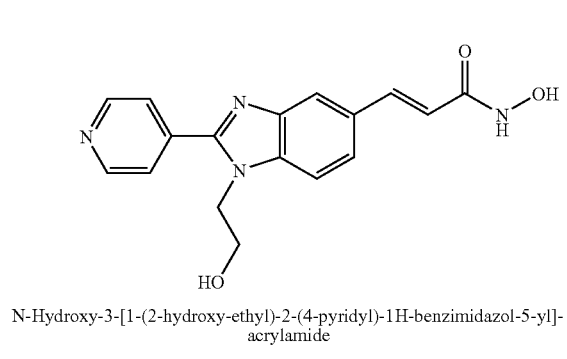

N-Hydroxy-3-[1-(2-hydroxy-ethyl)-2-(4-pyridyl)-1H-benzimidazol-5-yl]-acrylamide

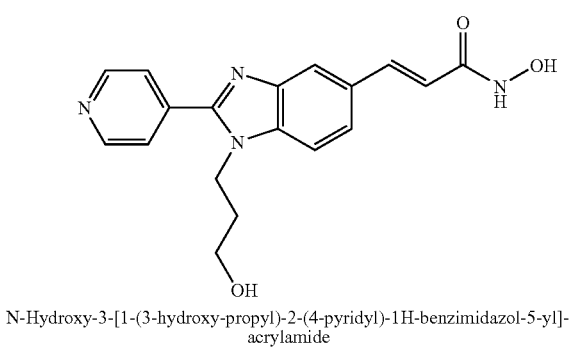

N-Hydroxy-3-[1-(3-hydroxy-propyl)-2-(4-pyridyl)-1H-benzimidazol-5-yl]-acrylamide -continued

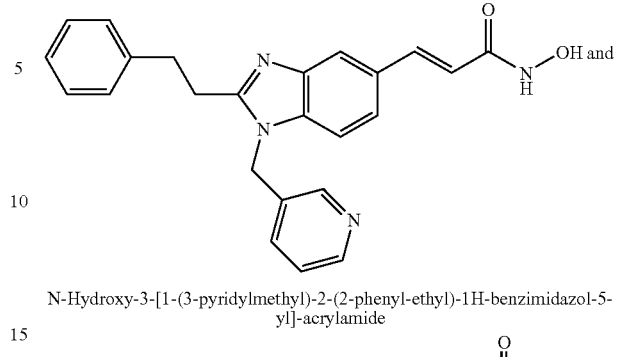

N-Hydroxy-3-[1-(3-pyridylmethyl)-2-(2-phenyl-ethyl)-1H-benzimidazol-5-yl]-acrylamide N-Hydroxy-3-[1-(3-hydroxy-propyl)-2-(2-pyridyl)-1H-benzimidazol-5-yl]-acrylamide.

11. The compound according to claim 1 wherein $R^1$ is selected from the group consisting of: 2-(piperidin-1-yl)-ethyl; 2-(pyrrolidin-1-yl)-ethyl; 2-diethylamino-ethyl; and 3-dimethylamino-2,2-dimethyl-propyl.

* * * * *